US012577248B2

(12) United States Patent
Zhang et al.

(10) Patent No.: US 12,577,248 B2
(45) Date of Patent: Mar. 17, 2026

(54) SUBSTITUTED [1,2,4]TRIAZOLO[1,5-A]PYRAZINES AS SPLEEN TYROSINE KINASE INHIBITORS

(71) Applicant: NANJING RUIJIE PHARMA CO., LTD., Nanjing (CN)

(72) Inventors: Junbo Zhang, Nanjing (CN); Shuhao Zhu, Nanjing (CN); Xiaoxin Qi, Nanjing (CN)

(73) Assignee: NANJING RUIJIE PHARMA CO., LTD., Nanjing (CN)

( * ) Notice: Subject to any disclaimer, the term of this patent is extended or adjusted under 35 U.S.C. 154(b) by 593 days.

(21) Appl. No.: 17/928,616

(22) PCT Filed: May 28, 2021

(86) PCT No.: PCT/CN2021/096827

§ 371 (c)(1),
(2) Date: Nov. 30, 2022

(87) PCT Pub. No.: WO2021/244430

PCT Pub. Date: Dec. 9, 2021

(65) Prior Publication Data

US 2023/0203042 A1 Jun. 29, 2023

(30) Foreign Application Priority Data

Jun. 1, 2020 (WO) ................ PCT/CN2020/093672

(51) Int. Cl.

| | |
|---|---|
| ***A61K 31/4985*** | (2006.01) |
| ***C07D 487/04*** | (2006.01) |
| ***C07D 519/00*** | (2006.01) |

(52) U.S. Cl.
CPC ......... *C07D 487/04* (2013.01); *C07D 519/00* (2013.01)

(58) Field of Classification Search
CPC .......................... A61K 31/4985; C07D 487/04
USPC .......................................... 514/249; 544/350
See application file for complete search history.

(56) References Cited

FOREIGN PATENT DOCUMENTS

| | | | |
|---|---|---|---|
| WO | WO2006044687 | A2 | 4/2006 |
| WO | WO2012163724 | A1 | 12/2012 |
| WO | WO2013064445 | A1 | 5/2013 |
| WO | WO2015158283 | A1 | 10/2015 |

OTHER PUBLICATIONS

Lovering F. et al.; "Imdazotriazines: Spleen Tyrosine Kinase (Syk) Inhibitors Identified by Free-Energy Perturbation (FEP)"; *ChemMedChem*, vol. 11.Sep. 18, 2015(Sep. 18, 2015), pp. 217-233.

*Primary Examiner* — Douglas M Willis
(74) *Attorney, Agent, or Firm* — HDLS IPR SERVICES; Chun-Ming Shih

(57) ABSTRACT

The present invention provides compounds of Formula (I) which can be used as Syk inhibitors and potently as therapeutic agents against diseases mediated by Syk.

Formula (I)

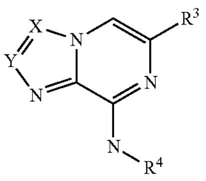

21 Claims, No Drawings

SUBSTITUTED [1,2,4]TRIAZOLO[1,5-A]PYRAZINES AS SPLEEN TYROSINE KINASE INHIBITORS

CROSS-REFERENCE TO RELATED APPLICATIONS

Not Applicable.

STATEMENT REGARDING FEDERALLY SPONSORED RESEARCH OR DEVELOPMENT

Not Applicable.

THE NAMES OF THE PARTIES TO A JOINT RESEARCH AGREEMENT

Not Applicable.

INCORPORATION-BY-REFERENCE OF MATERIAL SUBMITTED ON A COMPACT DISC

Not Applicable.

BACKGROUND OF THE INVENTION

Field of the Invention

The present invention relates to novel compounds and their uses as Spleen Tyrosine Kinase inhibitors. The invention also relates to the usage of such compounds and pharmaceutical compositions for treating a disease or condition selected from cancer, an inflammatory disorder, an allergic disorder, an autoimmune disease.

Description of Related Art

Spleen Tyrosine Kinase (Syk) is a member of the Syk family of tyrosine kinases, and is a regulator of early B-cell development as well as mature B-cell activation, signaling, and survival. Syk is a 72 kDa non-receptor tyrosine kinase belonging to the subfamily of intracellular tyrosine kinases that plays critical roles in immunoreceptor- and integrin-mediated signaling in a variety of cell types, including B cells, macrophages, monocytes, mast cells, eosinophils, basophils, neutrophils, dendritic cells, T cells, natural killer cells, platelets, and osteoclasts. Immunoreceptors as described here include classical immunoreceptors and immunoreceptor-like molecules. Classical immunoreceptors include B-cell and T-cell antigen receptors as well as various immunoglobulin receptors (Fc receptors). Immunoreceptor-like molecules are either structurally related to immunoreceptors or participate in similar signal transduction pathways and are primarily involved in non-adaptive immune functions, including neutrophil activation, natural killer cell recognition, and osteoclast activity. Integrins are cell surface receptors that play key roles in the control of leukocyte adhesion and activation in both innate and adaptive immunity.

Ligand binding leads to activation of both immunoreceptors and integrins, which results in Src family kinases being activated, and phosphorylation of immunoreceptor tyrosine-based activation motifs (ITAMs) in the cytoplasmic face of receptor-associated transmembrane adaptors. Syk binds to the phosphorylated ITAMs of the adaptors, leading to activation of Syk and subsequent phosphorylation and activation of downstream signaling pathways.

Syk is essential for B-cell activation through B-cell receptor (BCR) signaling. Syk becomes activated upon binding to phosphorylated BCR and thus initiates the early signaling events following BCR activation. B-cell signaling through BCR can lead to a wide range of biological outputs, which in turn depend on the developmental stage of the B-cell. The magnitude and duration of BCR signals must be precisely regulated. Aberrant BCR-mediated signaling can cause disregulated B-cell activation and/or the formation of pathogenic auto-antibodies leading to multiple autoimmune and/or inflammatory diseases. Mice lacking Syk show impaired maturation of B-cells, diminished immunoglobulin production, compromised T-cell-independent immune responses and marked attenuation of the sustained calcium sign upon BCR stimulation.

A large body of evidence supports the role of B-cells and the humoral immune system in the pathogenesis of autoimmune and/or inflammatory diseases. Protein-based therapeutics (such as Rituxan) developed to deplete B-cells represent an approach to the treatment of a number of autoimmune and inflammatory diseases. Auto-antibodies and their resulting immune complexes are known to play pathogenic roles in autoimmune disease and/or inflammatory disease. The pathogenic response to these antibodies is dependent on signaling through Fc Receptors, which is, in turn, dependent upon Syk. Because of Syk's role in B-cell activation, as well as FcR dependent signaling, inhibitors of Syk can be useful as inhibitors of B-cell mediated pathogenic activity, including autoantibody production. Therefore, inhibition of Syk enzymatic activity in cells is proposed as a treatment for autoimmune disease through its effects on autoantibody production.

Syk also plays a key role in FCeRI mediated mast cell degranulation and eosinophil activation. Thus, Syk is implicated in allergic disorders including asthma. Syk binds to the phosphorylated gamma chain of FCeRI via its SH2 domains and is essential for downstream signaling. Syk deficient mast cells demonstrate defective degranulation, arachidonic acid, and cytokine secretion. This also has been shown for pharmacologic agents that inhibit Syk activity in mast cells. Treatment with Syk antisense oligonucleotides inhibits antigen-induced infiltration of eosinophils and neutrophils in an animal model of asthma. Syk deficient eosinophils also show impaired activation in response to FCeRI stimulation. Therefore, small molecule inhibitors of Syk will be useful for treatment of allergy-induced inflammatory diseases including asthma.

Syk is also expressed in mast cells and monocytes and has been shown to be important for the function of these cells. For example, Syk deficiency in mice is associated with impaired IgE-mediated mast cell activation, which is marked diminution of TNF-alpha and other inflammatory cytokine release. Syk kinase inhibitors have also been shown to inhibit mast cell degranulation in cell-based assays. Additionally, Syk inhibitors have been shown to inhibit antigen-induced passive cutaneous anaphylaxsis, bronchoconstriction and bronchial edema in rats. In addition, SYK is required for the bone resorption activity of osteoclasts. Upon stimulation of osteoclasts by $\alpha v\beta 3$ integrin, SYK becomes phosphorylated, most likely by c-Src, in a DAP-12/Fc$\gamma$RII dependent mechanism, leading to SPL-76 and Vav3 phosphorylation and subsequent cytoskeletal reorganisation. SYK deficient osteoclasts are inactive and show defective cytoskeletal reorganisation. In correlation with this, SYK deficient embryos show defective skeletal mass.

Thus, the inhibition of Syk activity can be useful for the treatment of allergic disorders, autoimmune diseases, and inflammatory diseases such as: SLE, arterial thrombosis and thromboinflammatory brain infarction, rheumatoid arthritis, multiple vasculitides, idiopathic thrombocytopenia purpura (ITP), myasthenia gravis, allergic rhinitis, chronic obstructive pulmonary disease (COPD), adult respiratory distress syndrome (ARDs) and asthma etc. In addition, Syk has been reported to play an important role in ligand-independent tonic signaling through the B-cell receptor, known to be an important survival signal in B-cells. Thus, inhibition of Syk activity may also be useful in treating certain types of cancer, including hematological malignancies, B-cell lymphoma, and leukemia etc.

The present invention relates to compounds and to the use of compounds in which the inhibition, regulation and/or modulation of signal transduction by kinases, in particular tyrosine kinases, furthermore to pharmaceutical compositions which comprise these compounds, and to the use of the compounds for the treatment of kinase-induced diseases, including cancer and inflammatory conditions.

BRIEF SUMMARY OF THE INVENTION

The present disclosure provides novel compounds that function as Syk inhibitors. In some embodiments, the disclosure provides compounds of Formula (I):

Formula (I)

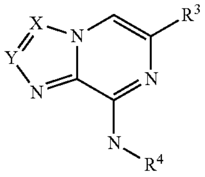

wherein

X is $CR^1$ or N, Y is $CR^2$ or N, and at least one of X and Y is N; $R^1$ is H; $R^2$ is H;

$R^3$ is phenyl, pyrazinyl, pyridinyl, pyrazolyl, indazolyl, benzothiazolyl, benzodioxolyl, thiazolyl, indolyl, isoindolyl, 2H-pyrido[3,2-b][1,4]oxazin-3(4H)-one-yl, 2H-1,4-benzoxazin-3(4H)-one-yl; wherein the phenyl, pyrazinyl, pyridinyl, pyrazolyl, indazolyl, benzothiazolyl, benzodioxolyl, thiazolyl, indolyl, isoindolyl, 2H-pyrido[3,2-b][1,4]oxazin-3(4H)-one-yl, 2H-1,4-benzoxazin-3(4H)-one-yl may be optionally substituted with zero, one, two, or three substituents independently selected from the group consisting of carboxyl, amino, halo, $C_{1-6}$ alkyl, $C_{1-6}$ alkoxy, $C_{2-6}$ alkenyl, $C_{2-6}$ alkynyl, $C_{3-8}$ cycloalkyl, —C(O)—NHR$^5$; wherein $R^5$ is independently selected from the group consisting of hydrogen, benzoyloxy, $C_{1-6}$ alkyl, $C_{2-6}$ alkenyl, $C_{2-6}$ alkynyl;

$R^4$ is phenyl, pyridinyl, benzodioxolyl; wherein the phenyl, pyridinyl, benzodioxolyl may be optionally substituted with zero, one, two, or three substituents independently selected from the group consisting of halo, $C_{1-6}$ alkyl, $C_{1-6}$ alkoxy, $C_{3-8}$ cycloalkoxy, piperazinyl,

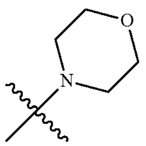,
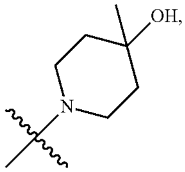
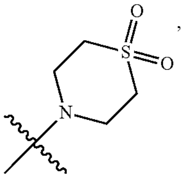,
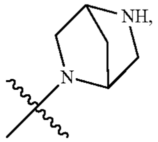
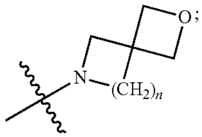

wherein the $C_{1-6}$ alkyl, $C_{1-6}$ alkoxy may be optionally substituted with zero, one, two, or three haloes, wherein the piperazinyl may be optionally substituted with one or two substituents independently selected from the group consisting of $C_{1-6}$ alkyl, $C_{3-8}$ cycloalkyl, oxacycloalkyl of $C_{2-6}$, ethylsulfonyl, methylsulfonyl, hydroxyethyl, methoxyethyl, trifluoromethyl, trifluoroethyl, wherein the

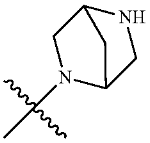 [SMILES: *N1CC2CC1CN2]

is optionally substituted with one or two substituents independently selected from the group consisting of $C_{1-6}$ alkyl, oxacycloalkyl of $C_{2-6}$; wherein n is 1 or 2;

or a pharmaceutically acceptable salt, ester, stereoisomer, mixture of stereoisomers or tautomer thereof.

In some embodiments, wherein X is N; Y is $CR^2$; $R^2$ is H; $R^3$ is phenyl, pyrazinyl, pyridinyl, pyrazolyl, indazolyl, thiazolyl, indolyl, isoindolyl, 2H-pyrido[3,2-b][1,4]oxazin-3(4H)-one-yl, 2H-1,4-benzoxazin-3(4H)-one-yl; wherein the phenyl, pyrazinyl, pyridinyl, pyrazolyl, indazolyl, thiazolyl, indolyl, isoindolyl, 2H-pyrido[3,2-b][1,4]oxazin-3(4H)-one-yl, 2H-1,4-benzoxazin-3(4H)-one-yl may be optionally substituted with zero, one, two, or three substituents independently selected from the group consisting of carboxyl, amino, halo, $C_{1-6}$ alkyl, $C_{1-6}$ alkoxy, $C_{2-6}$ alkenyl, $C_{2-6}$ alkynyl, $C_{3-8}$ cycloalkyl, —C(O)—NHR$^5$; wherein $R^5$ is independently selected from the group consisting of hydrogen, benzoyloxy, $C_{1-6}$ alkyl, $C_{2-6}$ alkenyl, $C_{2-6}$ alkynyl.

In some embodiments, wherein X is N; Y is $CR^2$; $R^2$ is H; $R^3$ is indazolyl, indolyl, 2H-pyrido[3,2-b][1,4]oxazin-3(4H)-one-yl, 2H-1,4-benzoxazin-3(4H)-one-yl; wherein indazolyl, indolyl, 2H-pyrido[3,2-b][1,4]oxazin-3(4H)-one-yl, 2H-1,4-benzoxazin-3(4H)-one-yl may be optionally substituted with zero, one, two, or three substituents independently selected from the group consisting of halo, $C_{1-6}$ alkyl, $C_{1-6}$ alkoxy.

In some embodiments, wherein X is N; Y is $CR^2$; $R^2$ is H; $R^3$ is phenyl, pyrazinyl; wherein the phenyl, pyrazinyl may be optionally substituted with zero, one, two, or three substituents independently selected from the group consisting of carboxyl, amino, halo, $C_{1-6}$ alkyl, $C_{1-6}$ alkoxy, —C(O)—NHR$^5$; wherein $R^5$ is independently selected from the group consisting of hydrogen, benzoyloxy, $C_{1-6}$ alkyl, $C_{2-6}$ alkenyl, $C_{2-6}$ alkynyl.

In some embodiments, wherein $R^4$ is phenyl, pyridinyl; wherein the phenyl, pyridinyl may be optionally substituted with zero, one, two, or three substituents independently selected from the group consisting of halo, $C_{1-6}$ alkyl, $C_{1-6}$ alkoxy, $C_{3-8}$ cycloalkoxy, piperazinyl,

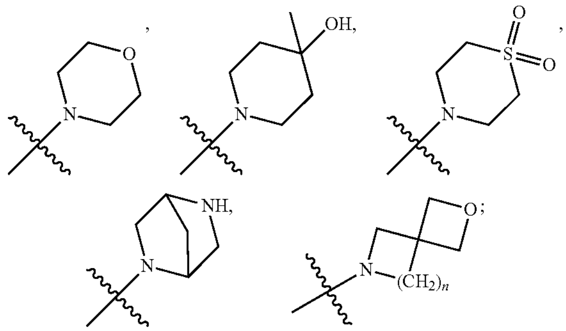

wherein the $C_{1-6}$ alkyl, $C_{1-6}$ alkoxy may be optionally substituted with zero, one, two, or three haloes, wherein the piperazinyl may be optionally substituted with one or two substituents independently selected from the group consisting of $C_{1-6}$ alkyl, $C_{3-8}$ cycloalkyl, oxetanyl, ethylsulfonyl, methylsulfonyl, hydroxyethyl, methoxyethyl, trifluoromethyl, trifluoroethyl, wherein the

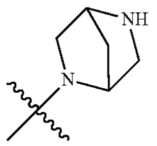 [SMILES: *N1CC2CC1CN2]

is optionally substituted with one or two substituents independently selected from the group consisting of $C_{1-6}$ alkyl, oxetanyl; wherein n is 1 or 2.

In some embodiments, wherein $R^4$ is benzodioxolyl; wherein the benzodioxolyl may be optionally substituted with zero, one, two, or three substituents independently selected from the group consisting of halo, $C_{1-6}$ alkyl, $C_{1-6}$ alkoxy; wherein the $C_{1-6}$ alkyl, $C_{1-6}$ alkoxy may be optionally substituted with zero, one, two, or three haloes.

In some embodiments, wherein $R^4$ is phenyl, pyridinyl; wherein the phenyl, pyridinyl may be optionally substituted with zero, one, two, or three substituents independently selected from the group consisting of halo, $C_{1-6}$ alkyl, $C_{1-6}$ alkoxy, $C_{3-8}$ cycloalkoxy, piperazinyl,

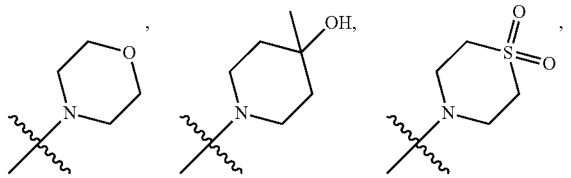

-continued

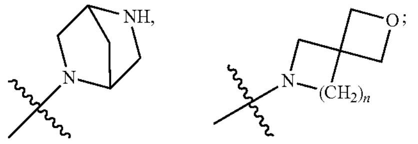

wherein the $C_{1-6}$ alkyl, $C_{1-6}$ alkoxy may be optionally substituted with zero, one, two, or three haloes, wherein the piperazinyl may be optionally substituted with one or two substituents independently selected from the group consisting of $C_{1-6}$ alkyl, $C_{3-8}$ cycloalkyl, oxetanyl, ethylsulfonyl, methylsulfonyl, hydroxyethyl, methoxyethyl, trifluoromethyl, trifluoroethyl, wherein the

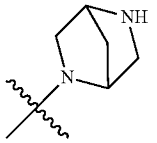 [SMILES: *N1CC2CC1CN2]

is optionally substituted with one or two substituents independently selected from the group consisting of $C_{1-6}$ alkyl, oxetanyl; wherein n is 1 or 2.

In some embodiments, wherein $R^4$ is benzodioxolyl; wherein the benzodioxolyl may be optionally substituted with zero, one, two, or three substituents independently selected from the group consisting of halo, $C_{1-6}$ alkyl, $C_{1-6}$ alkoxy; wherein the $C_{1-6}$ alkyl, $C_{1-6}$ alkoxy may be optionally substituted with zero, one, two, or three haloes.

In some embodiments, wherein $R^4$ is phenyl, pyridinyl; wherein the phenyl, pyridinyl may be optionally substituted with zero, one, two, or three substituents independently selected from the group consisting of halo, $C_{1-6}$ alkyl, $C_{1-6}$ alkoxy, $C_{3-8}$ cycloalkoxy, piperazinyl,

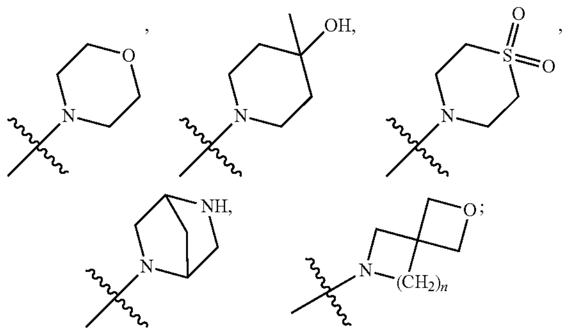

wherein the $C_{1-6}$ alkyl, $C_{1-6}$ alkoxy may be optionally substituted with zero, one, two, or three haloes, wherein the piperazinyl may be optionally substituted with one or two substituents independently selected from the group consisting of $C_{1-6}$ alkyl, $C_{3-8}$ cycloalkyl, oxetanyl, ethylsulfonyl, methylsulfonyl, hydroxyethyl, methoxyethyl, trifluoromethyl, trifluoroethyl, wherein the

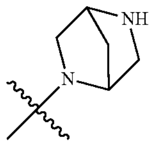 [SMILES: *N1CC2CC1CN2]

is optionally substituted with one or two substituents independently selected from the group consisting of $C_{1-6}$ alkyl, oxetanyl; wherein n is 1 or 2.

In some embodiments, wherein $R^4$ is benzodioxolyl; wherein the benzodioxolyl may be optionally substituted with zero, one, two, or three substituents independently selected from the group consisting of halo, $C_{1-6}$ alkyl, $C_{1-6}$ alkoxy; wherein the $C_{1-6}$ alkyl, $C_{1-6}$ alkoxy may be optionally substituted with zero, one, two, or three haloes.

In some embodiments, wherein X is $CR^1$; Y is N; $R^1$ is H;

$R^3$ is phenyl, pyrazinyl, pyridinyl, pyrazolyl, indazolyl, thiazolyl, indolyl, isoindolyl, 2H-pyrido[3,2-b][1,4]oxazin-3(4H)-one-yl, 2H-1,4-benzoxazin-3(4H)-one-yl; wherein the phenyl, pyrazinyl, pyridinyl, pyrazolyl, indazolyl, thiazolyl, indolyl, isoindolyl, 2H-pyrido[3,2-b][1,4]oxazin-3(4H)-one-yl, 2H-1,4-benzoxazin-3(4H)-one-yl may be optionally substituted with zero, one, two, or three substituents independently selected from the group consisting of carboxyl, amino, halo, $C_{1-6}$ alkyl, $C_{1-6}$ alkoxy, $C_{2-6}$ alkenyl, $C_{2-6}$ alkynyl, $C_{3-8}$ cycloalkyl, —C(O)—$NHR^5$; wherein $R^5$ is independently selected from the group consisting of hydrogen, benzoyloxy, $C_{1-6}$ alkyl, $C_{2-6}$ alkenyl, $C_{2-6}$ alkynyl.

In some embodiments, wherein X is $CR^1$; Y is N; $R^1$ is H;

$R^3$ is pyridinyl, pyrazolyl, indazolyl, thiazolyl, indolyl, isoindolyl, 2H-pyrido[3,2-b][1,4]oxazin-3(4H)-one-yl, 2H-1,4-benzoxazin-3(4H)-one-yl; wherein the pyridinyl, pyrazolyl, indazolyl, thiazolyl, indolyl, isoindolyl, 2H-pyrido[3,2-b][1,4]oxazin-3(4H)-one-yl, 2H-1,4-benzoxazin-3(4H)-one-yl may be optionally substituted with zero, one, two, or three substituents independently selected from the group consisting of halo, $C_{1-6}$ alkyl, $C_{1-6}$ alkoxy, $C_{2-6}$ alkenyl, $C_{2-6}$ alkynyl, $C_{3-8}$ cycloalkyl, —C(O)—$NHR^5$; wherein $R^5$ is independently selected from the group consisting of hydrogen, benzoyloxy, $C_{1-6}$ alkyl, $C_{2-6}$ alkenyl, $C_{2-6}$ alkynyl;

$R^4$ is phenyl, pyridinyl; wherein the phenyl, pyridinyl may be optionally substituted with zero, one, two, or three substituents independently selected from the group consisting of halo, $C_{1-6}$ alkyl, $C_{1-6}$ alkoxy, piperazinyl,

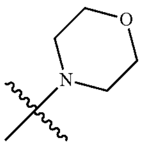
,
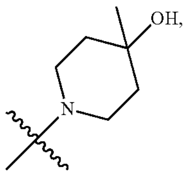
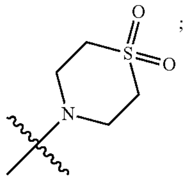
;

wherein the $C_{1-6}$ alkyl, $C_{1-6}$ alkoxy may be optionally substituted with zero, one, two, or three haloes, wherein the piperazinyl may be optionally substituted with one or two substituents independently selected from the group consisting of $C_{1-6}$ alkyl, $C_{3-8}$ cycloalkyl, oxetanyl, ethylsulfonyl, methylsulfonyl, hydroxyethyl, methoxyethyl, trifluoromethyl, trifluoroethyl.

In one embodiment, the compound is selected from:

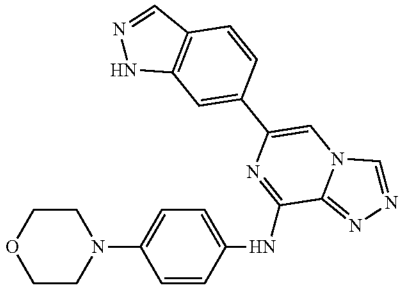

6-(1H-indazol-6-yl)-N-(4-morpholinophenyl)-[1,2,4]triazolo[4,3-a]pyrazin-8-amine

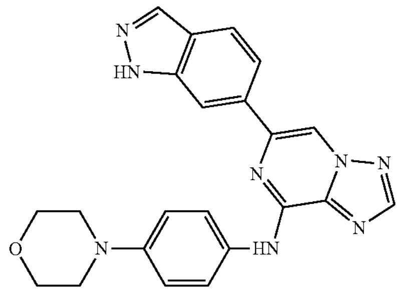

6-(1H-indazol-6-yl)-N-(4-morpholinophenyl)-[1,2,4]triazolo[1,5-a]pyrazin-8-amine

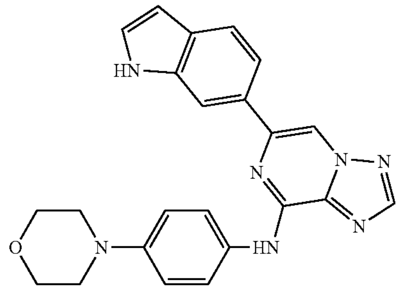

6-(1H-indol-6-yl)-N-(4-morpholinophenyl)-[1,2,4]triazolo[1,5-a]pyrazin-8-amine

-continued

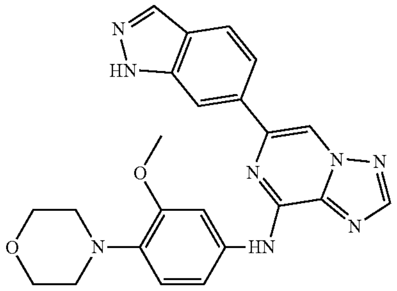

6-(1H-indazol-6-yl)-N-(3-methoxy-4-morpholinophenyl)-[1,2,4]triazolo[1,5-a]pyrazin-8-amine

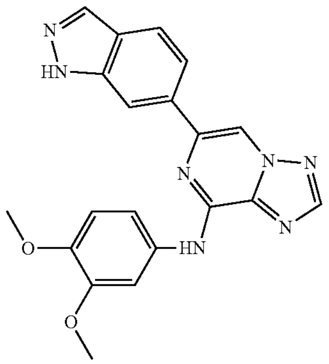

N-(3,4-dimethoxyphenyl)6-(1H-indazol-6-yl)-[1,2,4]triazolo[1,5-a]pyrazin-8-amine

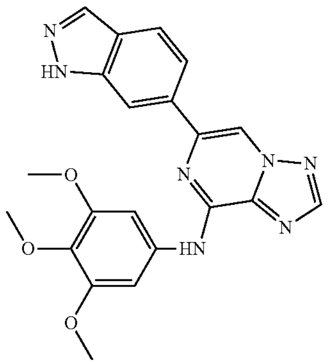

6-(1H-indazol-6-yl)-N-[3,4,5-trimethoxyphenyl)-[1,2,4]triazolo[1,5-a]pyrazin-8-amine -continued

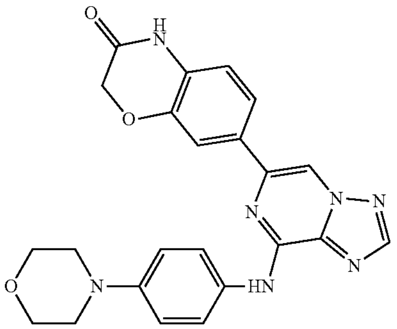

7-(8-((4-morpholinophenyl)amino)-[1,2,4]triazolo[1,5-a]pyrazin-6-yl)-2H-benzo[b][1,4]oxazin-3(4H)-one

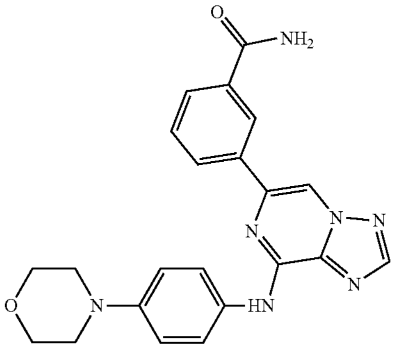

3-(8-((4-morpholinophenyl)amino)-[1,2,4]triazolo[1,5-a]pyrazin-6-yl)benzamide

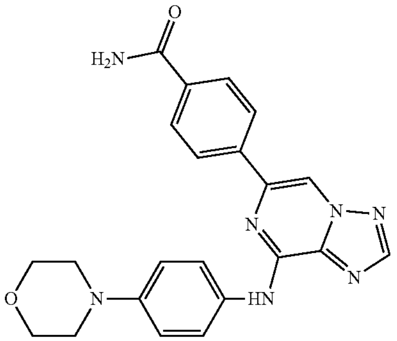

4-(8-((4-morpholinophenyl)amino)-[1,2,4]triazolo[1,5-a]pyrazin-6-yl)benzamide

-continued

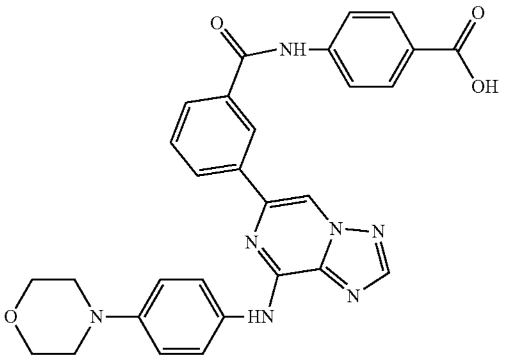

4-(3-(8-((4-morpholinophenyl)amino)-[1,2,4]triazolo[1,5-a]pyrazin-6-yl)benzamido)benzoic acid

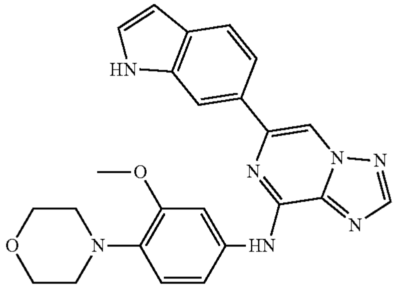

6-(1H-indol-6-yl)-N-(3-methoxy-4-morpholinophenyl)-[1,2,4]triazolo[1,5-a]pyrazin-6-yl)benzamide

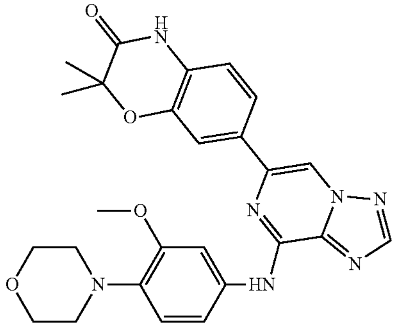

7-(8-((3-methoxy-4-morpholinophenyl)amino)-[1,2,4]triazolo[1,5-a]pyrazin-6-yl)-2,2-dimethyl-2H-benzo[b][1,4]oxazin-3(4H)-one -continued

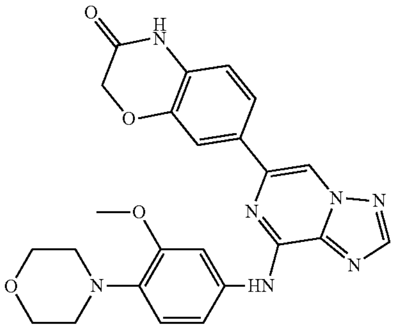

7-(8-((3-methoxy-4-morpholinophenyl)amino)-[1,2,4]triazolo[1,5-a]pyrazin-6-yl)-2H-benzo[b][1,4]oxazin-3(4H)-one

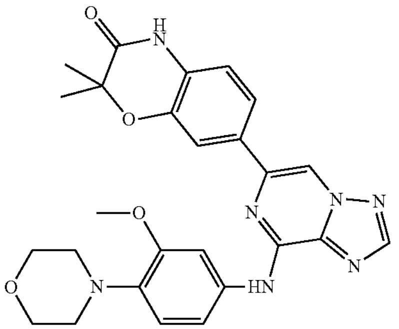

2,2-dimethyl-7-(8-((4-morpholinophenyl)amino)-[1,2,4]triazolo[1,5-a]pyrazin-6-yl)-2H-benzo[b][1,4]oxazin-3(4H)-one

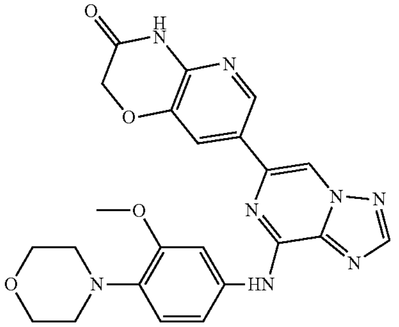

7-(8-((3-methoxy-4-morpholinophenyl)amino)-[1,2,4]triazolo[1,5-a]pyrazin-6-yl)-2H-pyrido[3,2-b][1,4]oxazin-3(4H)-one -continued

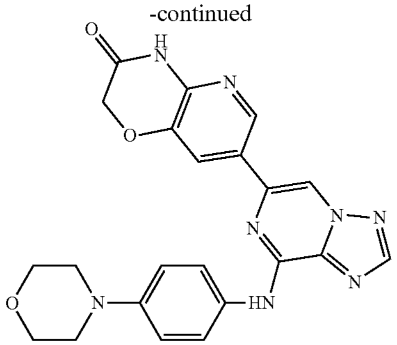

7-(8-((4-morpholinophenyl)amino)-[1,2,4]triazolo[1,5-a]pyrazin-6-yl)-2H-pyrido[3,2-b][1,4]oxazin-3(4H)-one

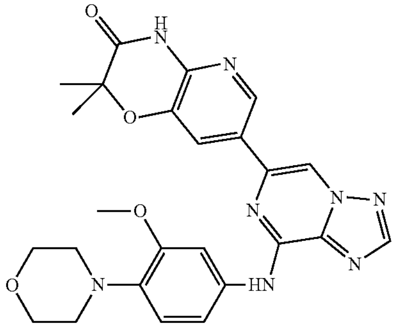

7-(8-((3-methoxy-4-morpholinophenyl)amino)-[1,2,4]triazolo[1,5-a]pyrazin-6-yl)-2,2-dimethyl-2H-pyrido[3,2-b][1,4]oxazin-3(4H)-one

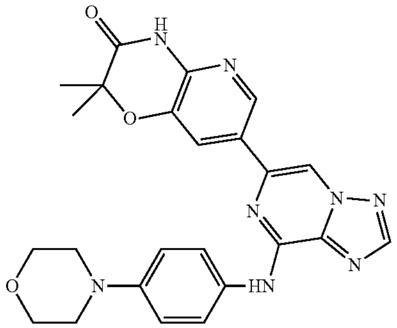

2,2-dimethyl-7-(8-((4-morpholinophenyl)amino)-[1,2,4]triazolo[1,5-a]pyrazin-6-yl)-2H-pyrido[3,2-b][1,4]oxazin-3(4H)-one -continued

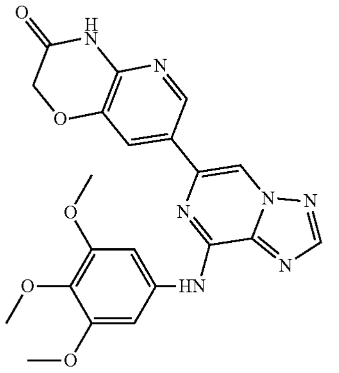

7-(8-((3,4,5-trimethoxyphenyl)amino)-[1,2,4]triazolo[1,5-a]pyrazin-6-yl)-2H-pyrido[3,2-b][1,4]oxazin-3(4H)-one

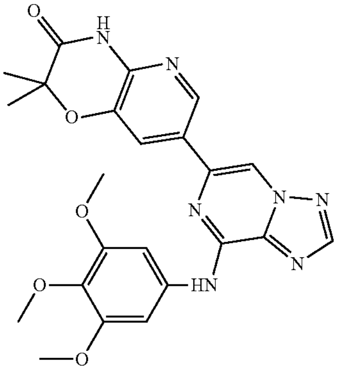

2,2-dimethyl-7-(8-((3,4,5-trimethoxyphenyl)amino)-[1,2,4]triazolo[1,5-a]pyrazin-6-yl)-2H-pyrido[3,2-b][1,4]oxazin-3(4H)-one

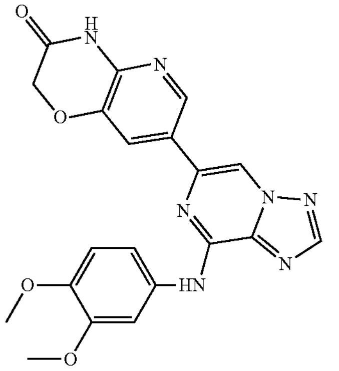

7-(8-((3,4-dimethoxyphenyl)amino)-[1,2,4]triazolo[1,5-a]pyrazin-6-yl)-2H-pyrido[3,2-b][1,4]oxazin-3(4H)-one -continued

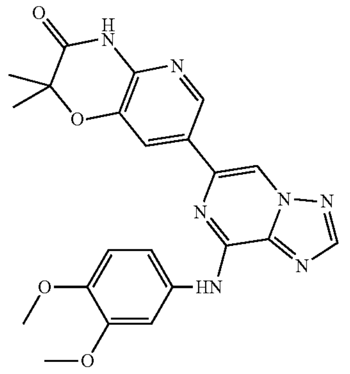

7-(8-((3,4-dimethoxyphenyl)amino)-[1,2,4]triazolo[1,5-a]pyrazin-6-yl)-2,2-dimethyl-2H-pyrido[3,2-b][1,4]oxazin-3(4H)-one

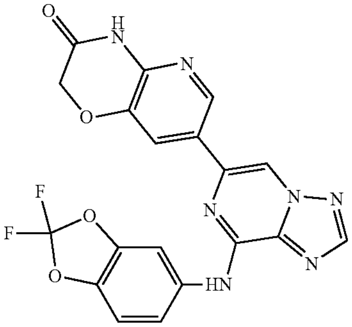

7-(8-((2,2-difluorobenzo[d][1,3]dioxol-5-yl)amino)-[1,2,4]triazolo[1,5-a]pyrazin-6-yl)-2H-pyrido[3,2-b][1,4]oxazin-3(4H)-one

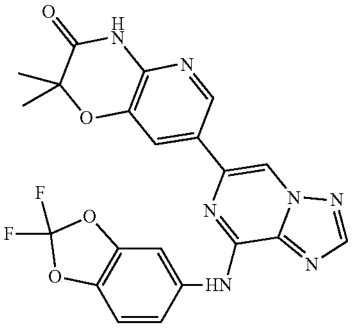

7-(8-((2,2-difluorobenzo[d][1,3]dioxol-5-yl)amino)-[1,2,4]triazolo[1,5-a]pyrazin-6-yl)-2,2-dimethyl-2H-pyrido[3,2-b][1,4]oxazin-3(4H)-one -continued

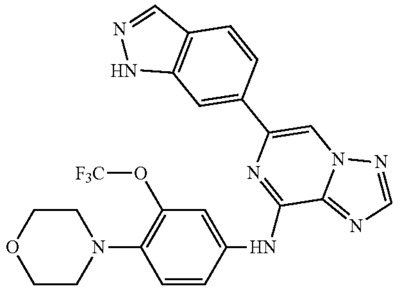

6-(1H-indazol-6-yl)-N-(4-morpholino-3-(trifluoromethoxy)phenyl)-[1,2,4]triazolo[1,5-a]pyrazin-8-amine

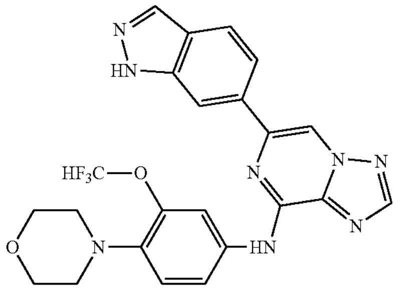

N-(3-(difluoromethoxy)-4-morpholinophenyl)-6-(1H-indazol-6-yl)-[1,2,4]triazolo[1,5-a]pyrazin-8-amine

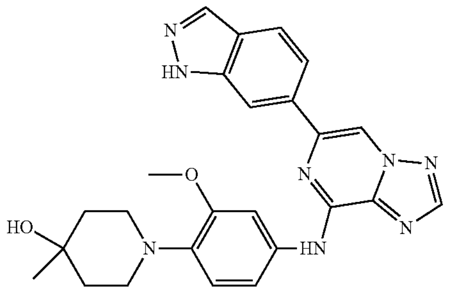

1-(4-((6-(1H-indazol-6-yl)-[1,2,4]triazolo[1,5-a]pyrazin-8-yl)amino)-2-methoxyphenyl)-4-methylpiperdin-4-ol

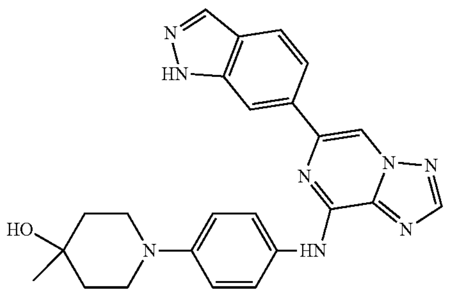

1-(4-((6-(1H-indazol-6-yl)-[1,2,4]triazolo[1,5-a]pyrazin-8-yl)amino)phenyl)-4-methylpiperdin-4-ol

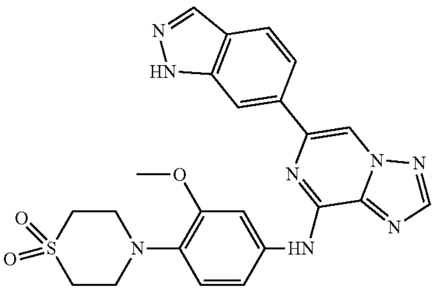

4-(4-((6-(1H-indazol-6-yl)-[1,2,4]triazolo[1,5-a]pyrazin-8-yl)amino)-2-methoxyphenyl)thiomorpholine 1,1-dioxide

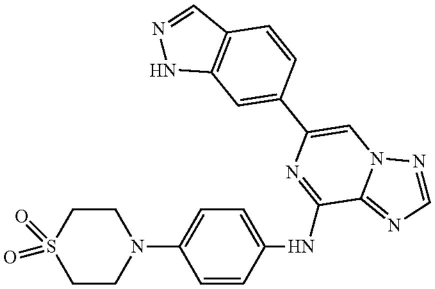

4-(4-((6-(1H-indazol-6-yl)-[1,2,4]triazolo[1,5-a]pyrazin-8-yl)amino)phenyl)thiomorpholine 1,1-dioxide

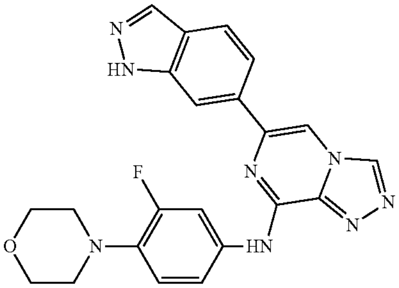

N-(3-fluoro-4-morpholinophenyl)-6-(1H-indazol-6-yl)-[1,2,4]triazolo[4,3-a]pyrazin-8-amine

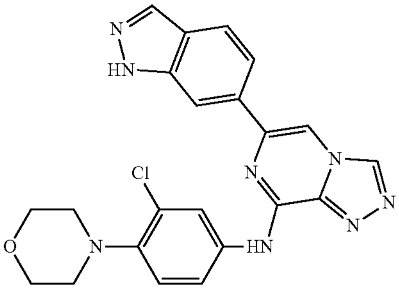

N-(3-chloro-4-morpholinophenyl)-6-(1H-indazol-6-yl)-[1,2,4]triazolo[4,3-a]pyrazin-8-amine

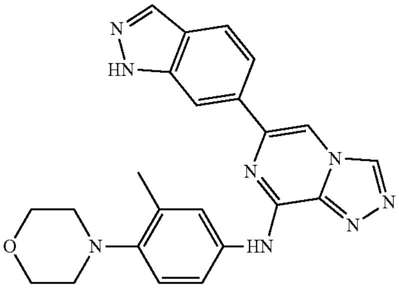

6-(1H-indazol-6-yl)-N-(3-methyl-4-morpholinophenyl)-[1,2,4]triazolo[4,3-a]pyrazin-8-amine

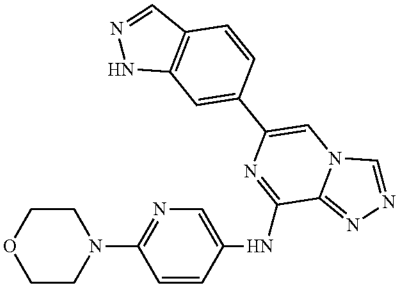

6-(1H-indazol-6-yl)-N-(6-morpholinopyridin)-3-yl)-[1,2,4]triazolo[4,3-a]pyrazin-8-amine

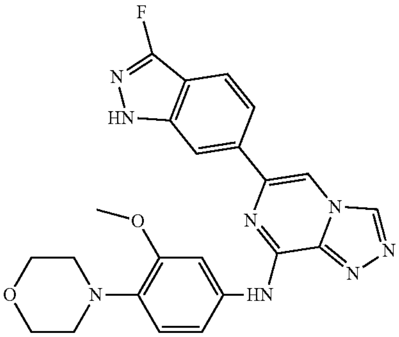

6-(3-fluoro-1H-indazol-6-yl)-N-(3-methoxy-4-morpholinophenyl)-[1,2,4]triazolo[4,3-a]pyrazin-8-amine -continued

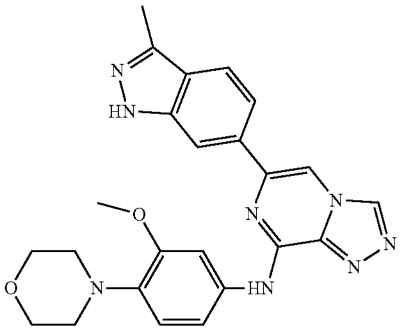

N-(3-methoxy-4-morpholinophenyl)-6-(3-methyl-1H-indazol-6-yl)-[1,2,4]triazolo[4,3-a]pyrazin-8-amine

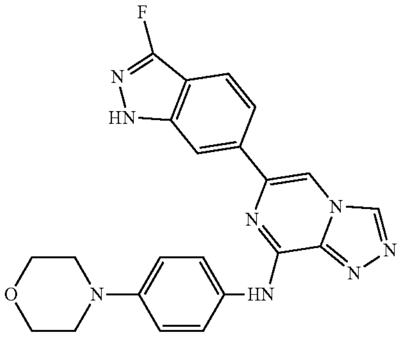

6-(3-fluoro-1H-indazol-6-yl)-N-(4-morpholinophenyl)-[1,2,4]triazolo[4,3-a]pyrazin-8-amine

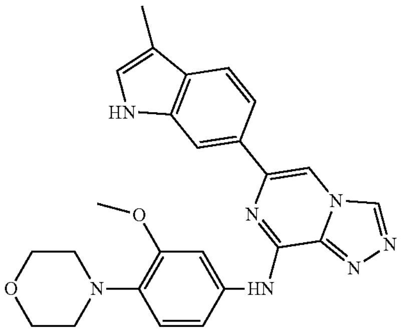

N-(3-methoxy-4-morpholinophenyl)-6-(3-methyl-1H-indazol-6-yl)-[1,2,4]triazolo[4,3-a]pyrazin-8-amine -continued

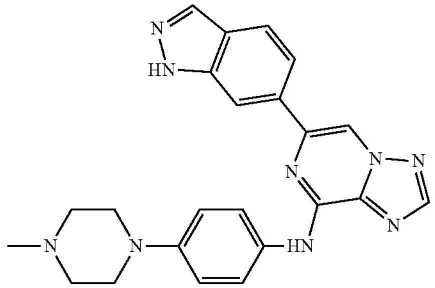

6-(1H-indazol-6-yl)-N-(4-(4-methylpiperazin-1-yl)phenyl)-[1,2,4]triazolo[4,3-a]pyrazin-8-amine

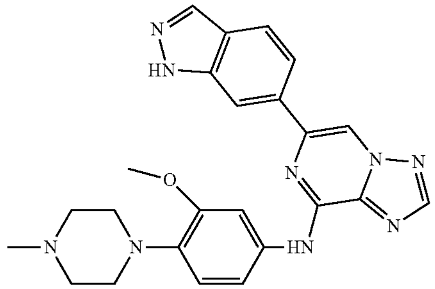

6-(1H-indazol-6-yl)-N-(3-methoxy-4-(4-methylpiperazin-1-yl)phenyl)-[1,2,4]triazolo[1,5-a]pyrazin-8-amine

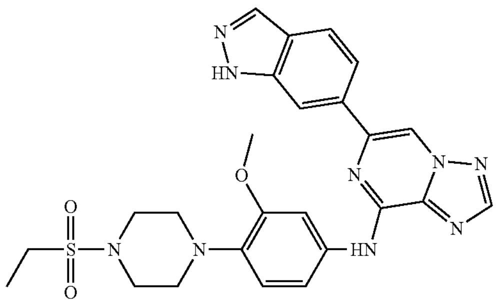

N-(4-(4-(ethysulfonyl)piperazin-1-yl)-3-methoxyphenyl)-6-(1H-indazol-6-yl)-[1,2,4]triazolo[1,5-a]pyrazin-8-amine

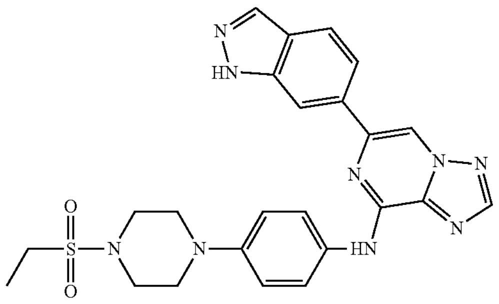

N-(4-(4-(ethysulfonyl)piperazin-1-yl)phenyl)-6-(1H-indazol-6-yl)-[1,2,4]triazolo[1,5-a]pyrazin-8-amine -continued

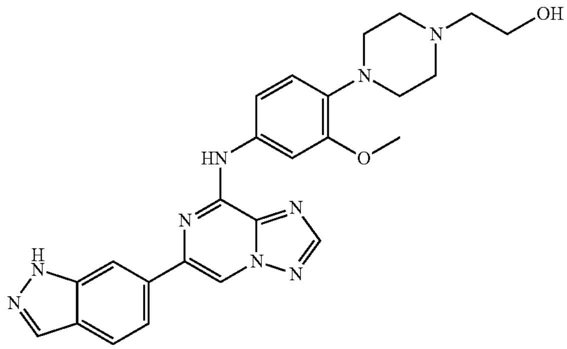

2-(4-(4-((6-(1H-indazol-6-yl)-[1,2,4]triazolo[1,5-a]pyrazin-8-yl)amino)-2-methoxyphenyl)piperazin-1-yl)ethan-1-ol

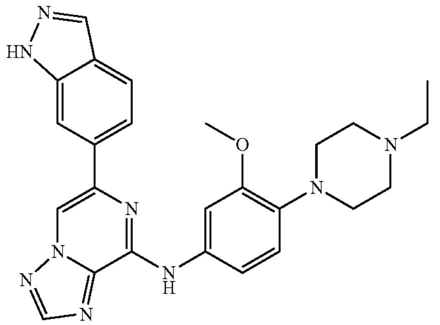

N-(4-(4-ethylpiperazin-1-yl)-3-methoxyphenyl)-6-(1H-indazol-6-yl)-[1,2,4]triazolo[1,5-a]pyrazin-8-amine

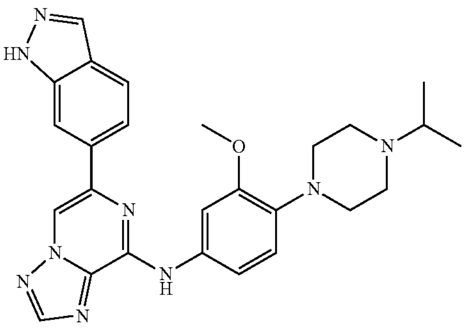

6-(1H-indazol-6-yl)-N-(4-(4-isopropylpiperazin-1-yl)-3-methoxyphenyl)-[1,2,4]triazolo[1,5-a]pyrazin-8-amine -continued

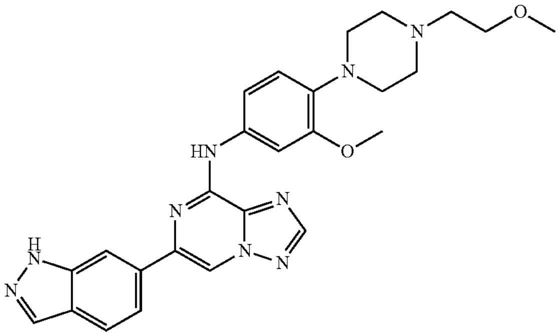

6-(1H-indazol-6-yl)-N-(3-methoxy-4-(4-(2-methoxyethyl)piperazin-1-yl)phenyl)-[1,2,4]triazolo[1,5-a]pyrazin-8-amine

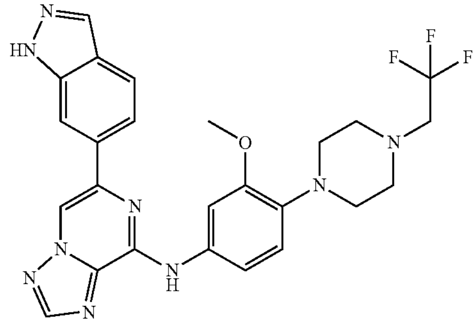

6-(1H-indazol-6-yl)-N-(3-methoxy-4-(4-(2,2,2-trifluoroethyl)piperazin-1-yl)phenyl)-[1,2,4]triazolo[1,5-a]pyrazin-8-amine

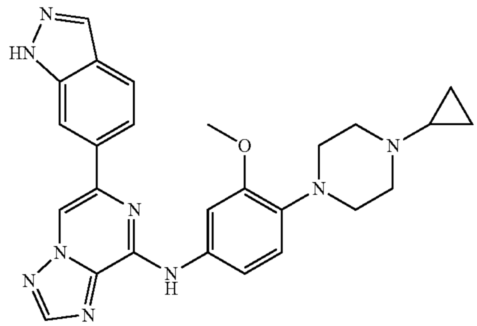

N-(4-(4-cyclopropylpiperazin-1-yl)-3-methoxyphenyl)-6-(1H-indazol-6-yl)-[1,2,4]triazolo[1,5-a]pyrazin-8-amine -continued

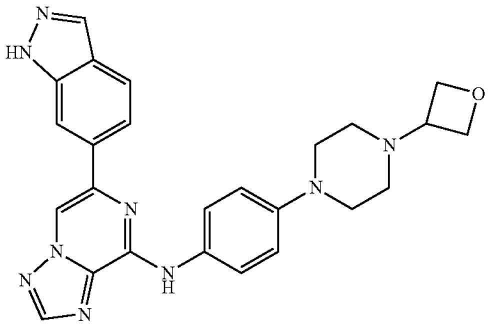

6-(1H-indazol-6-yl)-N-4-(4-(oxetan-3-yl)piperazin-1-yl)phenyl)-[1,2,4]triazolo[1,5-a]pyrazin-8-amine

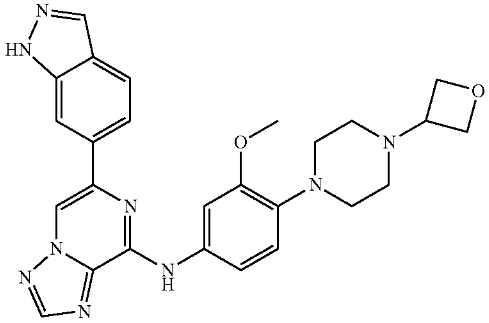

6-(1H-indazol-6-yl)-N-(3-methoxy-4-(4-(oxetan-3-yl)piperazin-1-yl)phenyl)-[1,2,4]triazolo[1,5-a]pyrazin-8-amine

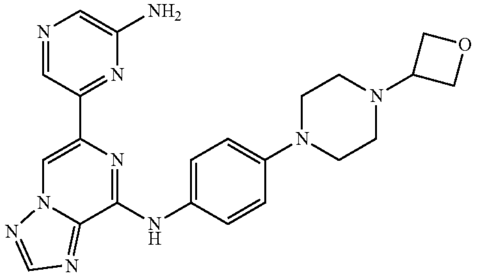

6-(6-aminopyrazin-2-yl)-N-(4-(4-(oxetan-3-yl)piperazin-1-yl)phenyl)-[1,2,4]triazolo[1,5-a]pyrazin-8-amine -continued

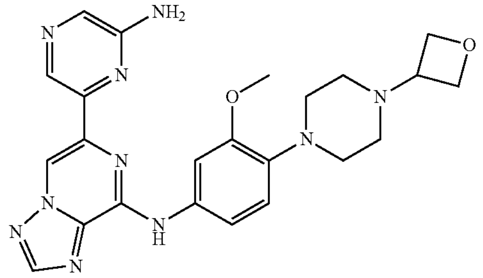

6-(6-aminopyrazin-2-yl)-N-(3-methoxy-4-(4-(oxetan-3-yl)piperazin-1-yl)phenyl)-[1,2,4]triazolo[1,5-a]pyrazin-8-amine

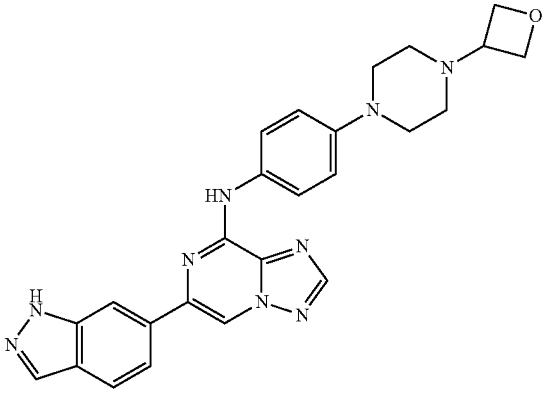

6-(1H-indazol-6-yl)-N-4-(4-(oxetan-3-yl)piperazin-1-yl)phenyl)-[1,2,4]triazolo[1,5-a]pyrazin-8-amine

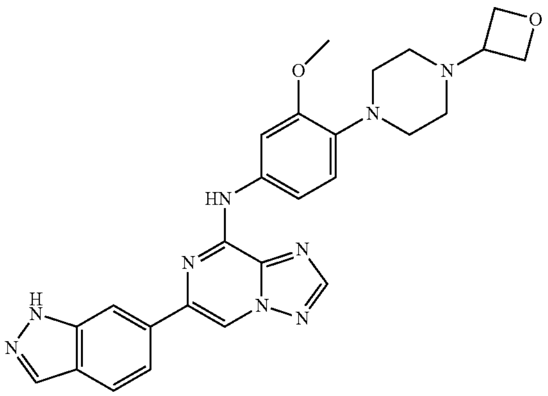

6-(1H-indazol-6-yl)-N-(3-methoxy-4-(4-(oxetan-3-yl)piperazin-1-yl)phenyl)-[1,2,4]triazolo[1,5-a]pyrazin-8-amine -continued

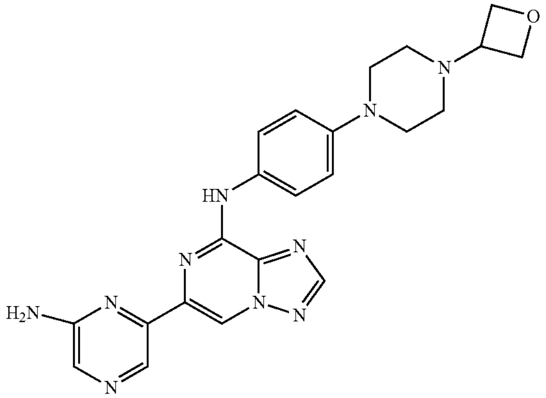

6-(6-aminopyrazin-2-yl)-N-(4-(4-(oxetan-3-yl)piperazin-1-yl)phenyl)-[1,2,4]triazolo[1,5-a]pyrazin-8-amine

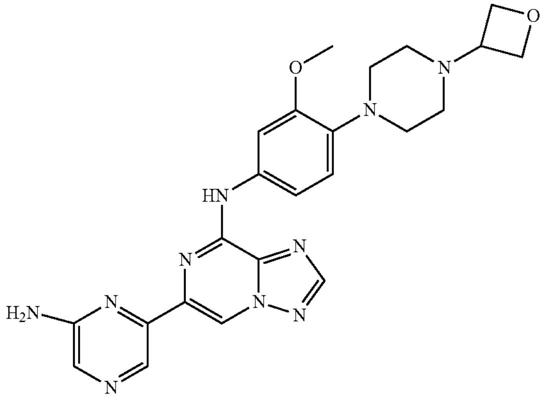

6-(6-aminopyrazin-2-yl)-N-(3-methoxy-4-(4-(oxetan-3-yl)piperazin-1-yl)phenyl)-[1,2,4]triazolo[1,5-a]pyrazin-8-amine

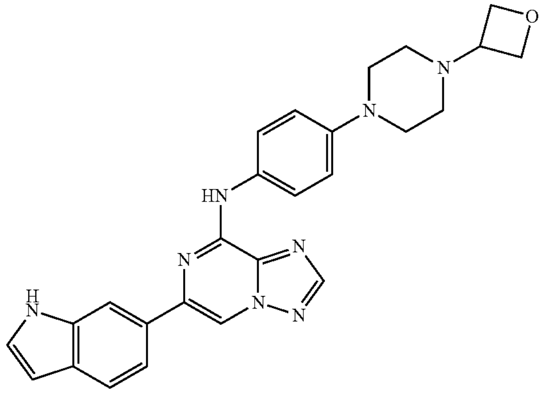

6-(1H-indol-6-yl)-N-(4-(4-(oxetan-3-yl)piperazin-1-yl)phenyl)-[1,2,4]triazolo[1,5-a]pyrazin-8-amine -continued

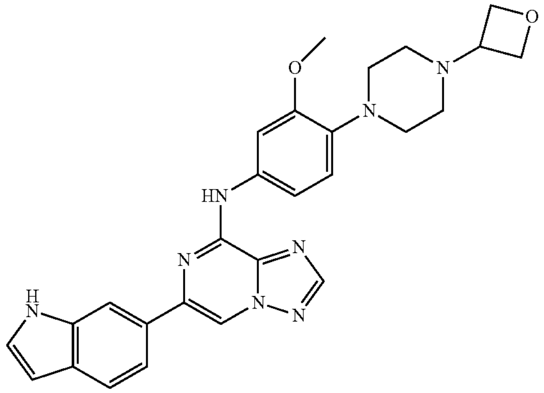

6-(1H-indol-6-yl)-N-(3-methoxy-4-(4-(oxetan-3-yl)piperazin-1-yl)phenyl)-[1,2,4]triazolo[1,5-a]pyrazin-8-amine

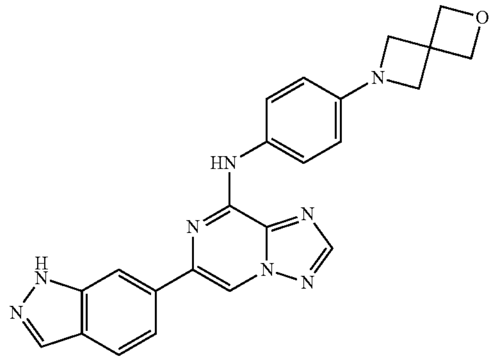

N-(4-(2-oxa-6-azaspiro[3.3]heptan-6-yl)phenyl)-6-(1H-indazol-6-yl)-[1,2,4]triazolo[1,5-a]pyrazin-8-amine

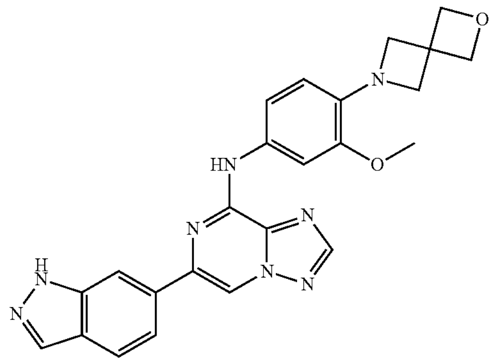

6-(1H-indazol-6-yl)-N-(3-methoxy-4-(2-oxa-6-azaspiro[3.3]heptan-6-yl)phenyl-[1,2,4]triazolo[1,5-a]pyrazin-8-amine -continued

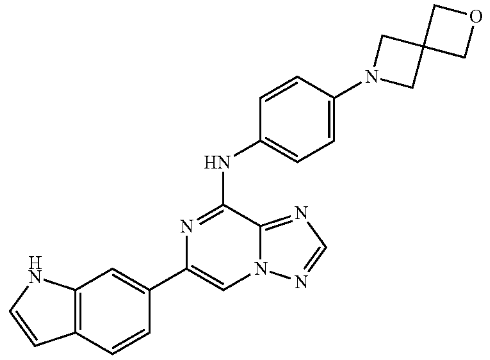

N-(4-(2-oxa-6-azaspiro[3.3]heptan-6-yl)phenyl)-6-(1H-indol-6-yl)-[1,2,4]triazolo[1,5-a]pyrazin-8-amine

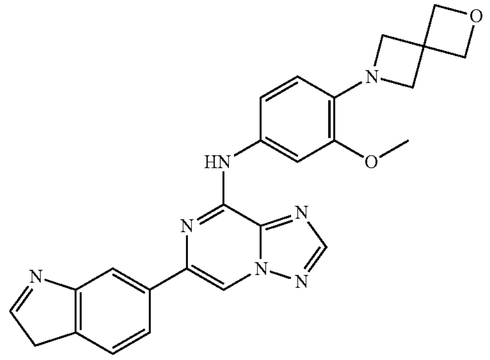

6-(3H-indol-6-yl)-N-(3-methoxy-4-(2-oxa-6-azaspiro[3.3]heptan-6-yl)phenyl-[1,2,4]triazolo[1,5-a]pyrazin-8-amine

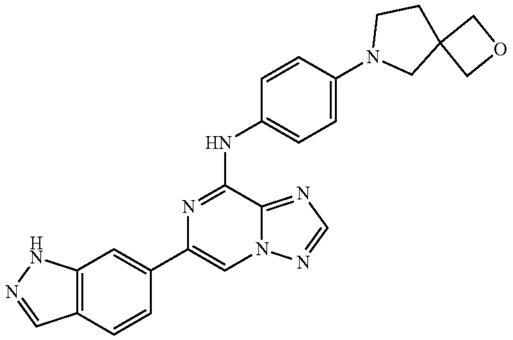

N-(4-(2-oxa-6-azaspiro[3.4]octan-6-yl)phenyl)-6-(1H-indazol-6-yl)-[1,2,4]triazolo[1,5-a]pyrazin-8-amine -continued

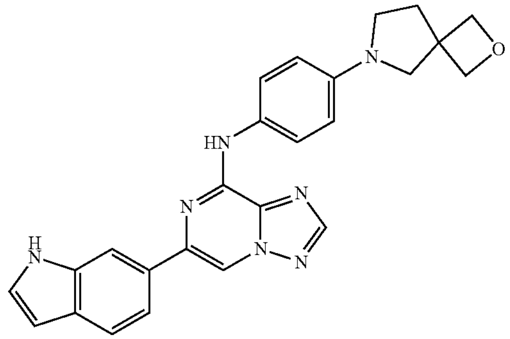

N-(4-(2-oxa-6-azaspiro[3.4]octan-6-yl)phenyl)-6-(1H-indazol-6-yl)-[1,2,4]triazolo[1,5-a]pyrazin-8-amine

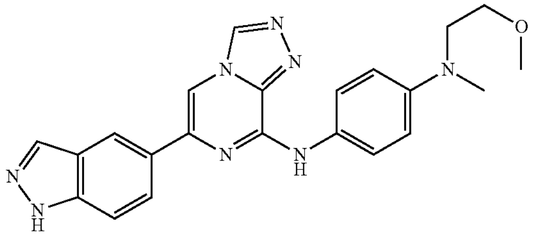

6-(1H-indazol-5-yl)-N-(4-morpholinophenyl)-[1,2,4]triazolo[1,5-a]pyrazin-8-amine

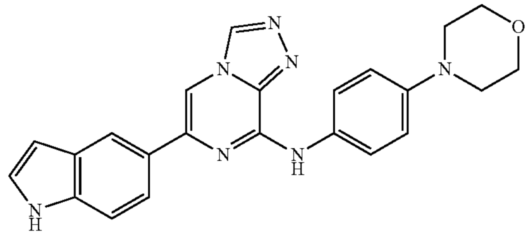

6-(1H-indazol-5-yl)-N-(4-morpholinophenyl)-[1,2,4]triazolo[1,5-a]pyrazin-8-amine

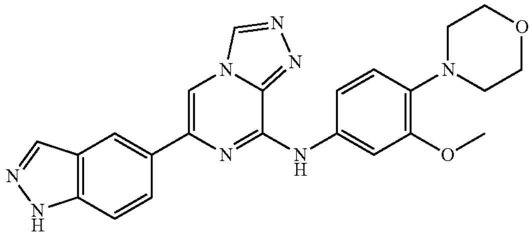

6-(1H-indazol-5-yl)-N-(3-methoxy-4-morpholinophenyl)-[1,2,4]triazolo[1,5-a]pyrazin-8-amine -continued

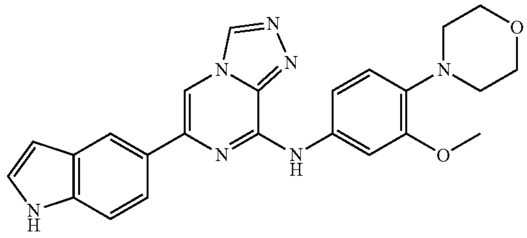

6-(1H-indol-5-yl)-N-(3-methoxy-4-morpholinophenyl)-[1,2,4]triazolo[1,5-a]pyrazin-8-amine

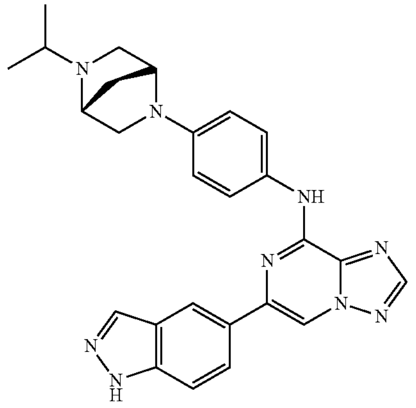

6-(1H-indazol-5-yl)-N-(4-((1S,4R)-isopropyl-2,5-diazabicyclo[2.2.1]heptan-2-yl)phenyl)-[1,2,4]triazolo[1,5-a]pyrazin-8-amine

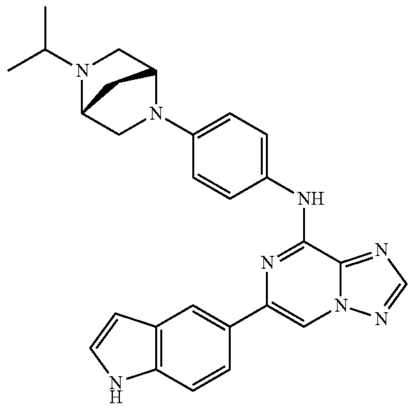

6-(1H-indol-5-yl)-N-(4-((1S,4R)-5-isopropyl-2,5-diazabicyclo[2.2.1]heptan-2-yl)phenyl)-[1,2,4]triazolo[1,5-a]pyrazin-8-amine -continued

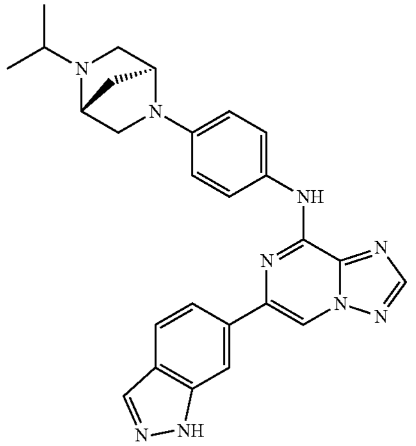

6-(1H-indazol-6-yl)-N-(4-((1S,4R)-5-isopropyl-2,5-diazabicyclo[2.2.1]heptan-2-yl)phenyl)-[1,2,4]triazolo[1,5-a]pyrazin-8-amine

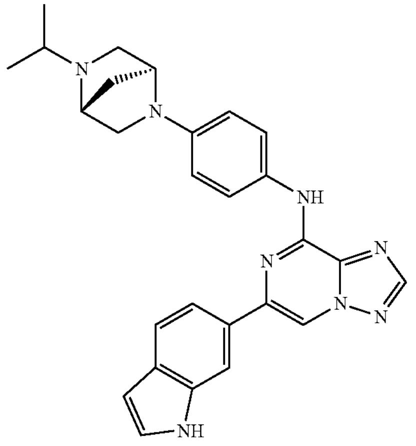

6-(1H-indol-6-yl)-N-(4-((1S,4R)-5-isopropyl-2,5-diazabicyclo[2.2.1]heptan-2-yl)phenyl)-[1,2,4]triazolo[1,5-a]pyrazin-8-amine

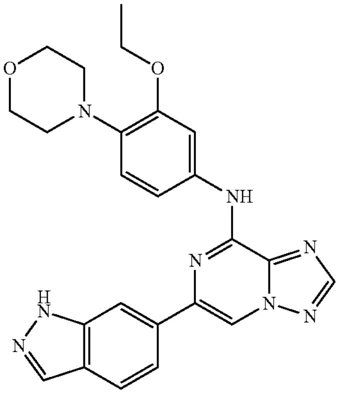

N-(3-ethoxy-4-morpholinophenyl)-6-(1H-indazol-6-yl)-[1,2,4]triazolo[1,5-a]pyrazin-8-amine -continued

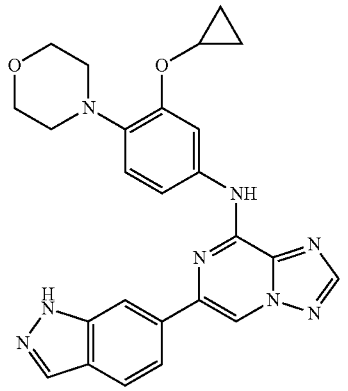

N-(3-cyclopropoxy-4-morpholinophenyl)-6-(1H-indazol-6-yl)-[1,2,4]triazolo[1,5-a]pyrazin-8-amine

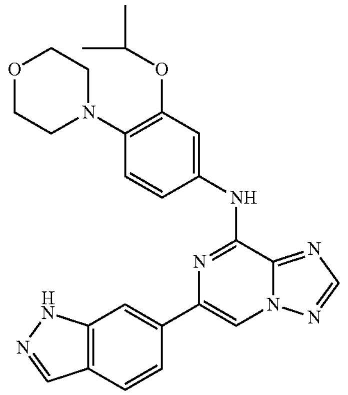

6-(1H-indazol-6-yl)-N-(3-isopropoxy-4-morpholinophenyl)-[1,2,4]triazolo[1,5-a]pyrazin-8-amine

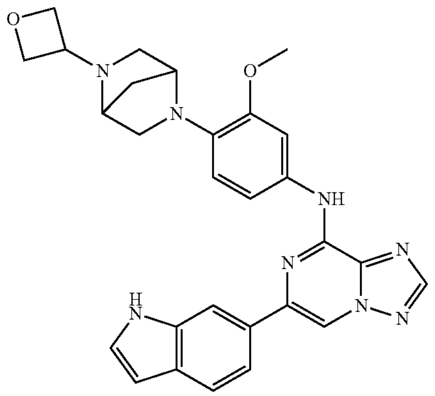

6-(1H-indol-6-yl)-N-(3-methoxy-4-(5-(oxetan-3-yl)-2,5-diazabicyclo[2.2.1]heptan-2-yl)phenyl)-[1,2,4]triazolo[1,5-a]pyrazin-8-amine -continued

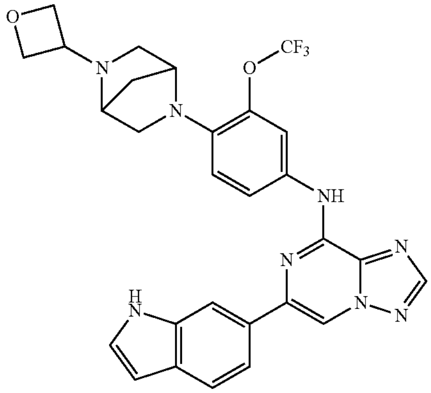

6-(1H-indol-6-yl)-N-4-(5-(oxetan-3-yl)-2,5-diazabicyclo[2.2.1]heptan-2-yl)-3-(trifluoromethoxy)phenyl)-[1,2,4]triazolo[1,5-a]pyrazin-8-amine

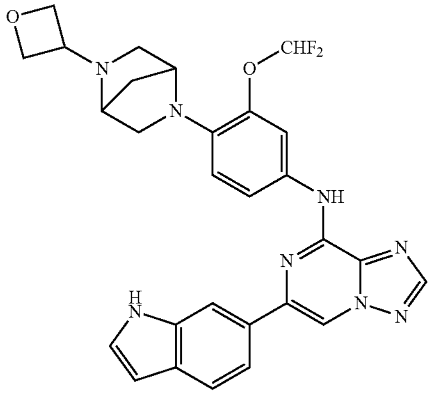

N-(3-(difluoromethoxy)-4-(5-(oxetan-3-yl)-2,5-diazabicyclo[2.2.1]heptan-2-yl)phenyl)-6-(1H-indol-6-yl)-[1,2,4]triazolo[1,5-a]pyrazin-8-amine

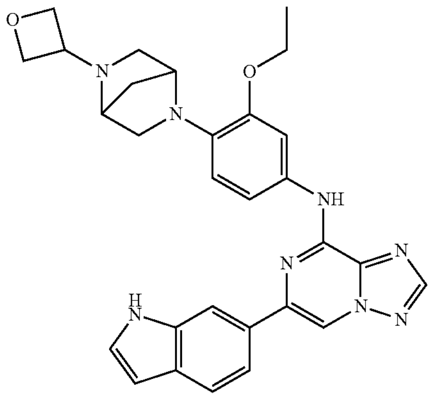

N-(3-ethoxy-4-(5-(oxetan-3-yl)-2,5-diazabicyclo[2.2.1]heptan-2-yl)phenyl-6-(1H-indol-6-yl)-[1,2,4]triazolo[1,5-a]pyrazin-8-amine -continued

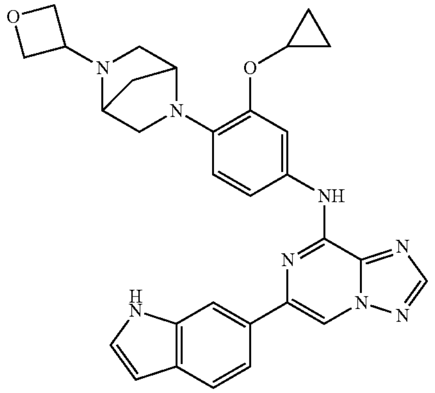

N-(3-cyclopropoxy-4-(5-(oxetan-3-yl)-2,5-diazabicyclo[2.2.1]heptan-2-yl)phenyl-6-(1H-indol-6-yl)-[1,2,4]triazolo[1,5-a]pyrazin-8-amine

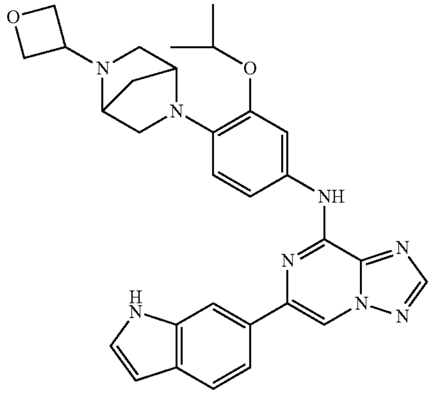

6-(1H-indol-6-yl)-N-(3-isopropoxy-4-(5-(oxetan-3-yl)-2,5-diazabicyclo[2.2.1]heptan-2-yl)phenyl-[1,2,4]triazolo[1,5-a]pyrazin-8-amine

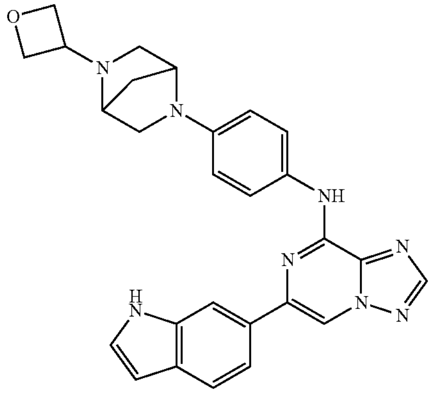

6-(1H-indol-6-yl)-N-4-(5-(oxetan-3-yl)-2,5-diazabicyclo[2.2.1]heptan-2-yl)phenyl-[1,2,4]triazolo[1,5-a]pyrazin-8-amine In some embodiments, the disclosure provides pharmaceutical compositions comprising a therapeutically effective amount of a compound of Formula I or a pharmaceutically acceptable salt, ester, stereoisomer, mixture of stereoisomers or tautomer thereof, and at least one pharmaceutically acceptable excipient.

In some embodiments, the invention provides a use of compounds, or a pharmaceutically acceptable salt or ester thereof described above for manufacture of a medicine for treating a disease or condition in a patient that is amenable to treatment by a Syk inhibitor. Such diseases and conditions include inflammatory disorders, allergic disorders, autoimmune diseases, or a cancer.

In some embodiments, the invention provides a method for treating a disease or condition selected from an inflammatory disorder, an allergic disorder, an autoimmune disease, or a cancer in a human in need thereof, comprising administering to the patient a therapeutic effective amount of a compound of a compound of Formula I, or a pharmaceutically acceptable salt thereof.

Conditions that may be treated with the compounds disclosed herein include, but are not limited to, lymphoma, multiple myeloma, and leukemia. Additional diseases or conditions that may be treated include, but are not limited to acute lymphocytic leukemia (ALL), acute myeloid leukemia (AML), chronic lymphocytic leukemia (CLL), small lymphocytic lymphoma (SLL), myelodysplastic syndrome (MDS), myeloproliferative disease (MPD), chronic myeloid leukemia (CML), multiple myeloma (MM), non-Hodgkin's lymphoma (NHL), mantle cell lymphoma (MCL), follicular lymphoma, Waldestrom's macroglobulinemia (WM), T-cell lymphoma, B-cell lymphoma, diffuse large B-cell lymphoma (DLBCL), pancreatic cancer, bladder cancer, colorectal cancer, breast cancer, prostate cancer, renal cancer, hepatocellular cancer, lung cancer, ovarian cancer, cervical cancer, gastric cancer, esophageal cancer, head and neck cancer, melanoma, neuroendocrine cancer, CNS cancer, brain cancer, bone cancer, soft tissue sarcoma, non-small cell lung cancer, small-cell lung cancer, colon cancer, systemic lupus erythematosus (SLE), myestenia gravis, rheumatoid arthritis (RA), acute disseminated encephalomyelitis, idiopathic thrombocytopeniarpura, multiple sclerosis (MS), Sjoegren's syndrome, autoimmune hemolytic anemia, asthma, lupus, psoriasis, ulcerative colitis, Crohn's disease, irritable bowel syndrome, dermatomyositis. Additional diseases or conditions that may be treated include, but are not limited to, arterial thrombosis, thromboinflammatory, hematological malignancies.

BRIEF DESCRIPTION OF THE SEVERAL VIEWS OF THE DRAWING(S)

Not Applicable.

DETAILED DESCRIPTION OF THE INVENTION

Definitions

In this invention, the following definitions are applicable:

"Alkyl" refers to a monoradical unbranched or branched saturated hydrocarbon chain. In some embodiments, alkyl as used herein has 1 to 20 carbon atoms (i.e., $C_{1-20}$ alkyl), 1 to 6 carbon atoms (i.e., $C_{1-6}$ alkyl). Examples of alkyl groups include methyl, ethyl, propyl, isopropyl, n-butyl, sec-butyl, tert-butyl, pentyl, 2-pentyl, isopentyl, neopentyl, hexyl, 2-hexyl, 3-hexyl, and 3-methylpentyl. When an alkyl residue having a specific number of carbons is named, all geometric isomers having that number of carbons may be encompassed; thus, for example, "butyl" can include n-butyl, sec-butyl, isobutyl, and t-butyl; "propyl" can include n-propyl and isopropyl. In some embodiments, "lower alkyl" refers to alkyl groups having 1 to 6 carbons (i.e., $C_{1-6}$ alkyl).

The term "alkylene" refers to a diradical of a branched or unbranched saturated hydrocarbon chain, in some embodiments, having from 1 to 20 carbon atoms (e.g., 1-10 carbon atoms or 1, 2, 3, 4, 5 or 6 carbon atoms). This term is exemplified by groups such as methylene ($—CH_2—$), ethylene ($—CH_2CH_2—$), the propylene isomers (e.g., $—CH_2CH_2CH_2—$ and $—CH(CH_3)CH_2—$), and the like.

The term "alkynyl" refers to a monoradical of an unsaturated hydrocarbon, in some embodiments, having from 2 to 20 carbon atoms (in some embodiments, from 2 to 10 carbon atoms, e.g., 2 to 6 carbon atoms) and having from 1 to 6 carbon-carbon triple bonds e.g., 1, 2 or 3 carbon-carbon triple bonds. In some embodiments, alkynyl groups include ethynyl (—C≡CH), propargyl (or propynyl, i.e. $—C≡CCH_3$), and the like.

The term "alkoxy" refers to the group R—O—, where R is alkyl or —Y—Z, in which Y is alkylene and Z is alkenyl or alkynyl, where alkyl, alkenyl and alkynyl are as defined herein. In some embodiments, alkoxy groups are alkyl-O— and includes, by way of example, methoxy, ethoxy, n-propoxy, iso-propoxy, n-butoxy, tert-butoxy, sec-butoxy, n-pentoxy, n-hexyloxy, 1,2-dimethylbutoxy, and the like.

The term "cycloalkyl" refers to a saturated or partially unsaturated cyclic alkyl group. In some embodiments, cycloalkyl as used herein has from 3 to 20 ring carbon atoms (i.e., $C_{3-20}$ cycloalkyl), or 3 to 12 ring carbon atoms (i.e., $C_{3-12}$ cycloalkyl), or 3 to 8 ring carbon atoms (i.e., $C_{3-8}$ cycloalkyl). Examples of cycloalkyl groups include cyclopropyl, cyclobutyl, cyclopentyl, cyclohexyl and cyclohexeny.

The term "keto" or "oxo" refers to a group =O.

The term "carboxy" refers to a group —C(O)—OH.

The term "aminocarbonyl" refers to the group —C(O)NHR where R is independently hydrogen, alkyl, alkenyl, alkynyl, or benzoyloxy.

The term "halogen" or "halo" refers to fluoro, bromo, chloro and iodo and the term "halogen" includes fluorine, chlorine, bromine, and iodine. "Haloalkyl" refers to an unbranched or branched chain alkyl group as defined above, wherein one or more hydrogen atoms are replaced by a halogen. One example of a haloalkyl is "fluoroalkyl" which includes, as examples, fluoromethyl, fluoroethyl, fluoropropyl, difluoromethyl, difluoroethyl, difluoropropyl, trifluoromethyl, trifluoroethyl, and trifluoropropyl groups. "Haloalkoxy" refers to an unbranched or branched chain alkyl group as defined above, wherein one or more hydrogen atoms are replaced by a halogen. One example of a haloalkoxy is "fluoroalkoxy" which includes, as examples, fluoromethoxy, fluoroethoxy, fluoropropoxy, difluoromethoxy, difluoroethoxy, difluoropropoxy, trifluoromethoxy, trifluoroethoxy and trifluoropropoxy.

"Optional" or "optionally" means that the subsequently described event or circumstance may or may not occur, and that the description includes instances where said event or circumstance occurs and instances in which it does not.

A "substituted" group includes embodiments in which a monoradical substituent is bound to a single atom of the substituted group (e.g., forming a branch), and also includes embodiments in which the substituent may be a diradical bridging group bound to two adjacent atoms of the substituted group, thereby forming a fused ring on the substituted group.

Where a given group (moiety) is described herein as being attached to a second group and the site of attachment is not explicit, the given group may be attached at any available site of the given group to any available site of the second group. For example, a "lower alkyl-substituted phenyl", where the attachment sites are not explicit, may have any available site of the lower alkyl group attached to any available site of the phenyl group. In this regard, an "available site" is a site of the group at which a hydrogen of the group may be replaced with a substituent.

A therapeutically effective amount is an amount of a compound of Formula (I) or a combination of two or more such compounds, which inhibits, totally or partially, the progression of the condition or alleviates, at least partially, ore or more symptoms of the condition A therapeutically effective amount can also be an amount which is prophylactically effective. The amount which is therapeutically effective will depend upon the patient's sex and gender, the condition to be treated, the severity of the condition and the result sought. For a given patient, a therapeutically effective amount can be determined by methods known to those of skill in the art.

A compound of a given formula (e.g., the compound of Formula I, which also includes compounds of all other Formulas herein) is intended to encompass the compounds of the disclosure, and the pharmaceutically acceptable salts, pharmaceutically acceptable esters, isomers, tautomers, solvates, isotopes, hydrates, polymorphs, and prodrugs of such compounds. Additionally, the compounds of the disclosure may possess one or more asymmetric centers, and can be produced as a racemic mixture or as individual enantiomers or diastereoisomers. The number of stereoisomers present in any given compound of a given formula depends upon the number of asymmetric centers present (there are $2^n$ stereoisomers possible where n is the number of asymmetric centers). The individual stereoisomers may be obtained by resolving a racemic or non-racemic mixture of an intermediate at some appropriate stage of the synthesis or by resolution of the compound by conventional means.

'Pharmaceutically acceptable salts" refers to those salts which retain the biological effectiveness and properties of the free bases and which are obtained by reaction with inorganic acids, for example, acid, hydrobromic acid, sulfuric acid, nitric acid, and phosphoric acid or organic acids such as sulfonic acid, carboxylic acid, organic phosphoric acid, methanesulfonic acid, ethanesulfonic acid, toluenesulfonic acid, citric acid, fumaric acid, maleic acid, succinic acid, benzoic acid, salicylic acid, lactic acid, tartaric acid (e.g., (+) or (−)-tartaric acid or mixtures thereof), amino acids (e.g., (+) or (−)-amino acids or mixtures thereof), and the like. These salts can be prepared by methods known to those skilled in the art. "Pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio.

Pharmaceutically acceptable salts are well known in the art. For example, S. M. Berge et al., describe pharmaceutically acceptable salts in detail in J. Pharmaceutical Sciences, 1977, 66, 1-19, incorporated herein by reference.

Certain compounds of Formula (I) which have acidic substituents may exist as salts with pharmaceutically acceptable bas s. The present invention includes such salts. Salts derived from inorganic bases include, by way of example only, sodium, potassium, lithium, ammonium, calcium, and magnesium salts. Salts derived from organic bases include, but are not limited to, salts of primary, secondary, and tertiary amines. Specific examples of suitable amines include, by way of example only, isopropylamine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like. These salts maybe prepared by methods known to those skilled in the art.

The individual stereoisomers (including individual enantiomers and diastereoisomers) as well as racemic and non-racemic mixtures of stereoisomers are encompassed within the scope of the present disclosure, all of which are intended to be depicted by the structures of this specification unless otherwise specifically indicated.

"Isomers" are different compounds that have the same molecular formula. Isomers include stereoisomers, enantiomers and diastereomers.

"Stereoisomers" are isomers that differ only in the way the atoms are arranged in space.

"Enantiomers" are a pair of stereoisomers that are non-superimposable mirror images of each other. A 1:1 mixture of a pair of enantiomers is a "racemic" mixture. The term "(±)" is used to designate a racemic mixture where appropriate.

"Diastereoisomers" are stereoisomers that have at least two asymmetric atoms, but which are not mirror-images of each other.

Some of the compounds exist as tautomeric isomers. Tautomeric isomers are in equilibrium with one another. For example, amide containing compounds may exist in equilibrium with imidic acid tautomers. Regardless of which tautomer is shown, and regardless of the nature of the equilibrium among tautomers, the compounds are understood by one of ordinary skill in the art to comprise both amide and imidic acid tautomers. Thus, the amide containing compounds are understood to include their imidic acid tautomers. Likewise, the imidic acid containing compounds are understood to include their amide tautomers.

The term "polymorph" refers to different crystal structures of a crystalline compound. The different polymorphs may result from differences in crystal packing (packing polymorphism) or differences in packing between different conformers of the same molecule (conformational polymorphism).

The term "solvate" refers to a complex formed by the combining of a compound of the present invention and a solvent.

The term "hydrate" refers to the complex formed by the combining of a compound of the present invention and water. The term "prodrug" refers to compounds of the present invention that include chemical groups which, in vivo, can be converted and/or can be split off from the remainder of the molecule to provide for the active drug, a pharmaceutically acceptable salt thereof or a biologically active metabolite thereof.

The term "inhibition" indicates a significant decrease in the baseline activity of a biological activity or process. "Inhibition of Syk activity" refers to a decrease in Syk activity as a direct or indirect response to the presence of a compound of the present invention, or a pharmaceutically acceptable salt thereof, relative to the activity of Syk in the absence of the compound. The decrease in activity may be due to the direct interaction of the compound with Syk, or due to the interaction of the chemical entity(ies) described herein with one or more other factors that in turn affect Syk activity. For example, the presence of the chemical entity (ies) may decrease Syk activity by directly binding to the Syk, by causing (directly or indirectly) another factor to decrease Syk activity, or by (directly or indirectly) decreasing the amount of Syk present in the cell or organism.

An "allergy" or "allergic disorder" refers to acquired hypersensitivity to a substance (allergen). Allergic conditions include eczema, allergic rhinitis or coryza, hay fever, bronchial asthma, urticaria (hives) and food allergies, and other atopic conditions. Food allergies include pollen allergies, dairy allergies, including milk allergies, soy allergies, egg allergies, wheat allergies, nut allergies, including allergies to peanuts and tree nuts (walnuts, almonds, hazelnuts, cashews, pistachios, pecans, Brazil nuts, beechnuts, butternuts, chestnuts, Chinquapin nuts, hickory nuts, etc.) and seafood allergies.

"Asthma" refers to a disorder of the respiratory system characterized by inflammation, narrowing of the airways and increased reactivity of the airways to inhaled agents. Asthma is frequently, although not exclusively associated with atopic or allergic symptoms.

"Patient" refers to an animal, such as a mammal, that has been or will be the object of treatment, observation, or experiment. The methods described herein may be useful in both human therapy and veterinary applications. In some embodiments, the patient is a mammal; in some embodiments the patient is human; and in some embodiments the patient is chosen from cats and dogs.

The term "treatment" or "treating" means administration of a compound of the invention, by or at the direction of a competent caregiver, to a mammal having a disease for purposes including: (i) preventing the disease, that is, causing the clinical symptoms of the disease not to develop; (ii) inhibiting the disease, that is, arresting the development of clinical symptoms; and/or (iii) relieving the disease, that is, causing the regression of clinical symptoms.

Pharmaceutical Compositions and Administration

Compounds of the present invention, or a pharmaceutically acceptable salt thereof, are usually administered in the form of pharmaceutical compositions. This disclosure therefore provides pharmaceutical compositions that contain, as the active ingredient, one or more of the compounds described, or a pharmaceutically acceptable salt or ester thereof, and one or more pharmaceutically acceptable excipients, carriers, including inert solid diluents and fillers, diluents, including sterile aqueous solution and various organic solvents, permeation enhancers, solubilizers and adjuvants. The pharmaceutical compositions may be administered alone or in combination with other therapeutic agents. Such compositions are prepared in a manner well known in the pharmaceutical art (see, e.g., Remington's Pharmaceutical Sciences, Mace Publishing Co., Philadelphia, PA 17th Ed. (1985); and Modern Pharmaceutics, Marcel Dekker, Inc. 3rd Ed. (G. S. Banker & C. T. Rhodes, Eds.)

The pharmaceutical compositions may be administered in either single or multiple doses by any of the accepted modes of administration of agents having similar utilities, for example as described in those patents and patent applications incorporated by reference, including rectal, buccal, intranasal and transdermal routes, by intraarterial injection, intravenously, intraperitoneally, parenterally, intramuscularly, subcutaneously, orally, topically, as an inhalant, or via an impregnated or coated device such as a stent, for example, or an artery-inserted cylindrical polymer.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl and propylhydroxy-benzoates; sweetening agents; and flavoring agents.

The compositions are preferably formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient (e.g., a tablet, capsule, ampoule). The compounds are generally administered in a pharmaceutically effective amount. Preferably, for oral administration, each dosage unit contains from 1 mg to 2 g, or alternatively, or 100 mg to 500 mg, of a compound of the present invention, or a pharmaceutically acceptable salt thereof, and for parenteral administration, preferably from 0.1 mg to 700 mg, or alternatively, 0.1 mg to 100 mg, of a compound a compound of the present invention, or a pharmaceutically acceptable salt thereof. It will be understood, however, that the amount of the compound actually administered usually will be determined by a physician, in the light of the relevant circumstances, including the condition to be treated, the chosen route of administration, the actual compound administered and its relative activity, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present disclosure. When referring to these preformulation compositions as homogeneous, it is meant that the active ingredient is dispersed evenly throughout the composition so that the Composition may be readily subdivided into equally effective unit dosage forms such as tablets, pills, and capsules. The tablets or pills of the present disclosure may be coated or otherwise compounded to provide a dosage form affording the advantage of prolonged action, or to protect from the acid conditions of the stomach. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid or solid compositions comprising a compound of the present invention, or a pharmaceutically acceptable salt thereof may contain suitable pharmaceutically acceptable excipients as described supra. Preferably, the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Kits comprising a pharmaceutical composition comprising a compound of the present invention, or a pharmaceutically acceptable salt thereof, and at least one pharmaceutically acceptable carrier is also provided. In some embodiments, the kit comprises instructions for use in the treatment of cancer or inflammatory conditions. In a particular variation, the instructions are directed to use of the pharmaceutical composition for the treatment of cancer, including for example, leukemia or lymphoma. In specific embodiments, the cancer is ALL, AML, CLL, SLL, MDS, MPD, CML, MM, iNHL, refractory iNHL, NHL, MCL, follicular lymphoma, WM, T-cell lymphoma, B-cell lymphoma, and DLBCL. In one embodiment, the cancer is T-cell acute lymphoblastic leukemia (T-ALL), or B-cell acute lymphoblastic leukemia (B-ALL).

In a particular variation, the instructions are directed to use of the pharmaceutical composition for the treatment of an autoimmune disease. Specific embodiments of an autoimmune disease include asthma, rheumatoid arthritis, multiple sclerosis, and lupus.

Any pharmaceutical composition provided in the present disclosure may be used in the kits, the same as if each and every composition were specifically and individually listed for use a kit.

Uses of Compounds and Compositions Thereof

Provided is a method of treating a patient, for example, a mammal, such as a human, having a disease responsive to inhibition of Syk activity, comprising administrating to the patient having such a disease, an effective amount of a compound of the present invention, or a pharmaceutically acceptable salt thereof.

In some embodiments, the compounds of the present invention, or a pharmaceutically acceptable salt thereof, may also inhibit other kinases, such that disease, disease symptoms, and conditions associated with these kinases is also treated.

Methods of treatment also include inhibiting Syk activity and/or inhibiting B-cell activity, by inhibiting ATP binding or hydrolysis by Syk or by some other mechanism, in vivo, in a patient suffering from a disease responsive to inhibition of Syk activity, by administering an effective concentration of a compound of the present invention, or a pharmaceutically acceptable salt thereof. An example of an effective concentration would be that concentration sufficient to inhibit Syk activity in vitro. An effective concentration may be ascertained experimentally, for example by assaying blood concentration of the chemical entity, or theoretically, by calculating bioavailability.

In some embodiments, the condition responsive to inhibition of Syk activity and/or B-cell activity is cancer, an allergic disorder and/or an autoimmune and/or inflammatory disease, and/or an acute inflammatory reaction.

Also provided is a method of treating a patient having cancer, an allergic disorder and/or an autoimmune and/or inflammatory disease, and/or an acute inflammatory reaction, by administering an effective amount of a compound of the present invention, or a pharmaceutically acceptable salt thereof.

In some embodiments, the conditions and diseases that can be affected using a compound of the present invention, or a pharmaceutically acceptable salt thereof, include, but are not limited to: allergic disorders, including but not limited to eczema, allergic rhinitis or coryza, hay fever, bronchial asthma, urticaria (hives) and food allergies (including pollen allergies, dairy allergies, including milk allergies, soy allergies, egg allergies, wheat allergies, nut allergies, and seafood allergies), and other atopic conditions; autoimmune and/or inflammatory diseases, including but not limited to psoriasis, Crohn's disease, irritable bowel syndrome, Sjogren's disease, tissue graft rejection, and hyperacute rejection of transplanted organs, asthma, systemic lupus erythematosus (and associated glomerulonephritis), dermatomyositis, multiple sclerosis, scleroderma, vasculitis (ANCA-associated and other vasculitides), autoimmune hemolytic and thrombocytopeniatates, Goodpasture's syndrome (and associated glomerulonephritis and pulmonary hemorrhage), atherosclerosis, rheumatoid arthritis, chronic Idiopathic thrombocytopenia purpura (ITP), Addison's disease, Parkinson's disease, Alzheimer's disease, diabetes, septic shock, myasthenia gravis, and the like; acute inflammatory reactions, including but not limited to skin sunburn, inflammatory pelvic disease, inflammatory bowel disease, urethritis, uvitis, sinusitis, pneumonitis, encephalitis, meningitis, myocarditis, nephritis, osteomyelitis, myositis, hepatitis, gastritis, enteritis, dermatitis, gingivitis, appendicitis, pancreatitis, and cholocystitis; polycystic kidney disease, and cancer, including but not limited to, B-cell lymphoma, lymphoma (including Hodgkin's and non-Hodgkins lymphoma), hairy cell leukemia, multiple myeloma, chronic and acute myelogenous leukemia, and chronic and acute lymphocytic leukemia.

Syk is a known inhibitor of apoptosis in lymphoma B-cells. Defective apoptosis contributes to the pathogenesis and drug resistance of human leukemias and lymphomas. Thus, further provided is a method of promoting or inducing apoptosis in cells expressing Syk comprising contacting the cell with a compound of the present invention, or a pharmaceutically acceptable salt thereof.

In some embodiments, provided is a method of treating a patient having cancer by administering an effective amount of a compound of the present invention, or a pharmaceutically acceptable salt thereof. In particular embodiments, the cancer is leukemia or lymphoma. In specific embodiments, the cancer is ALL, AML, CLL, SLL, MDS, MPD, CML, MM, iNHL, refractory iNHL, NHL, MCL, follicular lymphoma, WM, T-cell lymphoma, B-cell lymphoma, and DLBCL. In one embodiment, the cancer is T-ALL or B-ALL. The non-Hodgkin lymphoma encompasses the indolent B-cell diseases that include, for example, follicular lymphoma, lymphoplasmacytic lymphoma, Waldenstrom macroglobulinemia, and marginal zone lymphoma, as well as the aggressive lymphomas that include, for example, Burkitt lymphoma, DLBCL and MCL.

In some embodiments, provided is a method of treating a patient having a hematologic malignancy by administering an effective amount of a compound of the present invention, or a pharmaceutically acceptable salt thereof. In specific embodiments, the hematologic malignancy is leukemia (e.g., chronic lymphocytic leukemia) or lymphoma (e.g., non-Hodgkin's lymphoma).

Dosage levels of the order, for example, of from 0.1 mg to 140 mg per kilogram of body weight per day can be useful in the treatment of the above-indicated conditions (0.5 mg to 7 g per patient per day). The amount of active ingredient that may be combined with the vehicle to produce a single dosage form will vary depending upon the host treated and the particular mode of administration. Dosage unit forms will generally contain from 1 mg to 500 mg of an active ingredient.

Frequency of dosage may also vary depending on the compound used and the particular disease treated. In some embodiments, for example, for the treatment of an allergic disorder and/or autoimmune and/or inflammatory disease, a dosage regimen of 4 times daily or less is used. In some embodiments, a dosage regimen of 1 or 2 times daily is used. It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease in the patient undergoing therapy.

The compounds of the disclosure may be prepared using methods disclosed herein and routine modifications thereof which will be apparent given the disclosure herein and methods well known in the art. Conventional and well-known synthetic methods may be used in addition to the teachings herein. The synthesis of typical compounds of the present invention, or a pharmaceutically acceptable salt thereof, e.g., compounds having one or more of structures described by the present invention, or other formulas or compounds disclosed herein, may be accomplished as described in the following examples. If available, reagents may be purchased commercially, e.g., from Sigma Aldrich or other chemical suppliers.

General Syntheses

Typical embodiments of compounds in accordance with the present disclosure may be synthesized using the general reaction schemes described below. It will be apparent given the description herein that the general schemes may be altered by substitution of the starting materials with other materials having similar structures to result in products that are correspondingly different. Descriptions of syntheses follow to provide numerous examples of how the starting materials may vary to provide corresponding products. Starting materials are typically obtained from commercial sources or synthesized using published methods. Compounds of the present invention can be prepared beginning with commercially starting materials and utilizing general synthetic techniques and procedures known to those skilled in the art. Outlined below are reaction schemes suitable for preparing such compounds. Further exemplification is found in the specific Examples detailed below.

General method A

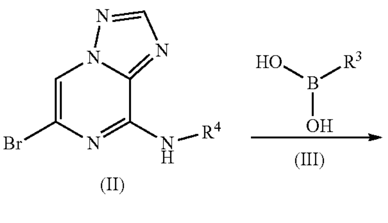

-continued

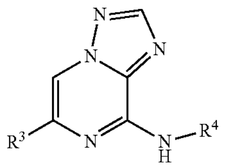

(I)

General method B

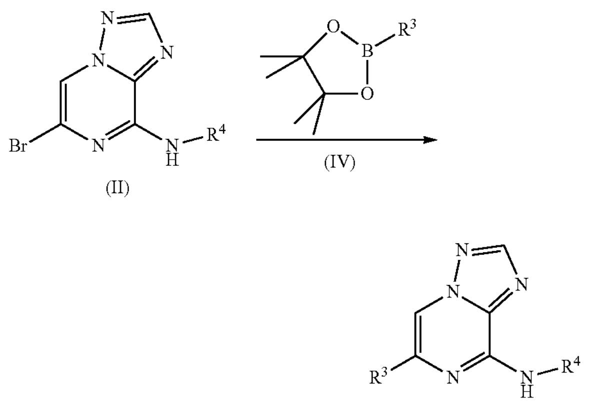

(II) (IV) (I)

General Method C

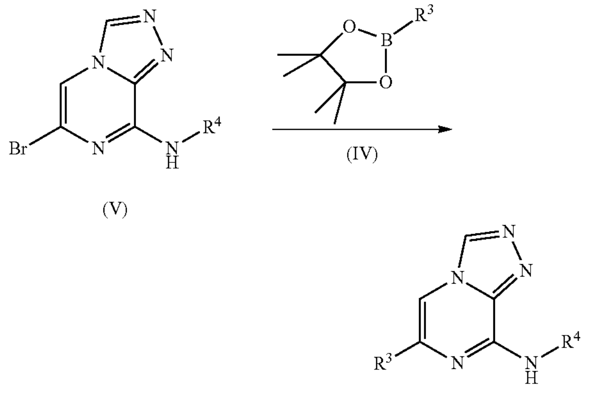

(V) (IV) (I)

General method D

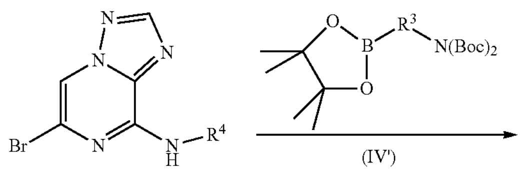

(II) (IV')

-continued

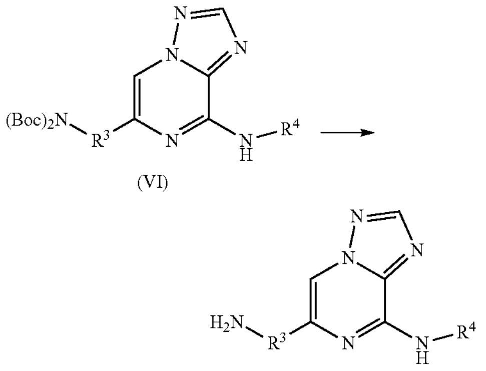

(VI) (I')

As mentioned above, $R^3$ is phenyl, pyrazinyl, pyridinyl, pyrazolyl, indazolyl, benzothiazolyl, benzodioxolyl, thiazolyl, indolyl, isoindolyl, 2H-pyrido[3,2-b][1,4]oxazin-3(4H)-one-yl, 2H-1,4-benzoxazin-3(4H)-one-yl; wherein the phenyl, pyrazinyl, pyridinyl, pyrazolyl, indazolyl, benzothiazolyl, benzodioxolyl, thiazolyl, indolyl, isoindolyl, 2H-pyrido[3,2-b][1,4]oxazin-3(4H)-one-yl, 2H-1,4-benzoxazin-3(4H)-one-yl may be optionally substituted with zero, one, two, or three substituents independently selected from the group consisting of carboxyl, amino, halo, $C_{1-6}$ alkyl, $C_{1-6}$ alkoxy, $C_{2-6}$ alkenyl, $C_{2-6}$ alkynyl, $C_{3-8}$ cycloalkyl, —C(O)—NHR$^5$; wherein $R^5$ is independently selected from the group consisting of hydrogen, benzoyloxy, $C_{1-6}$ alkyl, $C_{2-6}$ alkenyl, $C_{2-6}$ alkynyl;

$R^4$ is phenyl, pyridinyl, benzodioxolyl;

wherein the phenyl, pyridinyl, benzodioxolyl may be optionally substituted with zero, one, two, or three substituents independently selected from the group consisting of halo, $C_{1-6}$ alkyl, $C_{1-6}$ alkoxy, $C_{3-8}$ cycloalkoxy, piperazinyl,

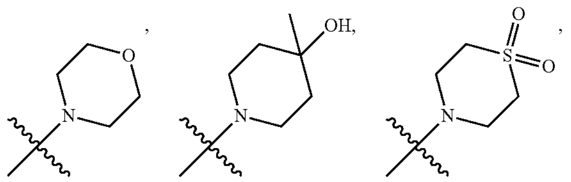

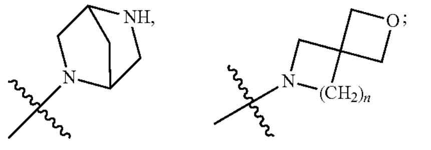

wherein the $C_{1-6}$ alkyl, $C_{1-6}$ alkoxy may be optionally substituted with zero, one, two, or three haloes, wherein the piperazinyl may be optionally substituted with one or two substituents independently selected from the group consisting of $C_{1-6}$ alkyl, $C_{3-8}$ cycloalkyl, oxacycloalkyl of $C_{2-6}$, ethylsulfonyl, methylsulfonyl, hydroxyethyl, methoxyethyl, trifluoromethyl, trifluoroethyl, wherein the

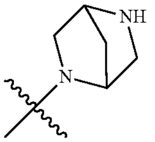 [SMILES: *N1CC2CC1CN2]

is optionally substituted with one or two substituents independently selected from the group consisting of $C_{1-6}$ alkyl, oxacycloalkyl of $C_{2-6}$; wherein n is 1 or 2.

Preparation and Examples

The present invention can be better understood according to the following examples. However, it would be easy for a person skilled in the art to understand that the contents described in the examples are merely intended to illustrate the present invention rather than limit the present invention described in detail in the claims.

Unless otherwise indicated, compounds of the present invention can be prepared beginning with commercially starting materials and utilizing general synthetic techniques and procedures known to those skilled in the art. Chromatography supplies and equipment may be purchased from such companies as for example AnaLogix, Inc, Burlington, WI; Analytical Sales and Services, Inc., Pompton Plains, NJ; Teledyne Isco, Lincoln, NE; VWR International, Bridgeport, NJ; and Rainin Instrument Company, Woburn, MA. Chemicals and reagents may be purchased from companies such as Aldrich, Argonaut Technologies, V W R and Lancaster, Invitrogen, Sigma, Promega, Solarbio, Cisbio, Signalchem, MCE; Consumables may be purchased from companies such as Corning, Labcyte, Greiner, Nunc; Instruments may be purchased from companies such as Labcyte, PerkinElmer, Eppendorf, ThermoFisher.

Substrate Preparation

1. Synthesis of 6-bromo-N-(3-methoxy-4-morpholinophenyl)-[1,2,4]triazolo[1,5-a]pyrazin-8-amine (compound 4)

The compound 4 was prepared from commercial reagent compound 1 with scheme 1.

Scheme 1

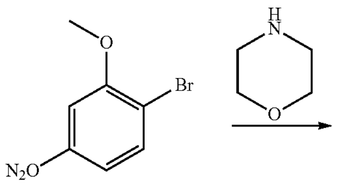

1

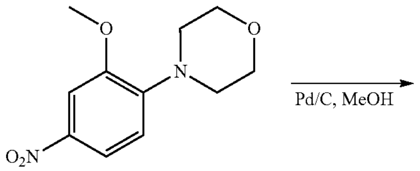

2

-continued

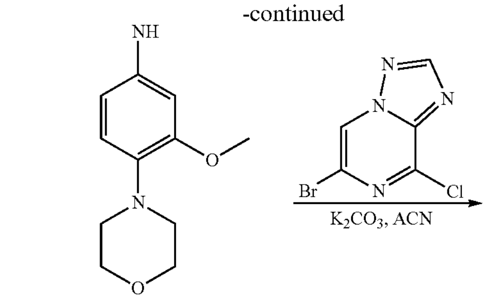

3

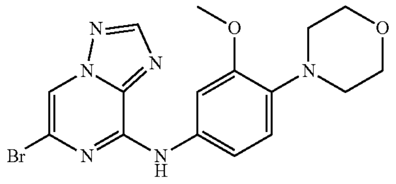

4

A 100 mL round bottom flask was charged with compound 3 (0.46 g, 2.21 mmol), 6-bromo-8-chloro-[1,2,4]triazolo[1,5-a]pyrazine (0.52 g, 2.23 mmol), $K_2CO_3$ (0.61 g, 4.42 mmol) and ACN (15 mL). The resulting mixture was stirred at 70° C. for 12 h. The reaction mixture was diluted with water and extracted with EtOAc and the combined organic layers were dried over anhydrous $Na_2SO_4$ and concentrated in vacuum. The residue was further purified by flash column chromatography on silica gel with 30% EtOAc in Petroleum to afford desired product compound 4 (0.57 g) as a yellow solid.

3. Synthesis of 6-bromo-N-(3,4,5-trimethoxyphenyl)-[1,2,4]triazolo[1,5-a]pyrazin-8-amine (compound 9)

Scheme 4

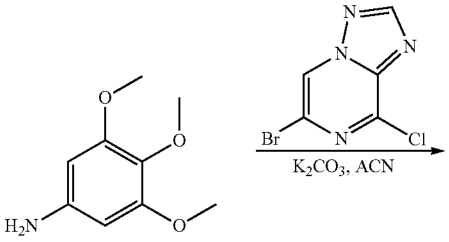

8

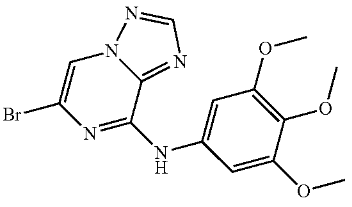

9

With the similar reaction conditions of synthesizing compound 4, starting from commercial reagent compound 8, and using scheme 4, compound 9 was obtained as a yellow solid (0.60 g).

4. Synthesis of 6-bromo-N-(3-methoxy-4-(4-(2,2,2-trifluoroethyl)piperazin-1-yl)phenyl)-[1,2,4]triazolo[1,5-a]pyrazin-8-amine (compound 16)

Scheme 5

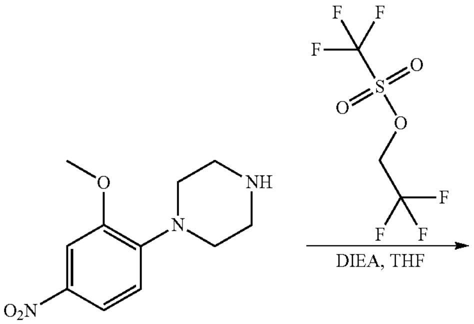

13

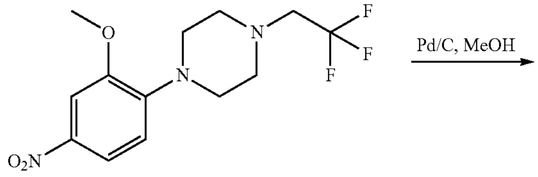

14

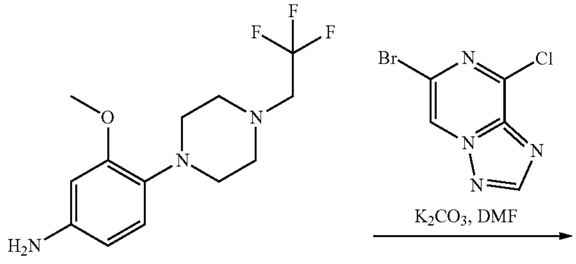

15

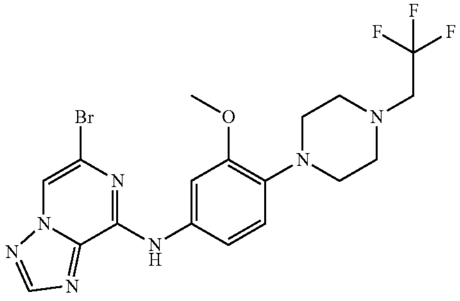

16

With the similar reaction conditions of synthesizing compound 4, starting from commercial reagent compound 13, and using scheme 5, the crude product 16 was obtained. This crude product was purified by flash column chromatography on silica gel with 5% MeOH in DCM afford compound I6 (0.23 g).

5. Synthesis of 6-bromo-N-(4-morpholino-3-(trifluoromethoxy)phenyl)-[1,2,4]triazolo[1,5-a]pyrazin-8-amine (compound 21)

The compound 21 was prepared from commercial reagent compound I7 with scheme 6.

Scheme 6

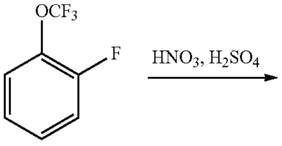

17

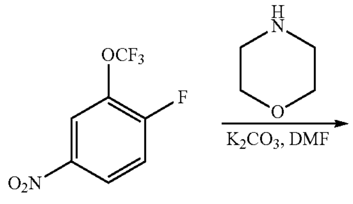

18

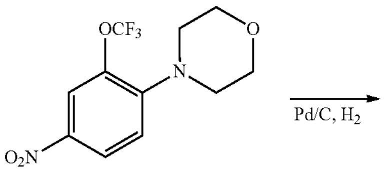

19

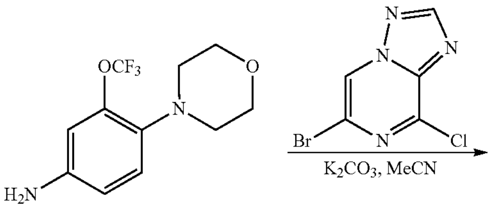

20

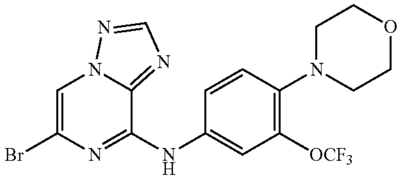

21

A solution of compound I8 (1.0 g, 8.8 mmol) in DMF 20 mL was added $K_2CO_3$ (1.8 g, 13.2 mmol) and morpholine (0.76 g, 8.8 mmol) at rt. After stirring for 16 h, the reaction system was poured into water. Extracted with DCM and washed with brine. After drying ($Na_2SO_4$) and concentration, the crude product was triturated with PE:EA=7:1 to afford the crude product compound I9 (1.2 g).

A solution of compound I9 (1.0 g, 3.4 mmol) in ethanol (20 mL) was added palladium on carbon, the reaction was stirred under 1 bar hydrogen atmosphere for 16 h. The resulting mixture was filtered through Celite and the filtrate was concentrated in vacuum to give a crude product compound 20 (0.8 g).

With the similar reaction conditions of synthesizing compound 4, compound 21 was obtained as a yellow solid (0.9 g).

6. Synthesis of 6-bromo-N-(3-(difluoromethoxy)-4-morpholinophenyl)-[1,2,4]triazolo[1,5-a]pyrazin-8-amine (compound 26)

The compound 26 was prepared from commercial reagent compound 22 with scheme 7.

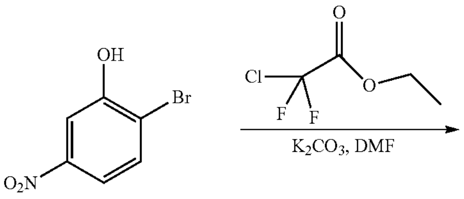

22

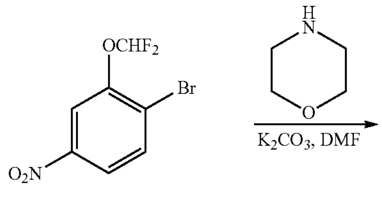

23

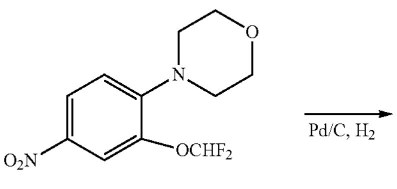

24

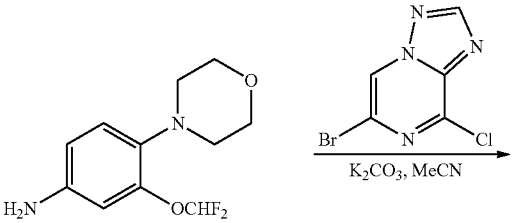

25

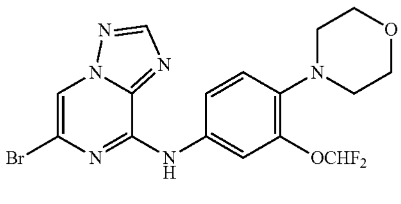

26

With the similar reaction conditions of synthesizing compound I9, crude product compound 24 was obtained (0.7 g).

With the similar reaction conditions of synthesizing compound 20, crude product compound 25 was obtained (0.6 g).

With the similar reaction conditions of synthesizing compound 4, compound 26 was obtained as a yellow solid (0.40 g).

7. Synthesis of 1-(4-((6-bromo-[1,2,4]triazolo[1,5-a]pyrazin-8-yl)amino)-2-methoxyphenyl)-4-methylpiperidin-4-ol (compound 29)

Scheme 8

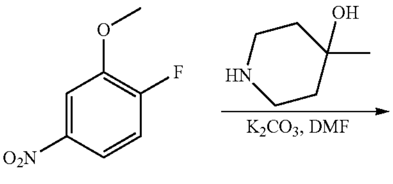

5

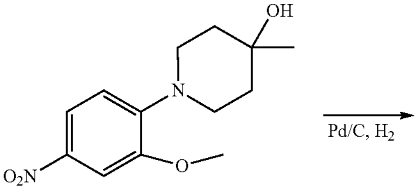

27

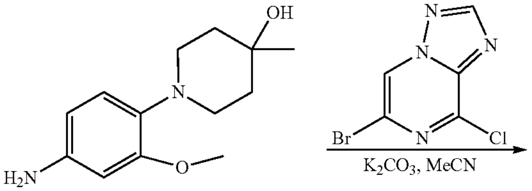

28

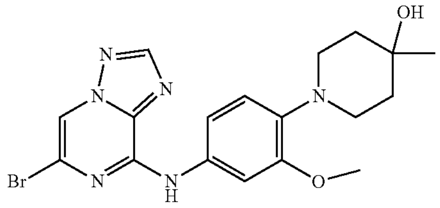

29

With the similar reaction conditions of synthesizing compound 4, starting from commercial reagent compound 5, and using scheme 8, compound 29 was obtained as a yellow solid (0.3 g).

8. Synthesis of 1-(4-((6-bromo-[1,2,4]triazolo[1,5-a]pyrazin-8-yl)amino)phenyl)-4-methylpiperidin-4-ol (compound 33)

Scheme 9

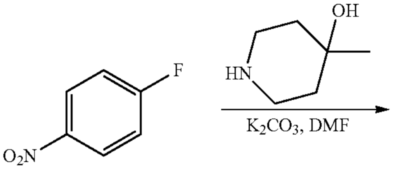

30

-continued

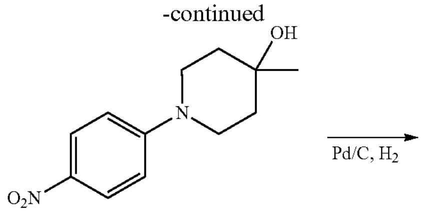

31

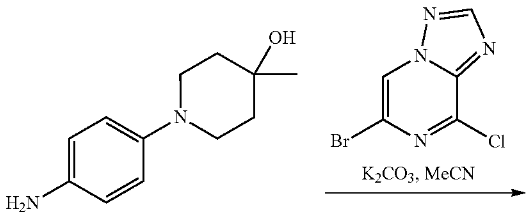

32

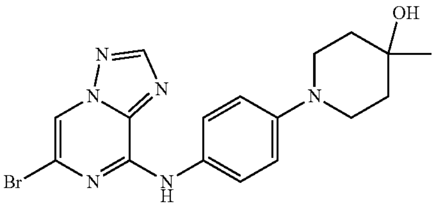

33

With the similar reaction conditions of synthesizing compound 4, starting from commercial reagent compound 5, and using scheme 9, compound 33 was obtained as a yellow solid (0.40 g).

9. Synthesis of 4-(4-((6-bromo-[1,2,4]triazolo[1,5-a]pyrazin-8-yl)amino)-2-methoxyphenyl)thiomorpholine 1,1-dioxide (compound 37)

Scheme 10

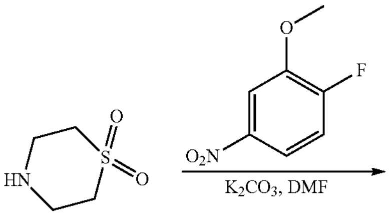

34

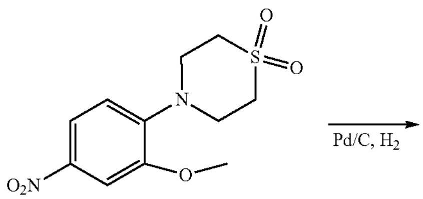

35

-continued

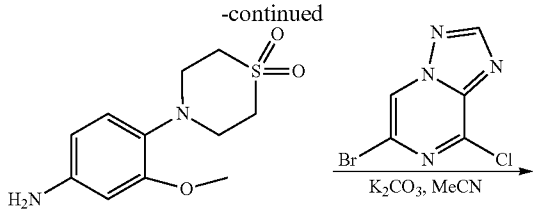

36

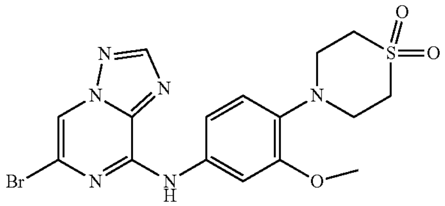

37

With the similar reaction conditions of synthesizing compound 4, starting from commercial reagent compound 34, and using scheme 10, compound 37 was obtained as a yellow solid (1.0 g).

10. Synthesis of 4-(4-((6-bromo-[1,2,4]triazolo[1,5-a]pyrazin-8-yl)amino)phenyl)thiomorpholine 1,1-dioxide (compound 40)

Scheme 11

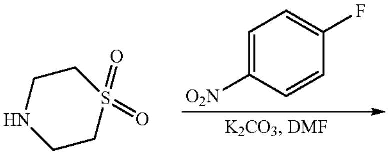

34

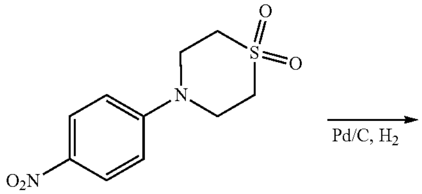

38

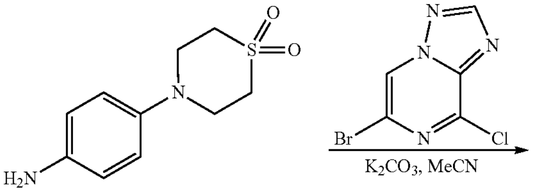

39

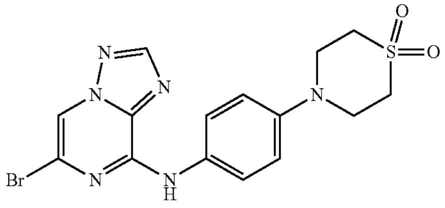

40

With the similar reaction conditions of synthesizing compound 4, starting from commercial reagent compound 34, and using scheme 11, compound 40 was obtained as a yellow solid (0.90 g).

14. Synthesis of 2,2-dimethyl-6-(4,4,5,5-tetramethyl-1,3,2-dioxaborolan-2-yl)-2H-pyrido[3,2-b][1,4]oxazin-3(4H)-one (compound 55)

The compound 55 was prepared from commercial reagent compound 52 with scheme 15.

Scheme 15

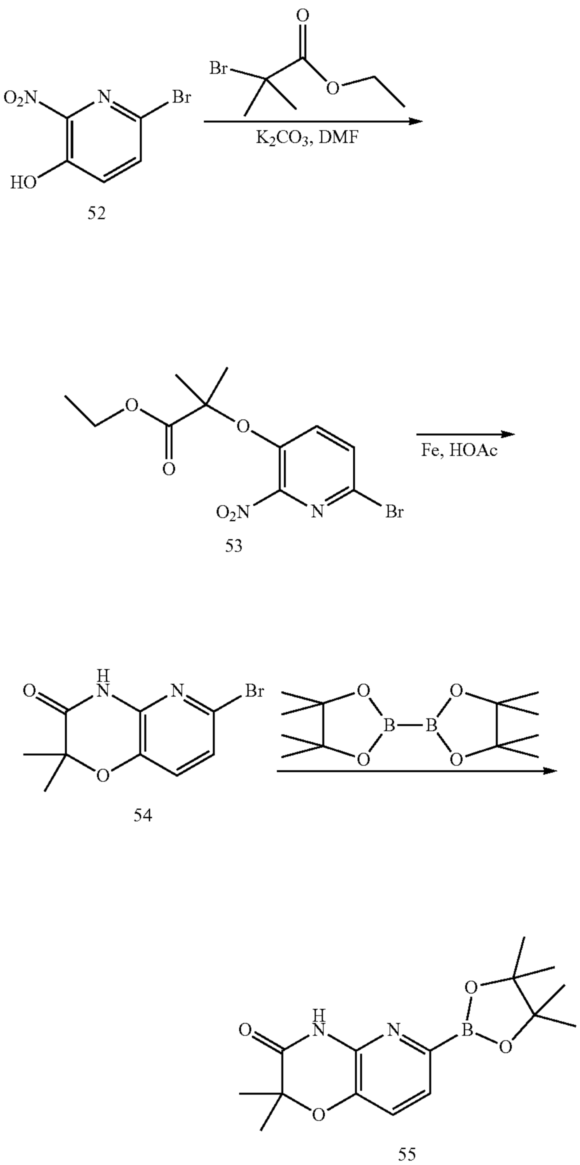

A solution of compound 54 (1.2 g, 4.67 mmol) in dioxane (50 mL) were added bis(pinacolato)diboron (1.10 eq.), potassium acetate (3.5 eq.) and 1,1'-bis(diphenylphosphino) ferrocene (0.05 eq.). The mixture was heated at 80° C. under inert atmosphere for 1 h and used to next step directly.

15. Synthesis of 6-bromo-N-(2,2-difluorobenzo[d][1,3]dioxol-5-yl)-[1,2,4]triazolo[1,5-a]pyrazin-8-amine (compound 57)

Scheme 16

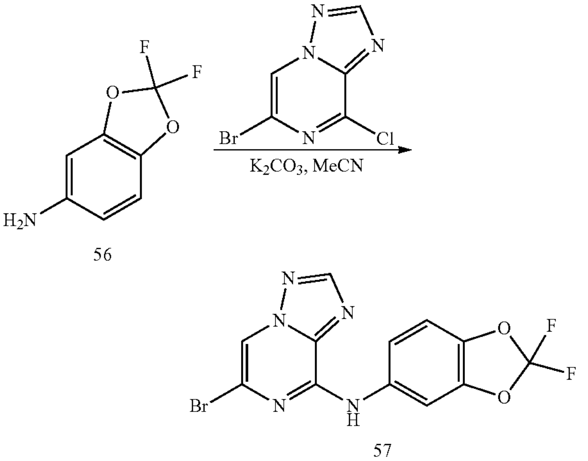

With the similar reaction conditions of synthesizing compound 4, starting from commercial reagent compound 56, and using scheme 16, compound 57 was obtained as a yellow solid (1.2 g). LCMS: $[M+H^+]=370.0$. $^1H$ NMR (300 MHz, DMSO-$d_6$) δ 7.83-7.77 (m, 2H), 7.48 (s, 1H), 7.46 (s, 1H), 7.36 (d, J=16.2 Hz, 1H).

16. Synthesis of 6-bromo-N-(3-fluoro-4-morpholinophenyl)-[1,2,4]triazolo[4,3-a]pyrazin-8-amine (compound 59)

Scheme 17

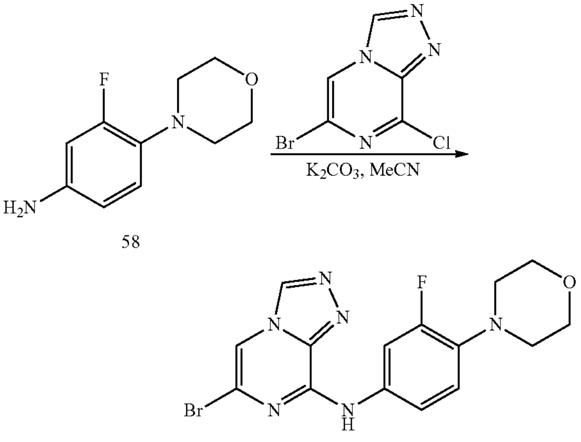

With the similar reaction conditions of synthesizing compound 4, starting from commercial reagent compound 58, and using scheme 17, compound 59 was obtained as a yellow solid (0.30 g). LCMS: $[M+H]^+=394.0$. $^1H$ NMR (300 MHz, DMSO-$d_6$) δ 13.2 (s, 1H), 9.28 (s, 1H), 8.13-8.01 (s, 3H), 7.94 (d, J=9.9 Hz, 1H), 3.76-3.72 (m, 4H), 3.01-2.96 (m, 4H).

17. Synthesis of 6-bromo-N-(3-chloro-4-morpholinophenyl)-[1,2,4]triazolo[4,3-a]pyrazin-8-amine (compound 61)

Scheme 18

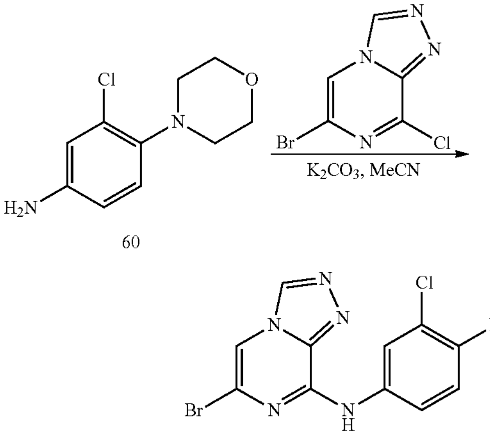

60

61

With the similar reaction conditions of synthesizing compound 4, starting from commercial reagent compound 60, and using scheme 18, compound 61 was obtained as a yellow solid (0.50 g). LCMS: $[M+H]^+$=409.1. $^1H$ NMR (300 MHz, DMSO-$d_6$) δ 9.29 (s, 1H), 8.37 (s, 1H), 8.13-8.09 (m, 3H), 7.69 (d, J=8.7 Hz, 1H), 3.77-3.72 (m, 4H), 3.00-2.95 (m, 4H).

18. Synthesis of 6-bromo-N-(3-methyl-4-morpholinophenyl)-[1,2,4]triazolo[4,3-a]pyrazin-8-amine (compound 63)

Scheme 19

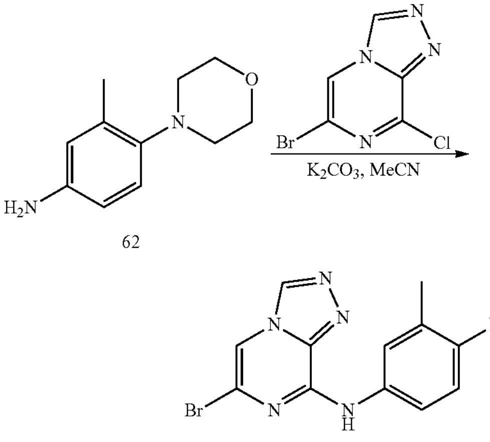

62

63

With the similar reaction conditions of synthesizing compound 4, starting from commercial reagent compound 62, and using scheme 19, compound 63 was obtained as a yellow solid (0.40 g). LCMS: $[M+H]^+$=389.0. $^1H$ NMR (300 MHz, DMSO-$d_6$) δ 10.18 (s, 1H), 8.20 (s, 1H), 8.12 (s, 1H), 8.04 (s, 1H), 7.87 (d, J=6.3 Hz, 1H), 3.78-3.74 (m, 4H), 2.90-2.85 (m, 4H), 2.36 (s, 3H).

19. Synthesis of 6-bromo-N-(6-morpholinopyridin-3-yl)-[1,2,4]triazolo[4,3-a]pyrazin-8-amine (compound 65)

Scheme 20

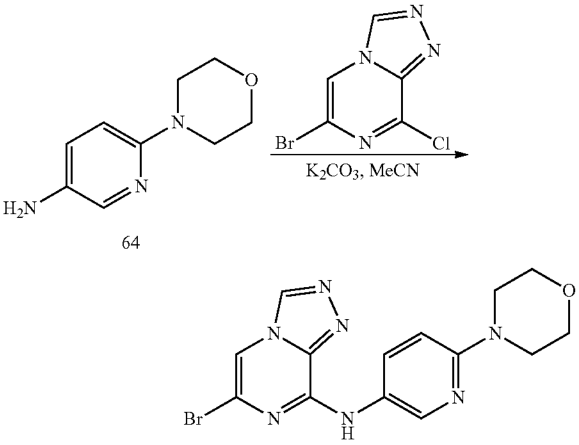

64

65

With the similar reaction conditions of synthesizing compound 4, starting from commercial reagent compound 64, and using scheme 20, compound 65 was obtained as a yellow solid (0.40 g) LCMS: $[M+H]^+$=376.1. $^1H$ NMR (300 MHz, DMSO-$d_6$) δ 9.26 (s, 1H), 8.56 (s, 1H), 8.22 (d, J=9.9 Hz, 1H), 8.07 (s, 2H), 7.64 (d, J=9.9 Hz, 1H), 3.72-3.67 (m, 4H), 3.21-3.06 (m, 4H).

23. Synthesis of 6-bromo-N-(4-(4-methylpiperazin-1-yl)phenyl)-[1,2,4]triazolo[1,5-a]pyrazin-8-amine (compound 79)

Scheme 24

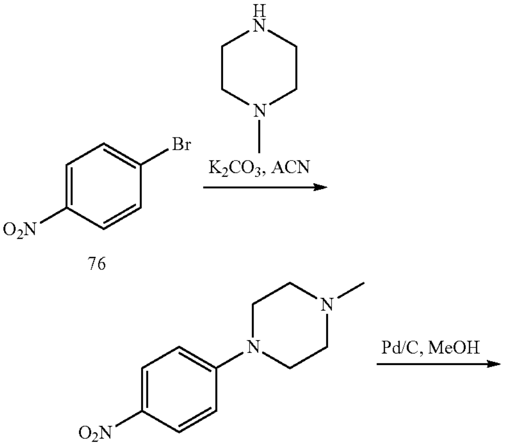

76

77

-continued

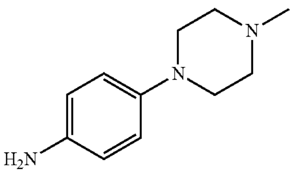

78

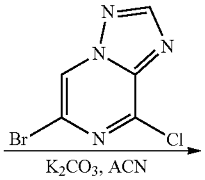

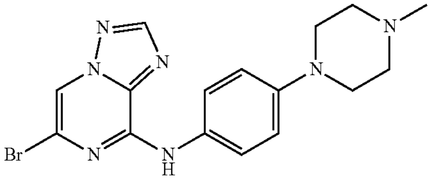

79

With the similar reaction conditions of synthesizing compound 4, starting from commercial reagent compound 76, and using scheme 24, compound 79 was obtained as a yellow solid (0.59 g).

24. Synthesis of 6-bromo-N-(3-methoxy-4-(4-methylpiperazin-1-yl)phenyl)-[1,2,4]triazolo[1,5-a]pyrazin-8-amine (compound 82)

Scheme 25

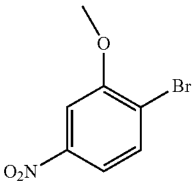

1

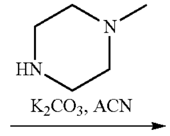

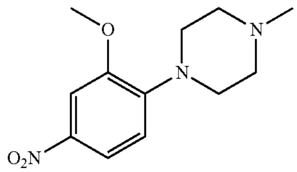

80

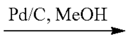

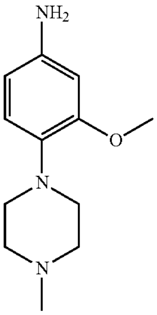

81

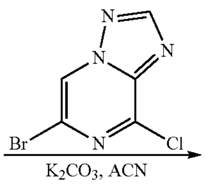

-continued

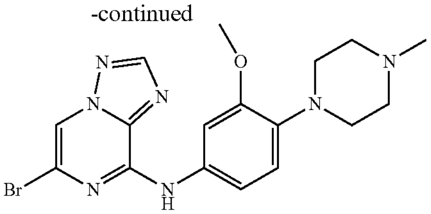

82

With the similar reaction conditions of synthesizing compound 4, starting from commercial reagent compound 1, and using scheme 25, compound 82 was obtained as a yellow solid (0.57 g).

25. Synthesis of 6-bromo-N-(4-(4-(ethylsulfonyl)piperazin-1-yl)-3-methoxyphenyl)-[1,2,4]triazolo[1,5-a]pyrazin-8-amine (compound 85)

Scheme 26

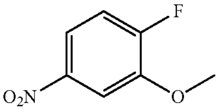

5

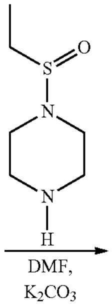

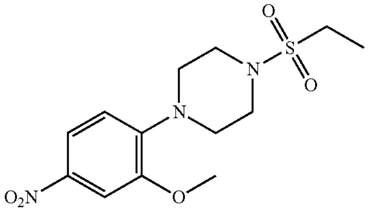

83

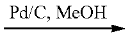

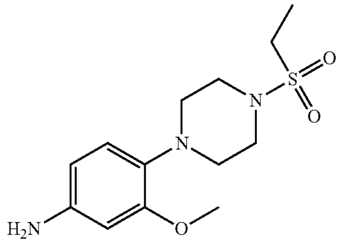

84

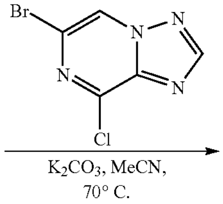

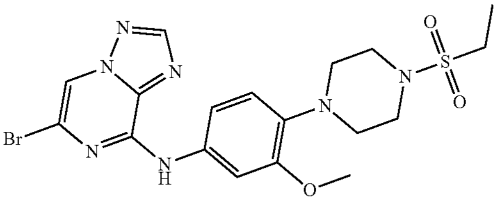

85

With the similar reaction conditions of synthesizing compound 4, starting from commercial reagent compound 5, and using scheme 26, compound 85 was obtained as a yellow solid (0.50 g).

26 Synthesis of 6-bromo-N-(4-(4-(ethylsulfonyl)piperazin-1-yl)phenyl)-[1,2,4]triazolo[1,5-a]pyrazin-8-amine (compound 91)

Scheme 27

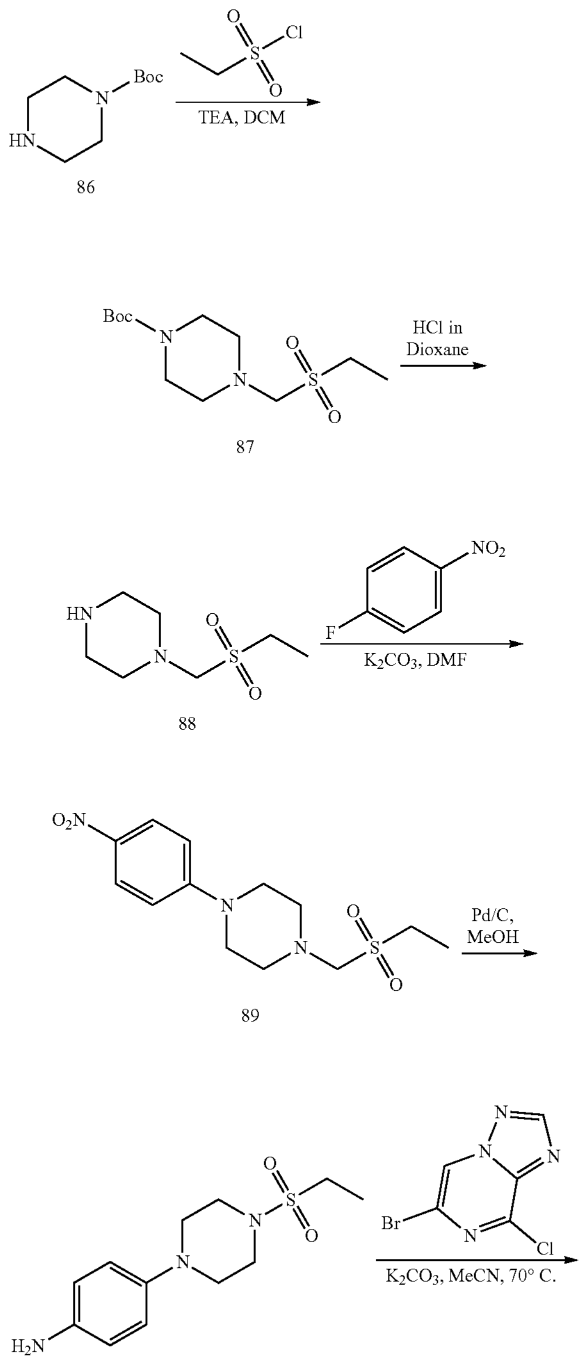

86, 87, 88, 89, 90

-continued

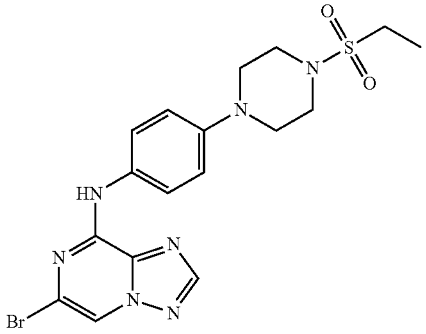

91

Scheme 27

With the similar reaction conditions of synthesizing compound 4, starting from commercial reagent compound 86, and using scheme 27, compound 91 was obtained as a yellow solid (0.52 g).

27. Synthesis of 2-(4-(4-((6-bromo-[1,2,4]triazolo[1,5-a]pyrazin-8-yl)amino)-2-methoxyphenyl)piperazin-1-yl)ethan-1-ol (compound 94)

Scheme 28

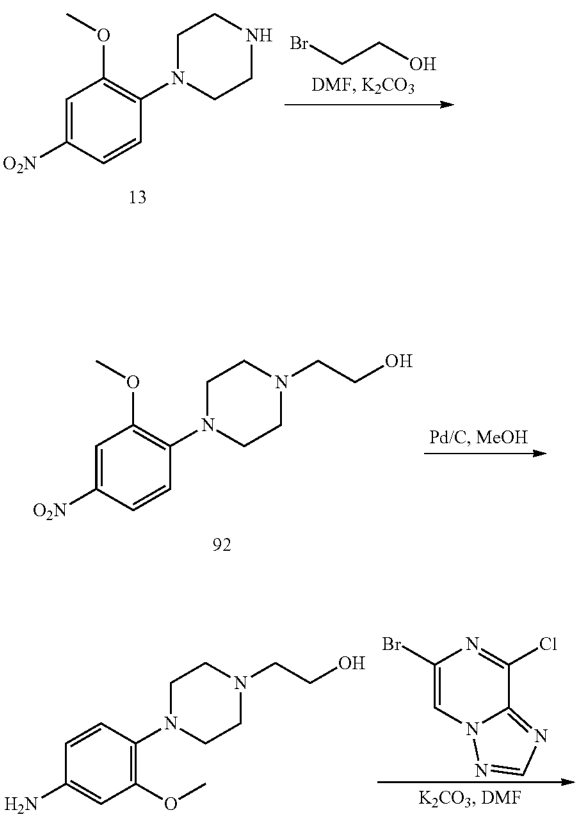

13, 92, 93

-continued

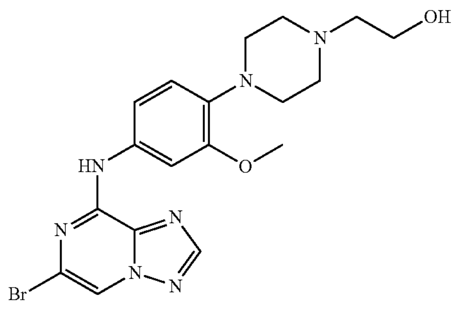

94

With the similar reaction conditions of synthesizing compound 4, starting from commercial reagent compound 13, and using scheme 28, compound 94 was obtained as a yellow solid (0.22 g).

28 Synthesis of 6-bromo-N-(4-(4-ethylpiperazin-1-yl)-3-methoxyphenyl)-[1,2,4]triazolo[1,5-a]pyrazin-8-amine (compound 98)

Scheme 29

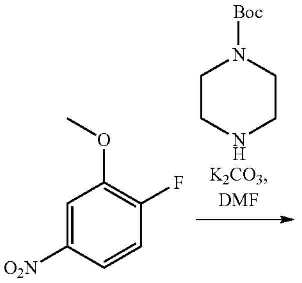

5

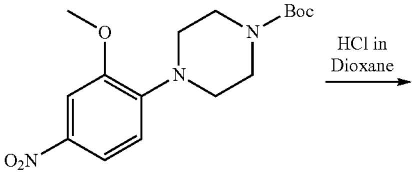

95

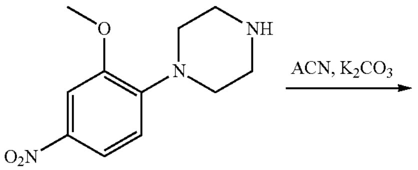

13

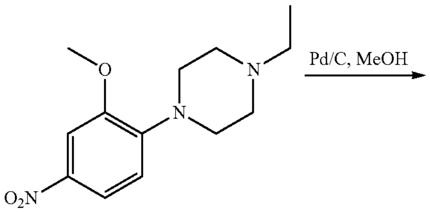

96

-continued

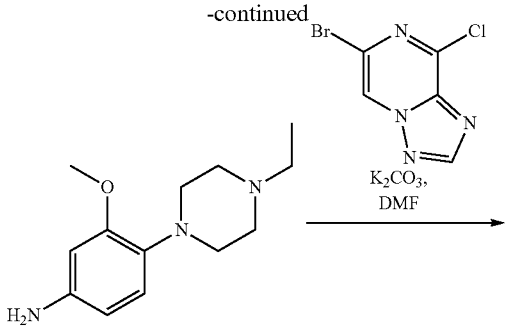

97

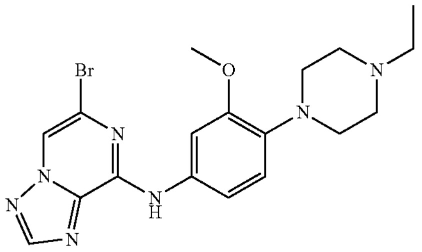

98

With the similar reaction conditions of synthesizing compound 4, starting from commercial reagent compound 5, and using scheme 29, compound 98 was obtained as a yellow solid (0.3 g).

29. Synthesis of 6-bromo-N-(4-(4-isopropylpiperazin-1-yl)-3-methoxyphenyl)-[1,2,4]triazolo[1,5-a]pyrazin-8-amine (compound 101)

Scheme 30

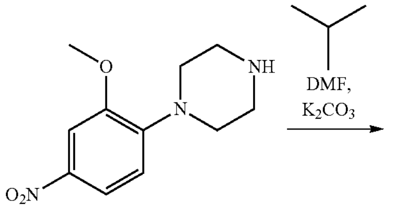

13

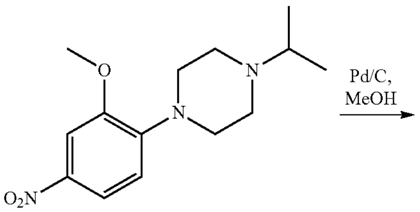

99

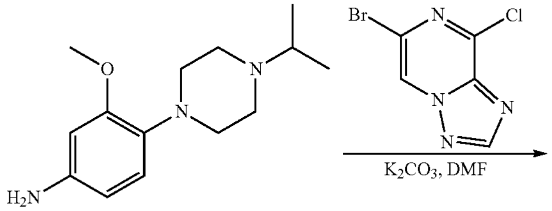

100

-continued

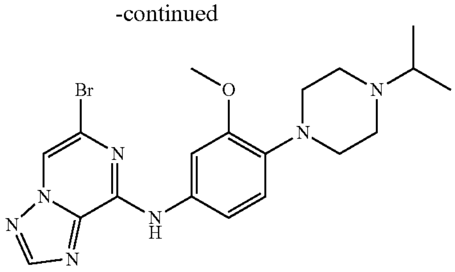

101

With the similar reaction conditions of synthesizing compound 4, starting from commercial reagent compound 13, and using scheme 30, compound 101 was obtained as a yellow solid (0.25 g).

30. Synthesis of 6-bromo-N-(3-methoxy-4-(4-(2-methoxyethyl)piperazin-1-yl)phenyl)-[1,2,4]triazolo[1,5-a]pyrazin-8-amine (compound 104)

Scheme 31

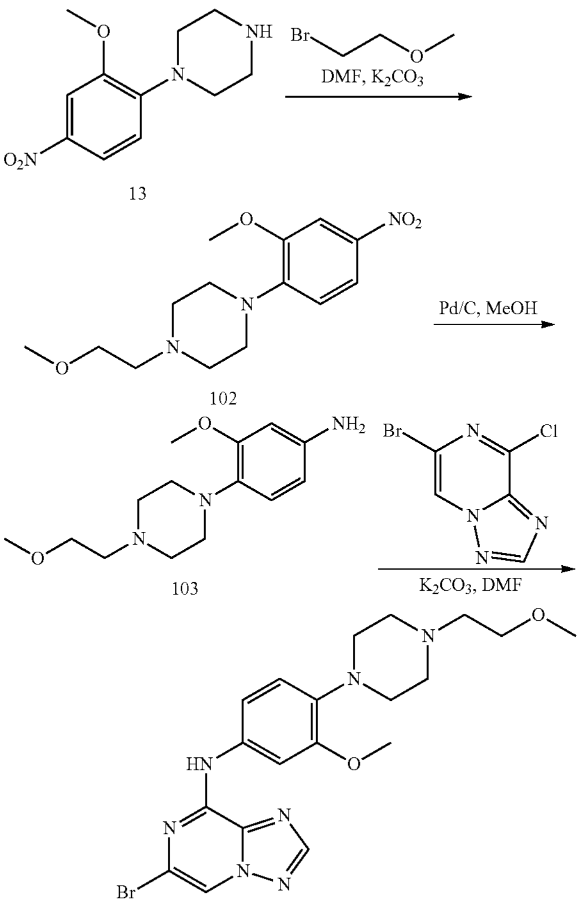

13

102

103

104

Using the similar reaction conditions of synthesizing compound 4, starting from commercial reagent compound 13, and using scheme 31, compound 104 was obtained as a yellow solid (0.31 g).

31. Synthesis of 6-bromo-N-(4-(4-cyclopropylpiperazin-1-yl)-3-methoxyphenyl)-[1,2,4]triazolo[1,5-a]pyrazin-8-amine (compound 107)

The compound 107 was prepared from commercial reagent compound 13 with scheme 32.

Scheme 32

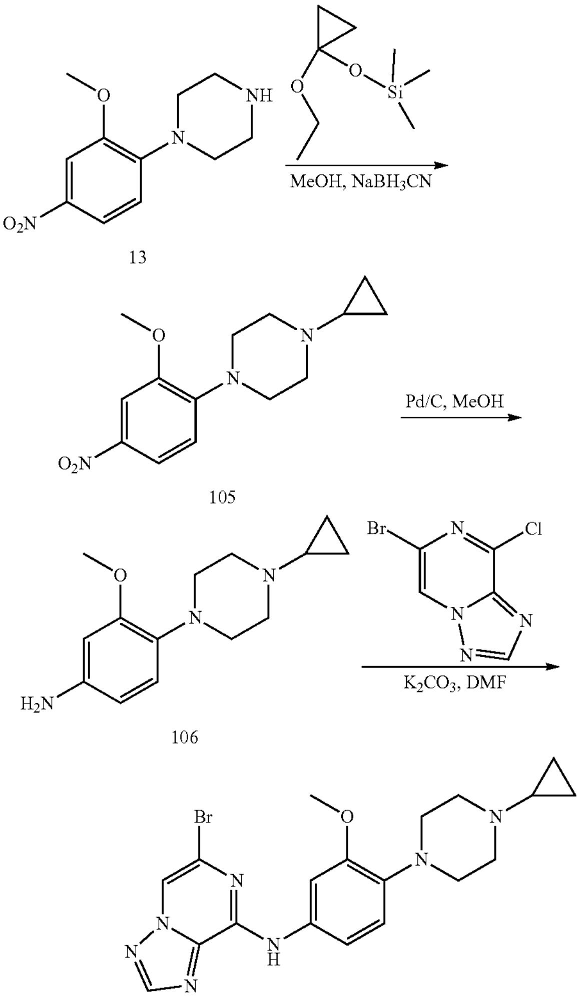

13

105

106

107

A solution of compound 13 (1.0 g, 4.2 mmol) in MeOH 15 mL was added $NaBH_3CN$ (0.8 g, 12.6 mmol), (1-ethoxycyclopropoxy)trimethylsilane (1.46 g, 8.4 mmol) and 8 ml $CH_3COOH$ was heated to reflux for 5 h. The reaction system was adjusted to pH9. Extracted with DCM and washed with brine. After drying ($Na_2SO_4$) and concentration, the crude product was purified by flash column chromatography on silica gel with 10% EA in PE to afford of compound 105 (0.85 g).

Using the similar hydergenation conditions of synthesizing compound 20, compound 106 was obtained as a crude product (0.61 g).

Using the similar reaction conditions of synthesizing compound 4, compound 107 was obtained as a yellow solid (0.42 g).

EXAMPLES

Example 1. 6-(1H-indazol-6-yl)-N-(3-methoxy-4-morpholinophenyl)-[1,2,4]triazolo[1,5-a]pyrazin-8-amine (I1)

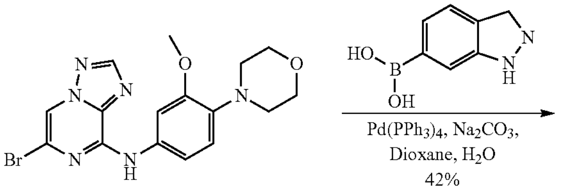

4

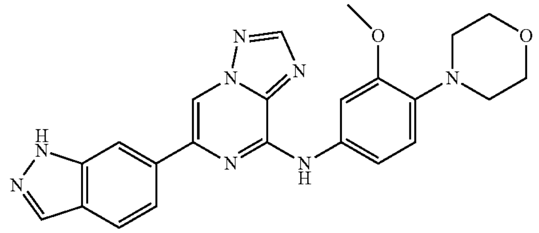

I1

A 100 mL round-bottom flask purged and maintained under an inert atmosphere of nitrogen for 3 times, was placed compound 4 (90 mg, 0.22 mmol), 1H-indazol-6-ylboronic acid (42.8 mg, 0.26 mmol), $Na_2CO_3$ (74.2 mg, 0.7 mmol), $Pd(PPh_3)_4$ (80 mg, 0.07 mmol), 1,4-dioxane (10 mL) and water (1 mL). The resulting mixture was heated at 100° C. under inert atmosphere for 10 h. The reaction mixture was diluted with water and extracted with EtOAc. The combined organic layers were dried over anhydrous $Na_2SO_4$ and concentrated in vacuum. The residue was purified by flash column chromatography on silica gel with 20% MeOH in DCM to afford 41 mg of compound I1 as a white solid. LCMS (ESI-MS): $[M+H]^+$=443.0. $^1$H NMR (400 MHz, DMSO-$d_6$) δ 13.26 (s, 1H), 10.02 (s, 1H), 9.06 (s, 1H), 8.65 (s, 1H), 8.31 (s, 1H), 8.12 (s, 1H), 8.02 (d, J=1.9 Hz, 1H), 7.95-7.81 (m, 2H), 7.65 (dd, J=8.6, 2.1 Hz, 1H), 6.96 (d, J=8.6 Hz, 1H), 3.86 (s, 3H), 3.74 (dd, J=20.5, 15.9 Hz, 4H), 3.00 (s, 4H).

Example 2. 6-(1H-indol-6-yl)-N-(3-methoxy-4-morpholinophenyl)-[1,2,4]triazolo[1,5-a]pyrazin-8-amine (I2)

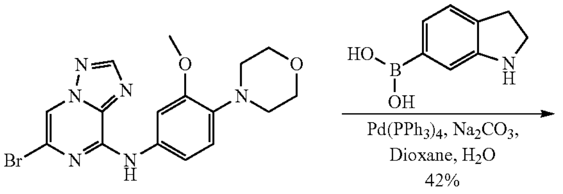

4

-continued

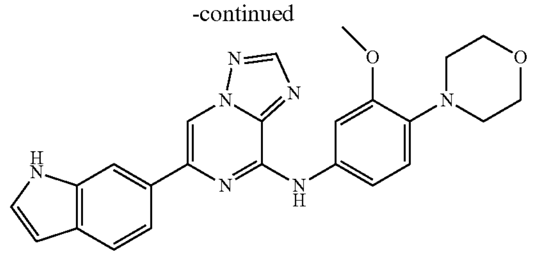

I2

A 100 mL round-bottom flask purged and maintained under an inert atmosphere of nitrogen for 3 times, was placed compound 4 (400 mg, 0.99 mmol), 1H-indol-6-ylboronic acid (195 mg, 1.2 mmol), $Na_2CO_3$ (344 mg, 3.2 mmol), $Pd(PPh_3)_4$ (190 mg, 0.16 mmol), 1,4-dioxane (20 mL) and water (2 mL). The resulting mixture was heated at 100° C. under inert atmosphere for 10 h. The reaction mixture was diluted with water and extracted with EtOAc. The combined organic layers were dried over anhydrous $Na_2SO_4$ and concentrated in vacuum. The residue was purified by flash column chromatography on silica gel with 20% MeOH in DCM to afford 35 mg of compound I2 as a white solid. LCMS: $[M+H]^+$=442.2. $^1$H NMR (300 MHz, DMSO-$d_6$) δ 11.31 (s, 1H), 9.94 (s, 1H), 8.90 (s, 1H), 8.60 (s, 1H), 8.19 (s, 1H), 8.04 (s, 1H), 7.78-7.61 (m, 3H), 7.43 (s, 1H), 6.95 (d, J=8.4 Hz, 1H), 6.48 (s, 1H), 3.90-3.71 (m, 8H), 2.98 (s, 3H).

The following compounds can be prepared using general method A and similar methods with examples 1-2:

N-(3,4-dimethoxyphenyl)-6-(1H-indazol-6-yl)-[1,2,4]triazolo[1,5-a]pyrazin-8-amine (I3) was obtained as a white solid (0.047 g). LCMS (ESI-MS): $[M+H]^+$=388. $^1$H NMR (400 MHz, DMSO-$d_6$) δ 13.28 (s, 1H), 10.04 (s, 1H), 9.08 (s, 1H), 8.66 (s, 3H), 8.30 (s, 1H), 8.12 (s, 1H), 8.03 (d, J=2.4 Hz, 1H), 7.93-7.82 (m, 2H), 7.61 (dd, J=8.7, 2.4 Hz, 1H), 7.01 (d, J=8.8 Hz, 1H), 3.82 (s, 3H), 3.79 (s, 3H).

6-(1H-indazol-6-yl)-N-(3,4,5-trimethoxyphenyl)-[1,2,4]triazolo[1,5-a]pyrazin-8-amine (I4) was obtained as a white solid (0.050 g). LCMS (ESI-MS): $[M+H]^+$=418.1. $^1$H NMR (300 MHz, DMSO-$d_6$) δ 13.29 (s, 1H), 10.05 (s, 1H), 9.10 (s, 1H), 8.67 (s, 1H), 8.30 (s, 1H), 8.12 (s, 1H), 7.92-7.84 (m, 2H), 7.71 (bs, 2H), 3.92 (s, 6H), 3.59 (s, 3H).

4-(8-((4-morpholinophenyl)amino)-[1,2,4]triazolo[1,5-a]pyrazin-6-yl)benzamide (I5) was obtained as a white solid (0.045 g). LCMS (ESI-MS): $[M+H]^+$=416.0. $^1$H NMR (400 MHz, DMSO-$d_6$) δ 9.97 (s, 1H), 9.06 (s, 1H), 8.64 (s, 1H), 8.18 (d, J=8.3 Hz, 2H), 8.10-7.92 (m, 5H), 7.42 (s, 1H), 7.02 (d, J=9.0 Hz, 2H), 3.88-3.68 (m, 4H), 3.18-3.06 (m, 4H).

3-(8-((4-morpholinophenyl)amino)-[1,2,4]triazolo[1,5-a]pyrazin-6-yl)benzamide (16) was obtained as a white solid (0.017 g). LCMS (ESI-MS): $[M+H]^+$=416.0. $^1$H NMR (400 MHz, DMSO-$d_6$): δ 9.97 (s, 1H), 9.01 (s, 1H), 8.63 (s, 1H), 8.57 (s, 1H), 8.24-8.22 (d, J=7.6 Hz, 1H), 8.07 (s, 1H), 7.99-7.97 (d, J=8.8 Hz, 2H), 7.90-7.88 (d, J=7.2 Hz, 1H), 7.60-7.59 (d, J=7.6 Hz, 1H), 7.46 (s, 1H), 7.00-6.98 (d, J=8.8 Hz, 2H), 3.76 (s, 4H), 3.10 (s, 4H).

6-(1H-indazol-6-yl)-N-(3-methoxy-4-(4-(2,2,2-trifluoroethyl)piperazin-1-yl)phenyl)-[1,2,4]triazolo[1,5-a]pyrazin-8-amine (I8) was obtained as a yellow solid (0.028 g). LCMS: $[M+H]^+$=524.3. $^1$H NMR (400 MHz, DMSO-$d_6$) δ 13.27 (s, 1H), 10.02 (s, 1H), 9.07 (s, 1H), 8.65 (s, 1H), 8.30 (s, 1H), 8.12 (s, 1H), 8.01 (d, J=2.0 Hz, 1H), 7.87 (q, J=8.5

Hz, 2H), 7.61 (dd, J=8.6, 2.1 Hz, 1H), 6.95 (d, J=8.6 Hz, 1H), 3.85 (s, 2H), 3.27-3.20 (m, 2H), 3.02-2.98 (m, 4H), 2.81-2.78 (m, 4H).

6-(1H-indazol-6-yl)-N-(4-(4-methylpiperazin-1-yl)phenyl)-[1,2,4]triazolo[1,5-a]pyrazin-8-amine (I11) was obtained as a yellow solid (0.019 g). LCMS: $[M+H^+]$=427.0. $^1$H NMR (400 MHz, DMSO-$d_6$) δ 13.23 (s, 1H), 9.94 (s, 1H), 9.02 (s, 1H), 8.62 (s, 1H), 8.28 (s, 1H), 8.10 (s, 1H), 7.98 (d, J=9.0 Hz, 2H), 7.85 (s, 2H), 7.02 (d, J=9.0 Hz, 2H), 3.19-3.10 (m, 4H), 2.50-2.38 (m, 4H), 2.24 (s, 3H).

6-(1H-indazol-6-yl)-N-(3-methoxy-4-(4-methylpiperazin-1-yl)phenyl)-[1,2,4]triazolo[1,5-a]pyrazin-8-amine (I12) was obtained as a yellow solid (0.010 g). LCMS: $[M+H^+]$=455.9. $^1$H NMR (400 MHz, DMSO-$d_6$) δ 13.26 (s, 1H), 10.01 (s, 1H), 9.06 (s, 1H), 8.65 (s, 1H), 8.30 (s, 1H), 8.11 (s, 1H), 7.99 (s, 1H), 7.87 (dd, J=15.9, 8.6 Hz, 2H), 7.66-7.61 (m, 1H), 6.95 (d, J=8.6 Hz, 1H), 3.84 (s, 3H), 3.00 (s, 4H), 2.45-2.37 (m, 3H), 2.36-2.32 (m, 4H).

N-(4-(4-(ethylsulfonyl)piperazin-1-yl)-3-methoxyphenyl)-6-(1H-indazol-6-yl)-[1,2,4]triazolo[1,5-a]pyrazin-8-amine (I13) was obtained as a yellow solid (0.049 g). LCMS: $[M+H^+]$=534.0. $^1$H NMR (300 MHz, DMSO-$d_6$) δ 13.27 (s, 1H), 10.04 (d, J=11.5 Hz, 1H), 9.08 (d, J=11.2 Hz, 1H), 8.66 (d, J=11.1 Hz, 1H), 8.31 (d, J=10.9 Hz, 1H), 8.10 (dd, J=19.4, 11.2 Hz, 2H), 7.89 (d, J=7.9 Hz, 2H), 7.64 (d, J=8.8 Hz, 1H), 6.98 (d, J=9.0 Hz, 1H), 3.87 (s, 3H), 3.33-3.30 (m, 4H), 3.17-2.99 (m, 6H), 1.27 (dd, J=16.4, 9.1 Hz, 3H).

N-(4-(4-(ethylsulfonyl)piperazin-1-yl)phenyl)-6-(1H-indazol-6-yl)-[1,2,4]triazolo[1,5-a]pyrazin-8-amine (I14) was obtained as a yellow solid (0.011 g). LCMS: $[M+H^+]$=504.0. $^1$H NMR (400 MHz, DMSO-$d_6$) δ 13.24 (s, 1H), 9.98 (s, 1H), 9.03 (s, 1H), 8.63 (s, 1H), 8.27 (s, 1H), 8.11 (s, 1H), 8.02 (d, J=8.8 Hz, 2H), 7.85 (s, 2H), 7.06 (d, J=8.8 Hz, 2H), 3.36-3.32 (m, 4H), 3.26-3.20 (m, 4H), 3.13 (dd, J=14.7, 7.3 Hz, 2H), 1.25 (t, J=7.3 Hz, 3H).

2-(4-(4-((6-(1H-indazol-6-yl)-[1,2,4]triazolo[1,5-a]pyrazin-8-yl)amino)-2-methoxyphenyl)piperazin-1-yl)ethan-1-ol (I15) was obtained as a yellow solid (0.016 g). LCMS: $[M+H^+]$=486.2. $^1$H NMR (400 MHz, DMSO-$d_6$) δ 13.35 (s, 1H), 10.14 (s, 1H), 9.64 (s, 1H), 9.14 (s, 1H), 8.72 (s, 1H), 8.35 (s, 1H), 8.23-8.11 (m, 2H), 7.94 (q, J=8.5 Hz, 2H), 7.74 (dd, J=8.6, 1.9 Hz, 1H), 7.07 (d, J=8.7 Hz, 1H), 3.93 (s, 3H), 3.88-3.82 (m, 4H), 3.64 (t, J=13.7 Hz, 2H), 3.57 (d, J=12.3 Hz, 2H), 3.35-3.30 (m, 2H), 3.09 (t, J=11.5 Hz, 2H).

N-(4-(4-ethylpiperazin-1-yl)-3-methoxyphenyl)-6-(1H-indazol-6-yl)-[1,2,4]triazolo[1,5-a]pyrazin-8-amine (I16) was obtained as a yellow solid (0.040 g). LCMS $[M+H^+]$=462.2. $^1$H NMR (400 MHz, DMSO-$d_6$) δ 13.27 (s, 1H), 10.01 (s, 1H), 9.06 (s, 1H), 8.65 (s, 1H), 8.30 (s, 1H), 8.12 (s, 1H), 8.00 (s, 1H), 7.87 (q, J=8.2 Hz, 2H), 7.62 (dd, J=8.5, 2.0 Hz, 1H), 6.94 (d, J=8.6 Hz, 1H), 3.84 (s, 3H), 3.31 (s, 2H), 3.00 (s, 4H), 2.41 (s, 4H), 1.04 (t, J=7.1 Hz, 3H).

6-(1H-indazol-6-yl)-N-(4-(4-isopropylpiperazin-1-yl)-3-methoxyphenyl)-[1,2,4]triazolo[1,5-a]pyrazin-8-amine (I17) was obtained as a yellow solid (0.025 g). LCMS: $[M+H^+]$=484.2. $^1$H NMR (400 MHz, DMSO-$d_6$) δ 13.34 (s, 1H), 10.14 (s, 1H), 9.69 (s, 1H), 9.14 (s, 1H), 8.72 (s, 1H), 8.35 (s, 1H), 8.17 (d, J=12.4 Hz, 1H), 7.94 (q, J=8.4 Hz, 2H), 7.74 (d, J=8.4 Hz, 1H), 7.08 (d, J=8.6 Hz, 1H), 3.96 (d, J=20.7 Hz, 3H), 3.55-3.50 (m, 6H), 3.11-3.06 (m, 2H), 1.31 (t, J=27.9 Hz, 6H).

6-(1H-indazol-6-yl)-N-(3-methoxy-4-(4-(2-methoxyethyl)piperazin-1-yl)phenyl)-[1,2,4]triazolo[1,5-a]pyrazin-8-amine (I18) was obtained as a yellow solid (0.049 g). LCMS: $[M+H^+]$=500.2. $^1$H NMR (400 MHz, DMSO-$d_6$) δ 13.27 (s, 1H), 10.02 (s, 1H), 9.07 (s, 1H), 8.65 (s, 1H), 8.30 (s, 1H), 8.12 (s, 1H), 8.01 (s, 1H), 7.87 (dd, J=15.2, 8.5 Hz, 1H), 7.62 (d, J=8.3 Hz, 1H), 6.94 (d, J=8.3 Hz, 1H), 3.84 (s, 3H), 3.49 (s, 2H), 3.34-3.32 (m, 3H), 3.27 (s, 2H), 3.22-3.18 (m, 4H), 3.01-2.98 (m, 4H).

N-(4-(4-cyclopropylpiperazin-1-yl)-3-methoxyphenyl)-6-(1H-indazol-6-yl)-[1,2,4]triazolo[1,5-a]pyrazin-8-amine (I19) was obtained as a yellow solid (0.040 g). LCMS: $[M+H^+]$=482.2. $^1$H NMR (400 MHz, DMSO-$d_6$) δ 13.26 (s, 1H), 9.99 (s, 1H), 9.05 (s, 1H), 8.64 (s, 1H), 8.30 (s, 1H), 8.11 (s, 1H), 8.00 (s, 1H), 7.87 (q, J=8.5 Hz, 2H), 7.60 (d, J=8.4 Hz, 1H), 6.92 (d, J=8.6 Hz, 1H), 3.85 (s, 3H), 2.94 (s, 4H), 2.70 (s, 4H), 1.69 (s, 1H), 0.50-0.27 (m, 4H).

Example 3. 4-(3-(8-((4-morpholinophenyl)amino)-[1,2,4]triazolo[1,5-a]pyrazin-6-yl)benzamido)benzoic acid (17)

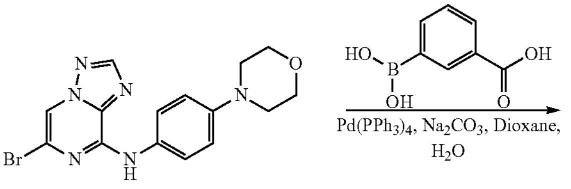

10

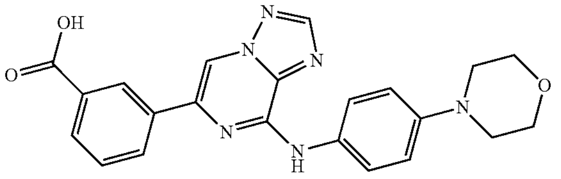

11

Using the similar reaction conditions of synthesizing compound I1, compound I1 was obtained as a white solid (0.45 g)

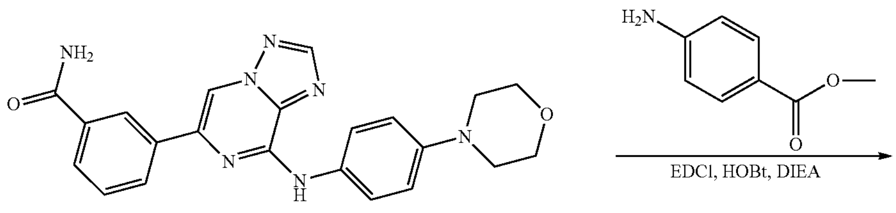

11

-continued

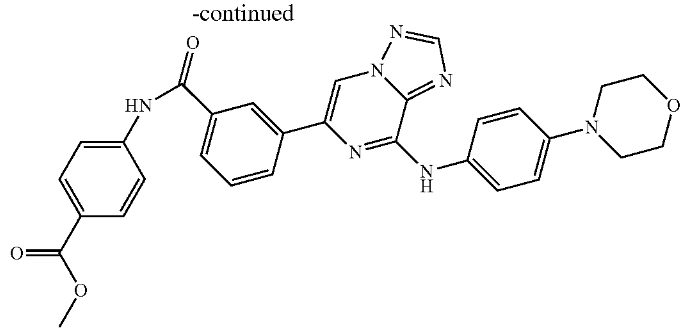

12

A 100 mL round-bottom flask purged and maintained under an inert atmosphere of nitrogen for 3 times, was placed compound I1 (450 mg, 1.08 mmol), methyl 4-aminobenzoate (210 mg, 1.26 mmol), EDCI (257 mg, 1.34 mmol), HOBt (181 mg, 1.34 mmol), DCM (20 mL) and DIEA (3 mL). The resulting mixture was heated at 100° C. under inert atmosphere for 10 h. The reaction mixture was diluted with water and extracted with EtOAc. The combined organic layers were dried over anhydrous $Na_2SO_4$ and concentrated in vacuum. The residue was purified by flash column chromatography on silica gel with 20% MeOH in DCM to afford 500 mg of compound I2 as a white solid.

To a solution of compound I2 (200 mg, 0.36 mmol) in $H_2O$ (5 mL), THF (5 mL) and MeOH (5 mL), NaOH (75 mg, 1.8 mmol) was added. The mixture was heated to 50° C. for 3 h. The mixture reaction was acidified to pH 2 with 1M HCl and extracted with EA, the organic phase was dried and concentrated. The residue was purified by column chromatography (DCM/MeOH=10/1) to afford compound I7 (28 mg). LCMS (ESI-MS): $[M+H]^+$=536.1. $^1$H NMR (300 MHz, DMSO-$d_6$) δ 12.70 (bs, 1H), 10.81 (s, 1H), 10.06 (s, 1H), 9.16 (s, 1H), 8.69 (d, J=16.2 Hz, 2H), 8.41-7.62 (m, 9H), 7.06-6.75 (m, 2H), 3.75-3.56 (m, 4H), 2.95-2.76 (m, 4H).

The following compounds can be prepared using general method A and similar methods with examples 1-3:

I9: 6-(1H-indazol-6-yl)-N-(4-morpholinophenyl)-[1,2,4]triazolo[1,5-a]pyrazin-8-amine;

I10: 6-(1H-indol-6-yl)-N-(4-morpholinophenyl)-[1,2,4]triazolo[1,5-a]pyrazin-8-amine;

I49: 6-(1H-indazol-6-yl)-N-(4-(4-(oxetan-3-yl)piperazin-1-yl)phenyl)-[1,2,4]triazolo[1,5-a]pyrazin-8-amine;

I50: 6-(1H-indazol-6-yl)-N-(3-methoxy-4-(4-(oxetan-3-yl)piperazin-1-yl)phenyl)-[1,2,4]triazolo[1,5-a]pyrazin-8-amine;

I51: 6-(6-aminopyrazin-2-yl)-N-(4-(4-(oxetan-3-yl)piperazin-1-yl)phenyl)-[1,2,4]triazolo[1,5-a]pyrazin-8-amine;

I52: 6-(6-aminopyrazin-2-yl)-N-(3-methoxy-4-(4-(oxetan-3-yl)piperazin-1-yl)phenyl)-[1,2,4]triazolo[1,5-a]pyrazin-8-amine.

Example 4. 1-(4-((6-(1H-indazol-6-yl)-[1,2,4]triazolo[1,5-a]pyrazin-8-yl)amino)-2-methoxyphenyl)-4-methylpiperidin-4-ol (I22)

A 100 mL round-bottom flask, purged and maintained under an inert atmosphere of nitrogen for 3 times, was placed compound 29 (300 mg, 0.69 mmol), 6-(4,4,5,5-tetramethyl-1,3,2-dioxaborolan-2-yl)-1H-indazole (195 mg, 1.2 mmol), $Na_2CO_3$ (344 mg, 3.2 mmol), $Pd(PPh_3)_4$ (190 mg, 0.16 mmol), 1,4-dioxane (20 mL) and water (2 mL). The resulting mixture was heated at 100° C. under inert atmosphere for 10 h. The reaction mixture was diluted with water and extracted with EtOAc. The combined organic layers were dried over anhydrous $Na_2SO_4$ and concentrated in vacuum. The residue was purified by flash column chromatography on silica gel with 20% MeOH in DCM to afford 9 mg of compound I22 as a white solid. LCMS: $[M+H]^+$=471.2. $^1$H NMR (300 MHz, DMSO-$d_6$) δ 13.26 (s, 1H), 9.96 (s, 1H), 9.05 (s, 1H), 8.64 (s, 1H), 8.31 (s, 1H), 8.12 (s, 1H), 7.95-7.84 (m, 3H), 7.62 (d, J=8.0 Hz, 1H), 6.97 (d, J=8.4 Hz, 1H), 4.35 (s, 1H), 3.84 (s, 3H), 2.99-2.97 (m, 4H), 1.65-1.62 (m, 4H), 1.19 (s, 3H).

The following compounds can be prepared using general method B and similar methods with example 4 of synthesizing compound I22:

6-(1H-indazol-6-yl)-N-(4-morpholino-3-(trifluoromethoxy)phenyl)-[1,2,4]triazolo[1,5-a]pyrazin-8-amine (I20) was obtained as a white solid (0.023 g). LCMS: $[M+H]^+$=497.1. $^1$H NMR (300 MHz, DMSO-$d_6$) δ 12.24 (s, 1H), 10.32 (s, 1H), 9.10 (s, 1H), 8.56 (s, 1H), 8.35-8.06 (m, 4H), 7.85 (s, 2H), 7.24 (d, J=9.0 Hz, 1H), 3.79-3.71 (m, 4H), 3.34-3.26 (m, 4H).

N-(3-(difluoromethoxy)-4-morpholinophenyl)-6-(1H-indazol-6-yl)-[1,2,4]triazolo[1,5-a]pyrazin-8-amine (I21) was obtained as a white solid (0.045 g) LCMS: $[M+H]^+$=479.1. $^1$H NMR (300 MHz, DMSO-$d_6$) δ 13.21 (s, 1H), 10.25 (s, 1H), 9.10 (s, 1H), 8.66 (s, 1H), 8.25 (s, 1H), 8.12 (s, 1H), 8.10-7.82 (m, 5H), 7.17 (d, J=8.7 Hz, 1H), 7.14 (t, J=74.7 Hz, 1H), 3.77-3.73 (m, 4H), 3.04-3.76 (m, 4H).

1-(4-((6-(1H-indazol-6-yl)-[1,2,4]triazolo[1,5-a]pyrazin-8-yl)amino)phenyl)-4-methylpiperidin-4-ol (I23) was obtained as a white solid (0.009 g). LCMS: $[M+H^+]$=441.1. $^1$H NMR (400 MHz, DMSO-$d_6$) δ 13.10 (s, 1H), 9.91 (s, 1H), 9.01 (s, 1H), 8.62 (s, 1H), 8.29 (s, 1H), 8.11 (s, 1H), 7.96 (d, J=8.8 Hz, 1H), 7.85 (s, 3H), 7.02 (d, J=9.2 Hz, 1H), 4.29 (s, 1H), 3.39-3.34 (m, 2H), 3.17-3.12 (m, 4H), 1.60 (s, 3H), 1.21-1.16 (m, 2H).

4-(4-((6-(1H-indazol-6-yl)-[1,2,4]triazolo[1,5-a]pyrazin-8-yl)amino)-2-methoxyphenyl)thiomorpholine 1,1-dioxide (I24) was obtained as a white solid (0.050 g). LCMS: $[M+H^+]$=491.1. $^1$H NMR (300 MHz, DMSO-$d_6$) δ 10.07 (s, 1H), 9.08 (s, 1H), 8.65 (s, 1H), 8.30 (s, 1H), 8.12 (s, 1H), 8.08 (s, 1H), 7.88-7.86 (m, 2H), 7.63 (d, J=7.2 Hz, 1H), 7.07 (d, J=7.2 Hz, 1H), 3.87 (s, 3H), 3.45-3.39 (m, 4H), 3.26-3.16 (m, 4H).

4-(4-((6-(1H-indazol-6-yl)-[1,2,4]triazolo[1,5-a]pyrazin-8-yl)amino)phenyl)thiomorpholine 1,1-dioxide (I25) was obtained as a white solid (0.050 g). LCMS: $[M-H^+]$=459.0. $^1$H NMR (300 MHz, DMSO-$d_6$) § 10.01 (s, 1H), 9.04 (s, 1H), 8.63 (s, 1H), 8.27 (s, 1H), 8.11 (s, 1H), 8.04 (d, J=8.7 Hz, 2H), 7.85 (s, 2H), 7.12 (d, J=9.0 Hz, 2H), 3.81-3.68 (m, 4H), 3.21-3.11 (m, 4H).

7-(8-((3-methoxy-4-morpholinophenyl)amino)-[1,2,4]triazolo[1,5-a]pyrazin-6-yl)-2,2-dimethyl-2H-benzo[b][1,4]oxazin-3(4H)-one (I26) was obtained as a white solid (0.050 g). LCMS: $[M+H^+]$=502.2. $^1$H NMR (300 MHz, DMSO-$d_6$) δ 10.89 (s, 1H), 9.94 (s, 1H), 8.79 (s, 1H), 8.61 (s, 1H), 7.84-7.77 (m, 2H), 7.67-7.64 (m, 2H), 7.04 (d, J=9.0 Hz, 1H), 6.97 (d, J=9.0 Hz, 1H), 3.80 (s, 3H), 3.75-3.72 (m, 4H), 2.99-2.95 (m, 4H), 1.44 (s, 6H).

2,2-dimethyl-7-(8-((4-morpholinophenyl)amino)-[1,2,4]triazolo[1,5-a]pyrazin-6-yl)-2H-benzo[b][1,4]oxazin-3(4H)-one (I27) was obtained as a white solid (0.050 g). LCMS: $[M+H]^+$=472.1. $^1$H NMR (300 MHz, DMSO-$d_6$) δ 10.91 (s, 1H), 9.88 (s, 1H), 8.77 (s, 1H), 8.59 (s, 1H), 7.99 (d, J=8.4 Hz, 2H), 7.65 (s, 2H), 7.03 (d, J=8.4 Hz, 3H), 3.76-3.73 (m, 4H), 3.12-2.99 (m, 4H), 1.44 (s, 6H).

7-(8-((3-methoxy-4-morpholinophenyl)amino)-[1,2,4]triazolo[1,5-a]pyrazin-6-yl)-2H-benzo[b][1,4]oxazin-3(4H)-one (I28) was obtained as a white solid (0.050 g). LCMS: $[M+H]^+$=474.1. $^1$H NMR (300 MHz, DMSO-$d_6$) δ 11.00 (s, 1H), 9.98 (s, 1H), 8.81 (s, 1H), 8.62 (s, 1H), 7.83-7.77 (m, 2H), 7.66-7.64 (m, 2H), 7.05 (d, J=9.0 Hz, 1H), 6.96 (d, J=8.7 Hz, 1H), 4.64 (s, 2H), 3.80 (s, 3H), 3.79-3.72 (m, 4H), 2.99-2.95 (m, 4H).

7-(8-((4-morpholinophenyl)amino)-[1,2,4]triazolo[1,5-a]pyrazin-6-yl)-2H-benzo[b][1,4]oxazin-3(4H)-one (I29) was obtained as a white solid (0.050 g). LCMS (ESI-MS): $[M+H^+]$=444.2. $^1$H NMR (400 MHz, DMSO-$d_6$): δ 11.02 (s, 1H), 9.93 (s, 1H), 8.79 (s, 1H), 8.60 (s, 1H), 8.02-7.98 (d, J=11.2 Hz, 2H), 7.64-7.62 (d, J=9.6 Hz, 2H), 7.04-7.01 (m, 3H), 4.64 (s, 2H), 3.76 (s, 4H), 3.11 (s, 4H).

7-(8-((3-methoxy-4-morpholinophenyl)amino)-[1,2,4]triazolo[1,5-a]pyrazin-6-yl)-2H-pyrido[3,2-b][1,4]oxazin-3(4H)-one (I30) was obtained as a yellow solid (0.042 g). LCMS: $[M+H^+]$=475.2. $^1$H NMR (300 MHz, DMSO-$d_6$): δ 11.38 (s, 1H), 10.02 (s, 1H), 8.69 (s, 1H), 8.64 (s, 1H), 7.84-7.81 (m, 2H), 7.67 (d, J=8.1 Hz, 1H), 7.51 (d, J=8.1 Hz, 1H), 6.93 (d, J=9.0 Hz, 1H), 4.73 (s, 2H), 3.84 (s, 3H), 3.75-3.71 (m, 4H), 2.98-2.95 (m, 4H).

7-(8-((4-morpholinophenyl)amino)-[1,2,4]triazolo[1,5-a]pyrazin-6-yl)-2H-pyrido[3,2-b][1,4]oxazin-3(4H)-one (I31) was obtained as a white solid (0.022 g). LCMS: $[M+H^+]$=445.2. $^1$H NMR (300 MHz, DMSO-$d_6$) δ 11.49 (bs, 1H), 9.98 (s, 1H), 8.68 (s, 1H), 8.63 (s, 1H), 7.94 (d, J=8.4 Hz, 2H), 7.77 (d, J=8.1 Hz, 1H), 7.49 (d, J=8.1 Hz, 1H), 7.01 (d, J=8.4 Hz, 2H), 4.72 (s, 2H), 3.78-3.73 (m, 4H), 3.12-2.98 (m, 4H).

7-(8-((3-methoxy-4-morpholinophenyl)amino)-[1,2,4]triazolo[1,5-a]pyrazin-6-yl)-2,2-dimethyl-2H-pyrido[3,2-b][1,4]oxazin-3(4H)-one (I32) was obtained as a yellow solid (0.050 g). LCMS: $[M+H^+]$=503.2. $^1$H NMR (300 MHz, DMSO-$d_6$): δ 11.32 (s, 1H), 10.01 (s, 1H), 8.69 (s, 1H), 8.62 (s, 1H), 7.85-7.79 (m, 2H), 7.66 (d, J=8.7 Hz, 1H), 7.51 (d, J=8.1 Hz, 1H), 6.91 (d, J=8.7 Hz, 1H), 3.81 (s, 3H), 3.75-3.72 (m, 4H), 2.96-2.93 (m, 4H), 1.45 (s, 6H).

2,2-dimethyl-7-(8-((4-morpholinophenyl)amino)-[1,2,4]triazolo[1,5-a]pyrazin-6-yl)-2H-pyrido[3,2-b][1,4]oxazin-3(4H)-one (I33) was obtained as a yellow solid (0.041 g). LCMS: $[M+H^+]$=473.2. $^1$H NMR (300 MHz, DMSO-$d_6$) δ 11.69 (s, 1H), 10.34 (s, 1H), 9.05 (s, 1H), 8.99 (s, 1H), 8.30-8.14 (m, 3H), 7.88 (s, 1H), 7.37 (s, 2H), 4.13-4.10 (m, 4H), 3.48-3.44 (m, 4H), 1.83 (s, 6H).

7-(8-((3,4,5-trimethoxyphenyl)amino)-[1,2,4]triazolo[1,5-a]pyrazin-6-yl)-2H-pyrido[3,2-b][1,4]oxazin-3(4H)-one (I34) was obtained as a white solid (0.028 g). LCMS: $[M+H^+]$=450.1. $^1$H NMR (300 MHz, DMSO-$d_6$) δ 11.38 (s, 1H), 10.03 (s, 1H), 8.70 (s, 1H), 8.66 (s, 1H), 7.84 (d, J=7.5 Hz, 1H), 7.60-7.50 (m, 3H), 4.73 (s, 2H), 3.83 (s, 6H), 3.67 (s, 3H).

2,2-dimethyl-7-(8-((3,4,5-trimethoxyphenyl)amino)-[1,2,4]triazolo[1,5-a]pyrazin-6-yl)-2H-pyrido[3,2-b][1,4]oxazin-3(4H)-one (I35) was obtained as a yellow solid (0.055 g). LCMS: $[M+H^+]$=478.2. $^1$H NMR (300 MHz, DMSO-$d_6$) δ 11.33 (s, 1H), 10.02 (s, 1H), 8.71 (s, 1H), 8.64 (s, 1H), 7.86 (d, J=8.7 Hz, 1H), 7.58 (s, 1H), 7.55 (s, 1H), 7.53 (d, J=8.4 Hz, 1H), 3.82 (s, 6H), 3.65 (s, 3H), 1.46 (s, 6H).

7-(8-((3,4-dimethoxyphenyl)amino)-[1,2,4]triazolo[1,5-a]pyrazin-6-yl)-2H-pyrido[3,2-b][1,4]oxazin-3(4H)-one (I36) was obtained as a white solid (0.030 g). LCMS: $[M+H^+]$=420.1. $^1$H NMR (300 MHz, DMSO-$d_6$) δ 11.38 (s, 1H), 10.00 (s, 1H), 8.70 (s, 1H), 8.64 (s, 1H), 7.83 (s, 1H), 7.82 (d, J=7.5 Hz, 1H), 7.64 (d, J=8.1 Hz, 1H), 7.51 (d, J=7.8 Hz, 1H), 7.01 (d, J=8.7 Hz, 1H), 4.73 (s, 2H), 3.91 (s, 3H), 3.75 (s, 3H).

7-(8-((3,4-dimethoxyphenyl)amino)-[1,2,4]triazolo[1,5-a]pyrazin-6-yl)-2,2-dimethyl-2H-pyrido[3,2-b][1,4]oxazin-3(4H)-one (I37) was obtained as a yellow solid (0.040 g). LCMS: $[M+H^+]$=448.2. $^1$H NMR (300 MHz, DMSO-$d_6$) δ 11.31 (s, 1H), 9.97 (s, 1H), 8.67 (s, 1H), 8.62 (s, 1H), 7.84-7.80 (m, 2H), 7.62 (d, J=9.0 Hz, 1H), 7.51 (d, J=8.1 Hz, 1H), 6.98 (d, J=8.7 Hz, 1H), 3.85 (s, 3H), 3.76 (s, 3H), 1.45 (s, 6H).

7-(8-((2,2-difluorobenzo[d][1,3]dioxol-5-yl)amino)-[1,2,4]triazolo[1,5-a]pyrazin-6-yl)-2H-pyrido[3,2-b][1,4]oxazin-3(4H)-one (I38) was obtained as a white solid (0.022 g). LCMS: $[M+H^+]$=440.0. $^1$H NMR (300 MHz, DMSO-$d_6$) δ 11.35 (s, 1H), 10.36 (s, 1H), 8.71 (s, 1H), 8.63 (s, 1H), 8.13 (s, 1H), 7.86 (d, J=8.7 Hz, 1H), 7.67 (d, J=8.7 Hz, 1H), 7.48 (d, J=8.7 Hz, 1H), 7.41 (d, J=8.1 Hz, 1H), 4.69 (s, 2H).

7-(8-((2,2-difluorobenzo[d][1,3]dioxol-5-yl)amino)-[1,2,4]triazolo[1,5-a]pyrazin-6-yl)-2,2-dimethyl-2H-pyrido[3,2-b][1,4]oxazin-3(4H)-one (I39) was obtained as a yellow solid (0.022 g). LCMS: $[M+H^+]$=468.2. $^1$H NMR (300 MHz, DMSO-$d_6$) δ 11.34 (s, 1H), 10.39 (s, 1H), 8.76 (s, 1H), 8.67 (s, 1H), 8.16 (s, 1H), 7.91 (d, J=9.0 Hz, 1H), 7.74 (d, J=8.1 Hz, 1H), 7.53 (d, J=8.1 Hz, 1H), 7.45 (d, J=8.7 Hz, 1H), 1.47 (s, 6H).

6-(3H-indol-6-yl)-N-(3-methoxy-4-(2-oxa-6-azaspiro[3.3]heptan-6-yl)phenyl)-[1,2,4]triazolo[1,5-a]pyrazin-8-amine (I62) was obtained as a yellow solid (0.082 g). LC-MS: 454.2 [M+H]. $^1$H NMR (400 MHz, DMSO-$d_6$) δ: 11.28 (brs, 1H), 9.79 (s, 1H), 8.84 (s, 1H), 8.58 (s, 1H), 8.16 (s, 1H), 7.93 (s, 1H), 7.75 (dd, J=1.2, 8.0 Hz, 1H), 7.63-7.58 (m, 2H), 7.43 (t, J=2.4 Hz, 1H), 6.45 (d, J=8.8 Hz, 2H), 4.71 (s, 4H), 3.98 (s, 4H), 3.80 (s, 3H).

N-(4-(2-oxa-6-azaspiro[3.4]octan-6-yl)phenyl)-6-(1H-indol-6-yl)-[1,2,4]triazolo[1,5-a]pyrazin-8-amine (I64) was obtained as a yellow solid (0.078 g). LC-MS: 438 $[M+H]^+$. $^1$H NMR (400 MHz, DMSO-$d_6$) δ: 11.34 (s, 1H), 9.78 (s, 1H), 8.85 (s, 1H), 8.59 (s, 1H), 8.19 (s, 1H), 7.99 (d, J=11.6 Hz, 2H), 7.77-7.74 (m, 1H), 7.65 (d, J=11.2 Hz, 1H), 7.46 (t, J=3.6 Hz, 1H), 6.68 (d, J=11.6 Hz, 2H), 6.50 (s, 1H), 4.65 (d, J=8.0 Hz, 2H), 4.59 (d, J=8.0 Hz, 2H), 3.56 (s, 2H), 3.32 (t, J=9.2 Hz, 2H), 2.31 (t, J=8.8 Hz, 2H).

6-(1H-indol-5-yl)-N-(4-((1S,4R)-5-isopropyl-2,5-diazabicyclo[2.2.1]heptan-2-yl)phenyl)-[1,2,4]triazolo[1,5-a]pyrazin-8-amine (I70) was obtained as a yellow solid (0.072 g). LC-MS: 465 $[M+H]^+$. $^1$H NMR (400 MHz, DMSO-$d_6$) δ: 11.22 (s, 1H), 9.81 (d, J=4.4 Hz, 1H), 8.81 (d, J=1.6 Hz, 1H), 8.57 (s, 1H), 8.29 (s, 1H), 8.06-8.00 (m, 2H), 7.85-7.82 (m, 1H), 7.49 (d, J=8.8 Hz, 1H), 7.41-7.40 (m, 1H), 6.80-6.77 (m, 2H), 6.52 (s, 1H), 4.66 (d, J=13.2 Hz, 2H), 3.70-3.60 (m, 2H), 3.56-3.45 (m, 2H), 3.40-3.37 (m, 1H), 2.30-2.24 (m, 1H), 2.17-2.09 (m, 1H), 1.35 (d, J=6.0 Hz, 2H), 1.30 (d, J=6.4 Hz, 1H), 1.24-1.19 (m, 3H).

6-(1H-indol-6-yl)-N-(4-((1S,4R)-5-isopropyl-2,5-diazabicyclo[2.2.1]heptan-2-yl)phenyl)-[1,2,4]triazolo[1,5-a]pyrazin-8-amine (I72) was obtained as a yellow solid (0.091 g). LC-MS: 465 $[M+H]^+$. $^1$H NMR (400 MHz, DMSO-$d_6$) δ: 11.22 (s, 1H), 9.81 (d, J=4.4 Hz, 1H), 8.81 (d, J=1.6 Hz, 1H), 8.57 (s, 1H), 8.29 (s, 1H), 8.06-8.00 (m, 2H), 7.85-7.82 (m, 1H), 7.49 (d, J=8.8 Hz, 1H), 7.41-7.40 (m, 1H), 6.80-6.77 (m, 2H), 6.52 (s, 1H), 4.66 (d, J=13.2 Hz, 2H), 3.70-3.60 (m, 2H), 3.56-3.45 (m, 2H), 3.40-3.37 (m, 1H), 2.30-2.24 (m, 1H), 2.17-2.09 (m, 1H), 1.35 (d, J=6.0 Hz, 2H), 1.30 (d, J=6.4 Hz, 1H), 1.24-1.19 (m, 3H).

Example 5. N-(3-fluoro-4-morpholinophenyl)-6-(1H-indazol-6-yl)-[1,2,4]triazolo[4,3-a]pyrazin-8-amine (I40)

A 100 mL round-bottom flask purged and maintained under an inert atmosphere of nitrogen for 3 times, was placed compound 59 (300 mg, 0.76 mmol), 6-(4,4,5,5-tetramethyl-1,3,2-dioxaborolan-2-yl)-1H-indazole (200 mg, 0.8 mmol), $Na_2CO_3$ (230 mg, 2.1 mmol), $Pd(PPh_3)_4$ (80 mg, 0.07 mmol), 1,4-dioxane (10 mL) and water (1 mL). The resulting mixture was heated at 100° C. under inert atmosphere for 10 h. The reaction mixture was diluted with water and extracted with EtOAc. The combined organic layers were dried over anhydrous $Na_2SO_4$ and concentrated in vacuum. The residue was purified by flash column chromatography on silica gel with 20% MeOH in DCM to afford 11.6 mg of compound I40 as a white solid. LCMS: $[M+H]^+$= 431.2. $^1H$ NMR (300 MHz, DMSO-$d_6$) δ 13.2 (s, 1H), 10.41 (s, 1H), 9.29 (s, 1H), 8.63 (s, 1H), 8.13-8.07 (m, 3H), 7.96-7.84 (m, 2H), 7.68 (d, J=8.4 Hz, 1H), 7.11 (d, J=9.9 Hz, 1H), 3.77-3.73 (m, 4H), 3.03-2.96 (m, 4H).

The following compounds can be prepared using general method C and similar methods with example 5 of synthesizing compound I40:

N-(3-chloro-4-morpholinophenyl)-6-(1H-indazol-6-yl)-[1,2,4]triazolo[4,3-a]pyrazin-8-amine (I41) was obtained as a white solid (0.040 g). LCMS: $[M+H]^+$=447.2. $^1H$ NMR (300 MHz, DMSO-$d_6$) δ 10.44 (s, 1H), 9.29 (s, 1H), 8.64 (s, 1H), 8.37 (s, 1H), 8.13-8.08 (m, 3H), 7.85 (d, J=8.7 Hz, 1H), 7.69 (d, J=8.7 Hz, 1H), 7.22 (d, J=8.7 Hz, 1H), 3.76-3.72 (m, 4H), 3.04-2.98 (m, 4H).

6-(1H-indazol-6-yl)-N-(3-methyl-4-morpholinophenyl)-[1,2,4]triazolo[4,3-a]pyrazin-8-amine (I42) was obtained as a white solid (0.011 g). LCMS: $[M+H]^+$=427.2. $^1H$ NMR (400 MHz, DMSO-$d_6$) δ 13.28 (s, 1H), 10.17 (s, 1H), 9.30 (s, 1H), 8.64 (s, 1H), 8.20-7.11 (m, 6H), 7.11 (d, J=8.4 Hz, 1H), 3.79-3.75 (m, 4H), 2.91-2.86 (m, 4H), 2.36 (s, 3H).

6-(1H-indazol-6-yl)-N-(6-morpholinopyridin-3-yl)-[1,2,4]triazolo[4,3-a]pyrazin-8-amine (I43) was obtained as a white solid (0.010 g). LCMS: $[M+H]^+$=414.2. $^1H$ NMR (300 MHz, DMSO-$d_6$) δ 10.23 (s, 1H), 9.26 (s, 1H), 8.83 (s, 1H), 8.56 (s, 1H), 8.23 (d, J=9.9 Hz, 1H), 8.07 (m, 2H), 7.82 (d, J=8.4 Hz, 2H), 7.65 (d, J=8.4 Hz, 1H), 6.91 (d, J=9.3 Hz, 1H), 3.73-3.68 (m, 4H), 3.16-3.08 (m, 4H).

6-(3-fluoro-1H-indazol-6-yl)-N-(3-methoxy-4-morpholinophenyl)-[1,2,4]triazolo[4,3-a]pyrazin-8-amine (I44) was obtained as a yellow solid (0.0087 g). LCMS: $[M+H^+]$= 461.2. $^1H$ NMR (300 MHz, DMSO-$d_6$): (s, 1H), δ 10.22 (s, 1H), 9.27 (s, 1H), 8.64 (s, 1H), 8.10 (s, 1H), 7.96 (s, 1H), 7.77 (s, 1H), 7.63-7.60 (m, 2H), 7.61 (d, J=7.2 Hz, 1H), 6.91 (d, J=8.4 Hz, 1H), 3.80 (s, 3H), 3.72-3.68 (m, 4H), 2.97-2.93 (m, 4H).

6-(3-fluoro-1H-indazol-6-yl)-N-(4-morpholinophenyl)-[1,2,4]triazolo[4,3-a]pyrazin-8-amine (I45) was obtained as a white solid (0.022 g). LCMS: $[M+H]^+$=431.1. $^1H$ NMR (300 MHz, DMSO-$d_6$) δ 12.73 (s, 1H), 10.21 (s, 1H), 9.30 (s, 1H), 8.66 (s, 1H), 8.12 (s, 1H), 8.00 (d, J=6.6 Hz, 2H), 7.82-7.75 (m, 2H), 7.03 (d, J=6.9 Hz, 2H), 3.80-3.76 (m, 4H), 2.93-2.89 (m, 4H).

N-(3-methoxy-4-morpholinophenyl)-6-(3-methyl-1H-indazol-6-yl)-[1,2,4]triazolo[4,3-a]pyrazin-8-amine (I46) was obtained as a white solid (0.014 g). LCMS: $[M+H]^+$=457.2. $^1H$ NMR (300 MHz, DMSO-$d_6$) δ 10.22 (s, 1H), 9.27 (s, 1H), 8.60 (s, 1H), 8.10 (s, 1H), 8.05 (d, J=8.4 Hz, 1H), 7.78-7.63 (m, 3H), 3.83 (s, 3H), 3.76-3.72 (m, 4H), 3.02-2.96 (m, 4H), 1.20 (s, 3H).

N-(3-methoxy-4-morpholinophenyl)-6-(3-methyl-1H-indol-6-yl)-[1,2,4]triazolo[4,3-a]pyrazin-8-amine (I47) was obtained as a yellow solid (0.014 g). LCMS: $[M+H^+]$=456.2. $^1H$ NMR (300 MHz, DMSO-$d_6$): (s, 1H), 10.11 (s, 1H), 9.24 (s, 1H), 8.46 (s, 1H), 8.06 (d, J=8.1 Hz, 1H), 8.01 (s, 1H), 7.69-7.52 (m, 3H), 7.17 (s, 1H), 6.92 (d, J=8.4 Hz, 1H), 3.82 (s, 3H), 3.73-3.69 (m, 4H), 2.97-2.93 (m, 4H), 2.26 (s, 3H).

I48: 6-(1H-indazol-6-yl)-N-(4-morpholinophenyl)-[1,2,4]triazolo[4,3-a]pyrazin-8-amine.

6-(1H-indol-5-yl)-N-(4-morpholinophenyl)-[1,2,4]triazolo[4,3-a]pyrazin-8-amine (I66) was obtained as a yellow solid (0.012 g). LC-MS: 412 $[M+H]^+$. $^1H$ NMR (400 MHz, $CD_3OD$) δ: 9.21 (s, 1H), 8.36 (s, 1H), 8.20-8.18 (m, 2H), 8.12 (s, 1H), 7.66 (s, 2H), 7.40-7.35 (m, 3H), 6.52 (d, J=3.6 Hz, 1H), 4.00 (t, J=4.8 Hz, 4H), 3.46 (d, J=4.8 Hz, 4H).

6-(1H-indol-5-yl)-N-(3-methoxy-4-morpholinophenyl)-[1,2,4]triazolo[4,3-a]pyrazin-8-amine (I68) was obtained as a yellow solid (0.035 g). LC-MS 442 $[M+H]^+$. $^1H$ NMR (400 MHz, DMSO-$d_6$) δ: 11.39 (s, 1H), 10.14 (s, 1H), 9.30 (s, 1H), 8.51 (s, 1H), 8.08 (t, J=4.8 Hz, 2H), 7.72-7.69 (m, 1H), 7.63 (s, 2H), 7.43 (t, J=2.4 Hz, 1H), 6.95 (t, J=8.8 Hz, 1H), 6.47 (s, 1H), 3.85 (s, 3H), 3.75 (t, J=4.6 Hz, 4H), 2.98 (t, J=4.4 Hz, 4H).

Example 6. 6-(1H-indazol-6-yl)-N-(4-(4-(oxetan-3-yl)piperazin-1-yl)phenyl)-[1,2,4]triazolo[1,5-a]pyrazin-8-amine (I53)

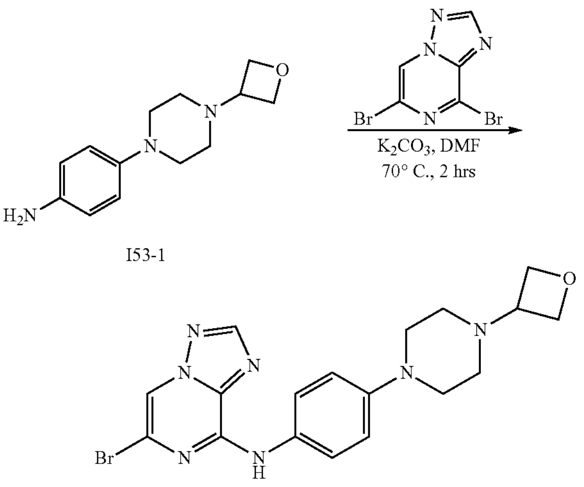

I53-1

I53-2

To a solution of compound I53-1 (215.0 mg, 0.92 mmol) in DMF (10 mL) was added 6,8-dibromo-[1,2,4]triazolo[1,5-a]pyrazine (282.0 mg, 1.02 mmol) and $K_2CO_3$ (382.0 mg, 2.77 mmol). The reaction mixture was stirred at 70° C. for 2 h. The reaction mixture was cooled to rt, diluted with $H_2O$, and stirred for 30 min at rt. The solid was collected by filtration and washed with water, dried in vacuum to give compound I53-2 (345.0 mg) as a yellow solid. The crude was used into the following reaction without the further purification. LCMS: 432.3 $[M+H]^+$.

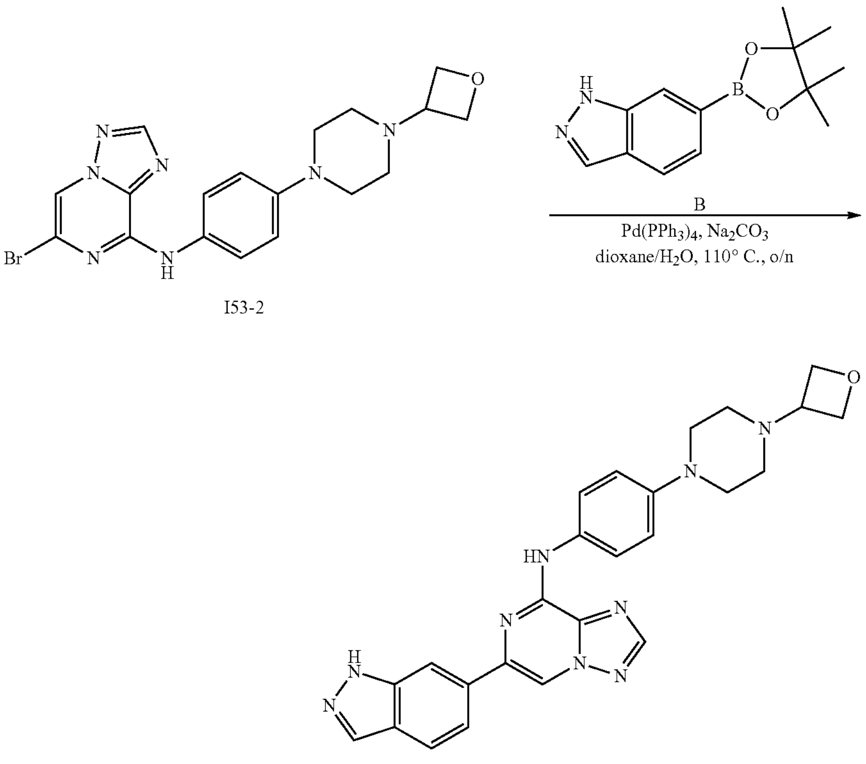

I53-2

I53

To a solution of compound I53-2 (100.0 mg, 0.23 mmol) in Dioxane/$H_2O$ (10/1 mL) was added compound B (85.0 mg, 0.35 mmol), $Na_2CO_3$ (96.0 mg, 0.69 mmol) and $Pd(PPh_3)_4$ (27.0 mg, 0.02 mmol). The reaction mixture was stirred at 110° C. and stirred overnight. Then the mixture was poured into 30 mL of water and the product was extracted with EA. The combined organic layer was concentrated in vacuum. The residue was purified by prep-HPLC to give compound I53 (56.0 mg) as a yellow solid. LCMS: 468.0 $[M+H]^+$. $^1H$ NMR (400 MHz, DMSO-$d_6$) δ: 13.23 (brs, 1H), 9.93 (s, 1H), 9.02 (s, 1H), 8.62 (s, 1H), 8.28 (s, 1H), 8.10 (s, 1H), 7.98 (d, J=8.8 Hz, 2H), 7.85 (s, 2H), 7.02 (d, J=9.2 Hz, 2H), 4.58 (t, J=6.4 Hz, 2H), 4.49 (t, J=6.0 Hz, 2H), 3.50-3.44 (m, 1H), 3.18 (s, 4H), 2.44 (s, 4H).

Example 7. 6-(1H-indazol-6-yl)-N-(3-methoxy-4-(4-(oxetan-3-yl)piperazin-1-yl)phenyl)-[1,2,4]triazolo[1,5-a]pyrazin-8-amine (I54)

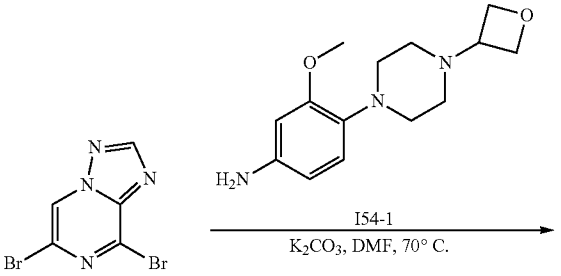

-continued

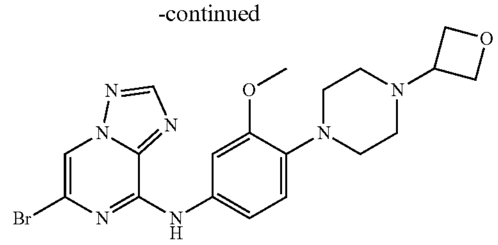

I54-2

To a solution of 6,8-dibromo-[1,2,4]triazolo[1,5-a]pyrazine (1.26 g, 4.53 mmol) in DMF (20 mL) was added $K_2CO_3$ (1.57 g, 11.38 mmol) and compound I54-1 (1 g, 3.80 mmol). The mixture was stirred at 50° C. for 1 h. The reaction mixture was diluted with $H_2O$ and extracted with EA. The combined organic layers were washed with brine, dried over $Na_2SO_4$, filtered and concentrated. The residue was purified by silica gel chromatography (DCM/MeOH=15%) to give compound I54-2 (1.5 g) as a yellow solid LCMS: 460 $[M+H]^+$.

Using the similar reaction conditions of synthesizing compound I22, and using compound I54-2 and compound B, compound I54 was obtained as a yellow solid (0.030 g). LC-MS: 498 $[M+H]^+$.$^1H$ NMR (400 MHz, DMSO-$d_6$) δ: 13.26 (s, 1H), 9.99 (s, 1H), 9.05 (s, 1H), 8.64 (s, 1H), 8.30 (s, 1H), 8.11 (s, 1H), 8.01 (d, J=1.6 Hz, 1H), 7.88 (d, J=5.6 Hz, 2H), 7.63-7.61 (m, 1H), 6.96 (d, J=8.4 Hz, 1H), 4.57 (t, J=6.8 Hz, 2H), 4.48 (t, J=6.0 Hz, 2H), 3.84 (s, 3H), 3.50-3.47 (m, 1H), 3.02 (s, 4H), 2.43 (s, 4H).

Example 8. 6-(6-aminopyrazin-2-yl)-N-(4-(4-(oxetan-3-yl)piperazin-1-yl)phenyl)-[1,2,4]triazolo[1,5-a]pyrazin-8-amine (I55)

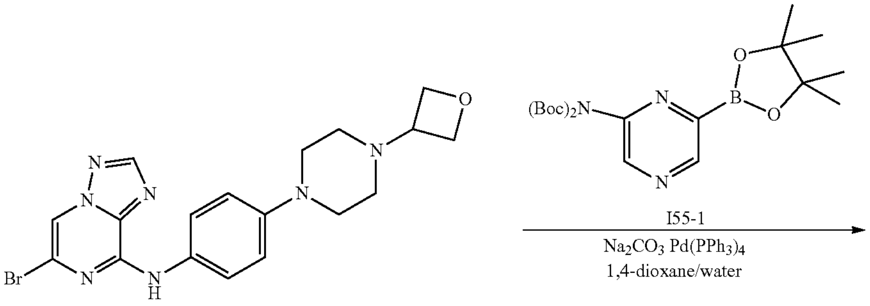

I53-2

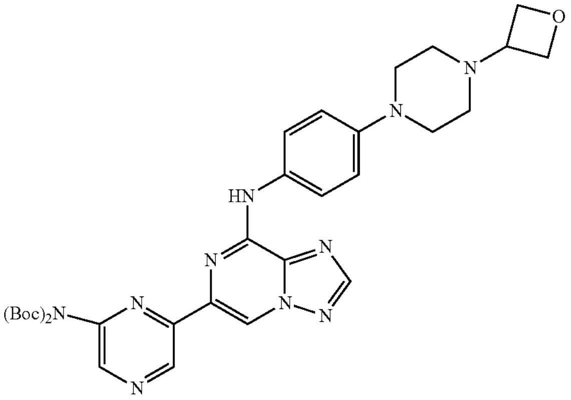

I55-2

To a 50-mL round-bottom flask was placed compound I53-2 (200 mg, 0.46 mmol), compound I55-1 (391.6 mg, 0.93 mmol), $Na_2CO_3$ (147.9 mg, 1.40 mmol), $Pd(PPh_3)_4$ (53.7 mg, 0.046 mmol), 1,4-dioxane (5 mL) and water (1 mL). The resulting mixture was heated at 100° C. under $N_2$ atmosphere for 2 h. The reaction mixture was diluted with water and extracted with EA. The combined organic layers were dried over anhydrous $Na_2SO_4$ and concentrated in vacuum. The residue was purified by silica gel chromatography (MeOH/DCM=1%-4%) to give compound I55-2 (110 mg) as a yellow solid. LC-MS: 645 $[M+H]^+$.

To a solution of compound I55-2 (135 mg, 0.27 mmol) in DCM (5 mL) was added trifluoroacetic acid (5 mL). The reaction mixture was stirred at rt for 3 h. Then the reaction mixture was concentrated and the residue was purified by prep-HPLC to afford compound I55 (75.5 mg) as a yellow solid. LCMS: 445 $[M+H]^+$. $^1$H NMR (400 MHz, DMSO-$d_6$) δ: 9.98 (s, 1H), 8.71 (s, 1H), 8.64 (s, 1H), 8.49 (s, 1H), 7.94 (s, 2H), 7.92 (s, 1H), 7.02 (d, J=9.2 Hz, 2H), 6.61 (s, 2H), 4.58 (t, J=6.2 Hz, 2H), 4.49 (t, J=5.4 Hz, 2H), 3.46 (s, 1H).

Example 9. 6-(6-aminopyrazin-2-yl)-N-(3-methoxy-4-(4-(oxetan-3-yl)piperazin-1-yl)phenyl)-[1,2,4]triazolo[1,5-a]pyrazin-8-amine (I56)

Using the similar reaction conditions of synthesizing compound I55-2, and using compound I54-2 and compound I55-1, compound I56-2 was obtained as a yellow solid (0.11 g) after purification by silica gel chromatography (MeOH/DCM=1%-4%). LCMS: 675 $[M+H]^+$.

Using the similar reaction conditions of synthesizing compound I55, and using compound I56-2, compound I56 was obtained as a yellow solid (0.075 g). LCMS: 475 $[M+H]^+$. $^1$H NMR (400 MHz, DMSO-$d_6$) δ: 8.74 (s, 1H), 8.66 (s, 1H), 8.55 (s, 1H), 7.95 (s, 1H), 7.85 (d, J=2.0 Hz, 1H), 7.66-7.64 (m, 1H), 6.97 (d, J=8.8 Hz, 1H), 6.63 (s, 2H), 4.56 (t, J=6.8 Hz, 2H), 4.48 (t, J=6.0 Hz, 2H), 3.85 (s, 3H), 3.49-3.46 (m, 1H), 3.0 (s, 4H), 2.42 (s, 4H).

Example 10. 6-(1H-indol-6-yl)-N-(4-(4-(oxetan-3-yl)piperazin-1-yl)phenyl)-[1,2,4]triazolo[1,5-a]pyrazin-8-amine (I57)

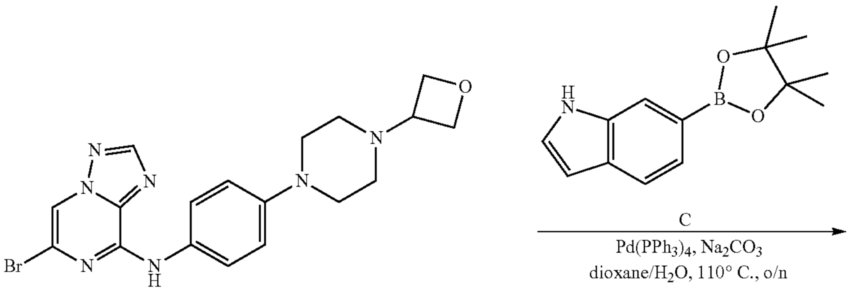

I53-2

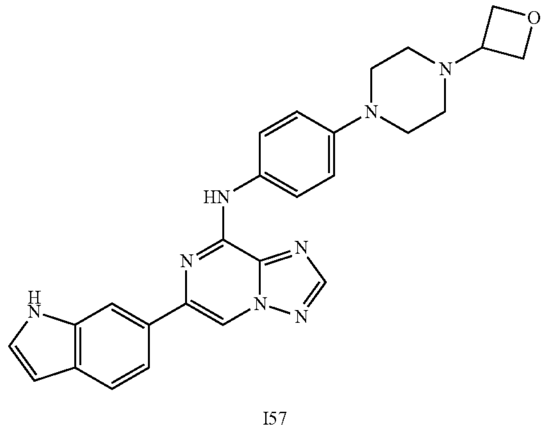

I57

To a solution of compound I53-2 (200.0 mg, 0.47 mmol) in Dioxane/$H_2O$ (10/1 mL) was added compound C (226.0 mg, 0.93 mmol), $Na_2CO_3$ (148.0 mg, 1.39 mmol) and $Pd(PPh_3)_4$ (54.0 mg, 0.05 mmol). The reaction mixture was stirred at 110° C. and stirred overnight. The reaction mixture was completed detected by LCMS. Then the mixture was poured into 30 mL of water and the product was extracted with EA. The combined organic layer was concentrated in vacuum. The residue was purified by prep-HPLC to give compound I57 (85.0 mg) as a yellow solid. LCMS: 467.1 $[M+H]^+$. $^1H$ NMR (400 MHz, DMSO-$d_6$) δ: 11.35 (brs, 1H), 9.85 (s, 1H), 8.85 (s, 1H), 8.58 (s, 1H), 8.17 (s, 1H), 8.02 (d, J=9.2 Hz, 2H), 7.72 (dd, J=1.6, 8.4 Hz, 1H), 7.61 (d, J=8.4 Hz, 1H), 7.43 (t, J=2.8 Hz, 1H), 7.03 (d, J=9.2 Hz, 2H), 6.47 (s, 1H), 4.58 (t, J=6.4 Hz, 2H), 4.49 (t, J=5.2 Hz, 2H), 3.48-3.46 (m, 1H), 3.18 (s, 4H), 2.44 (s, 4H).

Example 11. 6-(1H-indol-6-yl)-N-(3-methoxy-4-(4-(oxetan-3-yl)piperazin-1-yl)phenyl)-[1,2,4]triazolo[1,5-a]pyrazin-8-amine (I58)

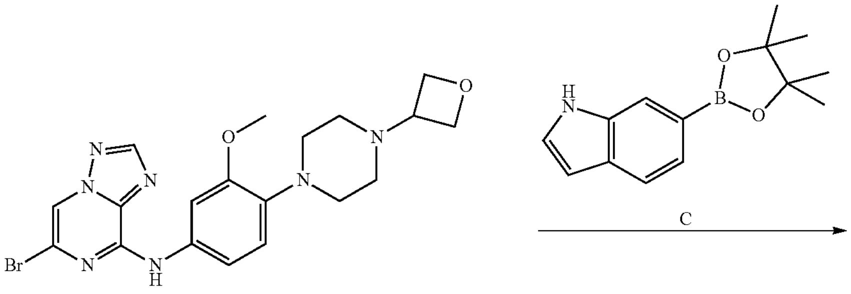

I54-2

-continued

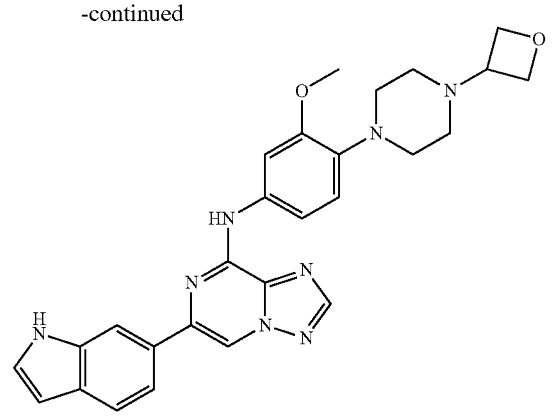

I58

To a solution of compound I54-2 (300 mg, 0.65 mmol) in Dioxane/$H_2O$ (20 mL/5 mL) was added compound C (238 mg, 0.98 mmol) and $Na_2CO_3$ (138 mg, 1.3 mmol) and $Pd(PPh_3)_4$ (75 mg, 0.07 mmol). The reaction mixture was stirred at 100° C. overnight. The reaction was diluted with $H_2O$ and extracted with EA. The combined organic layers were washed with brine, dried over $Na_2SO_4$, filtered and concentrated. The residue was purified by flash chromatography on silica gel (EA) to afford crude of product. The residue was further purified by prep-HPLC to afford compound I58 (144 mg) as a yellow solid. LCMS: 497 $[M+H]^+$. $^1H$ NMR (400 MHz, DMSO-$d_6$) δ: 11.29 (s, 1H), 9.91 (s, 1H), 8.88 (s, 1H), 8.60 (s, 1H), 8.18 (s, 1H), 8.03 (s, 1H), 7.76 (d, J=7.2 Hz, 1H), 7.67-7.61 (m, 2H), 7.43-7.42 (m, 1H), 6.95 (d, J=8.8 Hz, 1H), 6.48 (s, 1H), 4.57 (d, J=6.4 Hz, 2H), 4.50-4.47 (m, 2H), 3.84 (s, 3H), 3.51-3.44 (m, 1H), 3.02 (s, 4H), 2.42 (s, 4H).

Example 12. N-(4-(2-oxa-6-azaspiro[3.3]heptan-6-yl)phenyl)-6-(1H-indazol-6-yl)-[1,2,4]triazolo[1,5-a]pyrazin-8-amine (I59)

Step 1 Synthesis of Compound I59-2

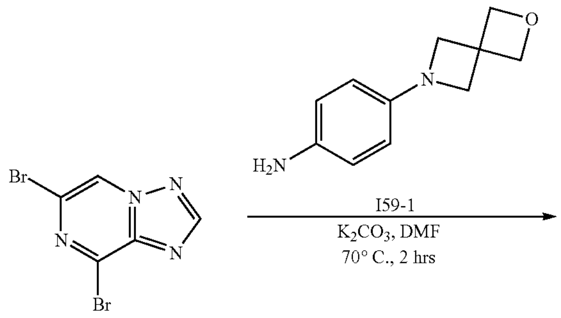

-continued

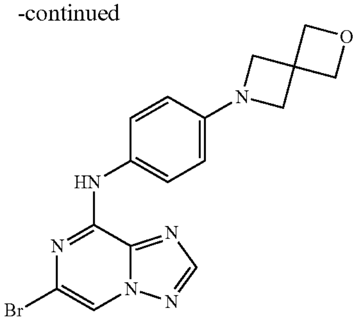

I59-2

To a solution of compound I59-1 (400.0 mg, 2.10 mmol) in DMF (15 mL) was added 6,8-dibromo-[1,2,4]triazolo[1,5-a]pyrazine (702.0 mg, 2.52 mmol) and $K_2CO_3$ (871.0 mg, 6.31 mmol). The reaction mixture was stirred at 70° C. for 2 hours. The reaction mixture was cooled to room temperature, diluted with $H_2O$ (30 mL) and stirred for 30 minutes at room temperature. The solid was collected by filtration and washed with water, dried in vacuum to give compound I59-2 (900.0 mg, crude) as a gray solid. The crude was used into the following reaction without the further purification. LC-MS: 389.3 $[M+H]^+$.

Step 2 Synthesis of Compound I59

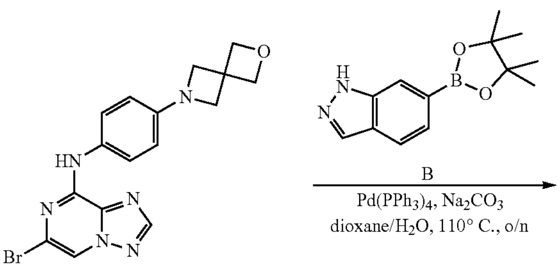

I59-2

-continued

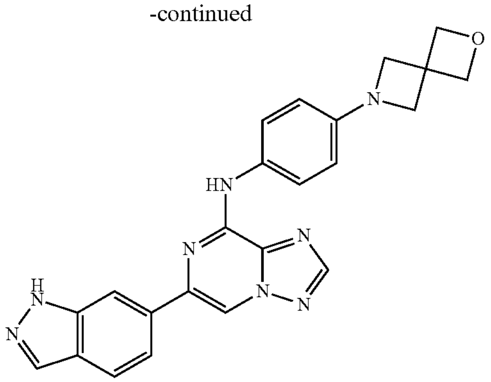

I59

To a solution of compound I59-2 (200.0 mg, 0.52 mmol) in Dioxane/$H_2O$ (20/4 mL) was added compound B (252.0 mg, 1.03 mmol), $Na_2CO_3$ (164.0 mg, 1.55 mmol) and $Pd(PPh_3)_4$ (60.0 mg, 0.05 mmol). The reaction mixture was stirred at 110° C. and stirred overnight. The reaction mixture was completed detected by LCMS. Then the mixture was poured into 30 ml of water and the product was extracted with EA. The combined organic layer was concentrated in vacuum. The residue was purified by prep.-HPLC to give compound I59 (30.0 mg, 13.7% yield) as a yellow solid. LC-MS: 425.2 $[M+H]^+$. $^1H$ NMR (400 MHz, DMSO-$d_6$) δ: 13.24 (brs, 1H), 9.85 (s, 1H), 8.99 (s, 1H), 8.61 (s, 1H), 8.25 (s, 1H), 8.10 (s, 1H), 7.91 (d, J=8.8 Hz, 2H), 7.84 (s, 2H), 6.53 (d, J=9.2 Hz, 2H), 4.4.74 (s, 4H), 3.99 (s, 4H).

Example 13. 6-(1H-indazol-6-yl)-N-(3-methoxy-4-(2-oxa-6-azaspiro[3.3]heptan-6-yl)phenyl)-[1,2,4]triazolo[1,5-a]pyrazin-8-amine (I60)

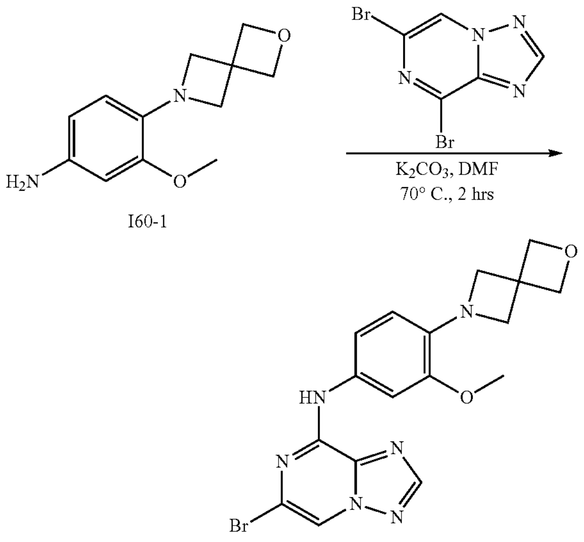

I60-1

I60-2

To a solution of compound I60-1 (530.0 mg, 2.41 mmol) in DMF (20 mL) was added 6,8-dibromo-[1,2,4]triazolo[1,5-a]pyrazine (737.0 mg, 2.65 mmol) and $K_2CO_3$ (997.0 mg, 7.23 mmol). The reaction mixture was stirred at 70° C. for 2 h. The reaction mixture was cooled to rt, diluted with $H_2O$, and stirred for 30 min at rt. The solid was collected by filtration and washed with water, dried in vacuum to give compound I60-2 (750 mg) as a yellow solid. The crude was used into the following reaction without the further purification. LCMS: 419.0 $[M+H]^+$.

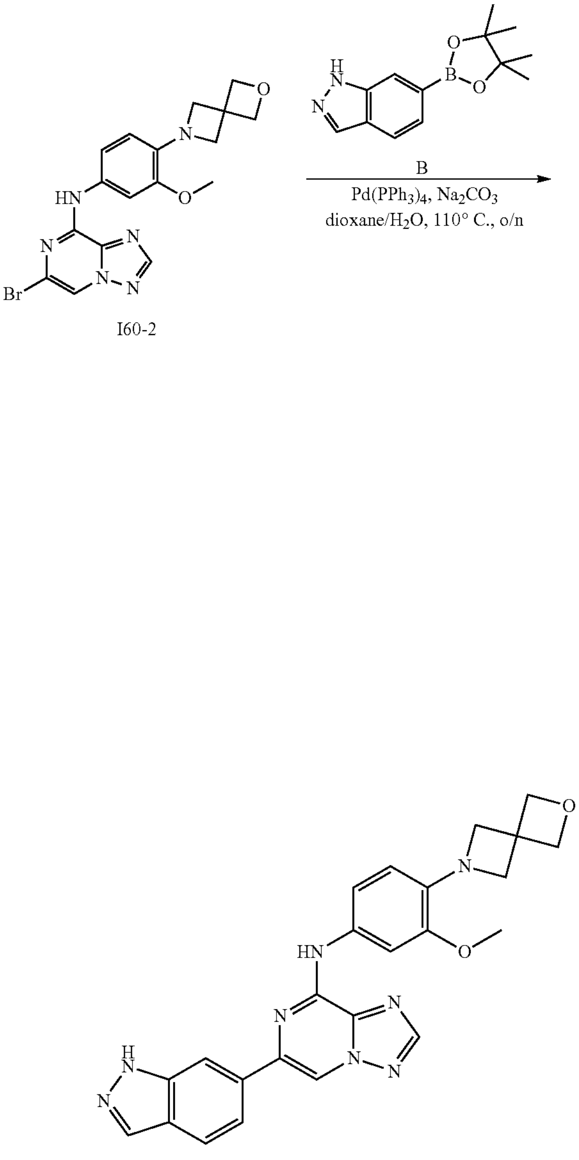

I60-2

I60

To a solution of compound I60-2 (200.0 mg, 0.48 mmol) in Dioxane/$H_2O$ (30/6 mL) was added compound B (175.0 mg, 0.72 mmol), $Na_2CO_3$ (152.0 mg, 1.44 mmol) and $Pd(PPh_3)_4$ (55.0 mg, 0.05 mmol). The reaction mixture was stirred at 110° C. and stirred overnight. The reaction mixture was completed detected by LCMS. Then the mixture was poured into 30 ml of water and the product was extracted with EA. The combined organic layer was concentrated in vacuum. The residue was purified by prep-HPLC to give compound I60 (45.0 mg) as a yellow solid. LCMS: 455.2 $[M+H]^+$. $^1H$ NMR (400 MHz, DMSO-$d_6$) δ: 13.25 (brs, 1H), 9.87 (s, 1H), 9.00 (s, 1H), 8.62 (s, 1H), 8.27 (s, 1H), 8.11 (s, 1H), 7.89-7.83 (m, 3H), 7.56 (dd, J=2.0, 8.4 Hz, 1H), 6.45 (d, J=8.4 Hz, 1H), 4.72 (s, 4H), 3.98 (s, 4H), 3.80 (s, 3H).

Example 14. N-(4-(2-oxa-6-azaspiro[3.3]heptan-6-yl)phenyl)-6-(1H-indol-6-yl)-[1,2,4]triazolo[1,5-a]pyrazin-8-amine (I61)

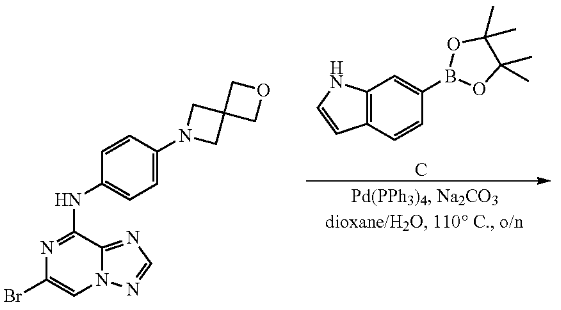

I59-2

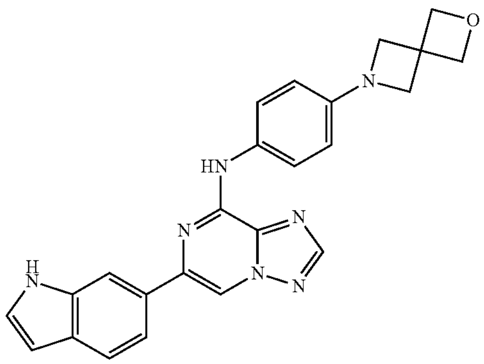

I61

To a solution of compound I59-2 (300.0 mg, 0.77 mmol) in Dioxane/$H_2O$ (30/5 mL) was added compound C (377.0 mg, 1.55 mmol), $Na_2CO_3$ (246.0 mg, 2.33 mmol) and $Pd(PPh_3)_4$ (90.0 mg, 0.08 mmol). The reaction mixture was stirred at 110° C. and stirred overnight. The reaction mixture was completed detected by LCMS. Then the mixture was poured into 30 ml of water and the product was extracted with EA. The combined organic layer was concentrated in vacuum. The residue was purified by prep-HPLC to give compound I61 (20.0 mg) as a yellow solid. LCMS: 424.2 $[M+H]^+$. $^1H$ NMR (400 MHz, DMSO-$d_6$) δ: 11.31 (brs, 1H), 9.77 (s, 1H), 8.83 (s, 1H), 8.56 (s, 1H), 8.14 (s, 1H), 7.95 (d, J=8.8 Hz, 2H), 7.71 (dd, J=1.6, 8.4 Hz, 1H), 7.61 (d, J=8.4 Hz, 1H), 7.43 (t, J=2.4 Hz, 1H), 6.53 (d, J=8.8 Hz, 2H), 6.47 (s, 1H), 4.74 (s, 4H), 3.99 (s, 4H).

Example 15. N-(4-(2-oxa-6-azaspiro[3.4]octan-6-yl)phenyl)-6-(1H-indazol-6-yl)-[1,2,4]triazolo[1,5-a]pyrazin-8-amine (I63)

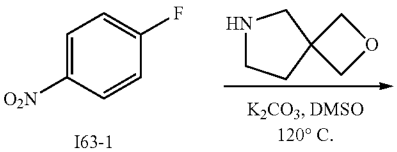

I63-1

-continued

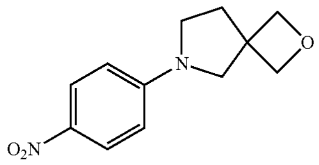

I63-2

To a solution of compound I63-1 (125 mg, 0.89 mmol) in DMSO (8 mL) was added 2-oxa-6-azaspiro[3.4]octane (130 mg, 1.16 mmol) and $K_2CO_3$ (245 g, 1.78 mmol). The resulting mixture was stirred at 120° C. for 4 h. The reaction was diluted with $H_2O$, filtered, washed with water, and concentrated to afford compound I63-2 (120 mg) as a yellow solid. LCMS: 235 $[M+H]^+$.

To a solution of compound I63-2 (120 g, 0.51 mmol) in MeOH (8 mL) was added palladium on carbon, the reaction was stirred at 50° C. under 1 bar hydrogen atmosphere for 4 h. The resulting mixture was filtered through Celite and the filtrate concentrated in vacuum to provide the crude compound I63-3 (95 mg). LCMS: 205 $[M+H]^+$.

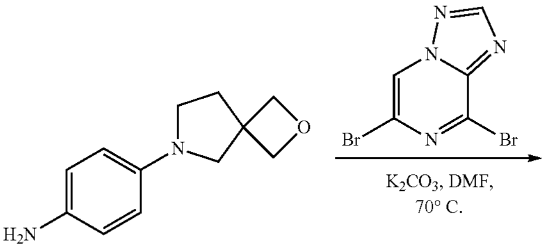

I63-3

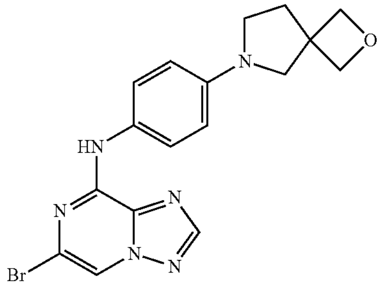

I63-4

Using the similar reaction conditions of synthesizing compound I53-2, compound I63-4 was obtained as a yellow solid (0.150 g). LCMS: 401 $[M+H]^+$.

Using the similar reaction conditions of synthesizing compound I22, and using compound I63-4 and compound B, compound I63 was obtained as a yellow solid (0.005 g). LCMS: 439 $[M+H]^+$. $^1H$ NMR (400 MHz, DMSO-$d_6$) δ: 13.23 (s, 1H), 9.81 (s, 1H), 8.97 (s, 1H), 8.60 (s, 1H), 8.27 (s, 1H), 8.10 (s, 1H), 7.92 (d, J=9.2 Hz, 2H), 7.84 (s, 2H), 6.65 (d, J=9.2 Hz, 2H), 4.63 (d, J=6.0 Hz, 2H), 4.57 (d, J=6.0 Hz, 2H), 3.55 (s, 2H), 3.30 (t, J=6.8 Hz, 2H), 2.29 (t, J=6.8 Hz, 2H).

Example 16. 6-(1H-indazol-5-yl)-N-(4-morpholinophenyl)-[1,2,4]triazolo[4,3-a]pyrazin-8-amine (I65)

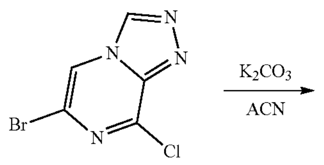

I65-1

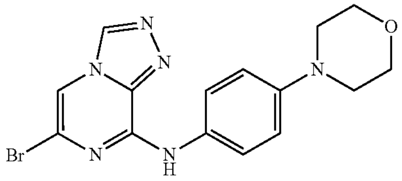

I65-2

With the similar reaction conditions of synthesizing compound 4, compound I65-2 was obtained as a yellow solid (0.57 g). LCMS: 376 $[M+H]^+$.

Using the similar reaction conditions of synthesizing compound I40, and using compound I65-2 and 5-(4,4,5,5-tetramethyl-1,3,2-dioxaborolan-2-yl)-1H-indazole, compound I65 was obtained as a yellow solid (0.010 g). LCMS 413 $[M+H]^+$. $^1$H NMR (400 MHz, DMSO-d$_6$) δ: 13. 23 (s, 1H), 10.17 (s, 1H), 9.28 (s, 1H), 8.61 (s, 1H), 8.18 (s, 1H), 8.10 (s, 1H), 8.04-8.01 (m, 2H), 7.85 (d, J=8.4 Hz, 1H), 7.70 (d, J=8.4 Hz, 1H), 7.03 (d, J=9.2 Hz, 2H), 3.79-3.76 (m, 4H), 3.14-3.12 (m, 4H).

Example 17. 6-(1H-indazol-5-yl)-N-(3-methoxy-4-morpholinophenyl)-[1,2,4]triazolo[4,3-a]pyrazin-8-amine (I67)

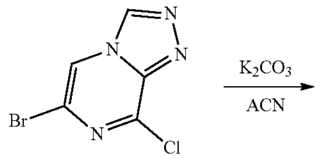

I65-1

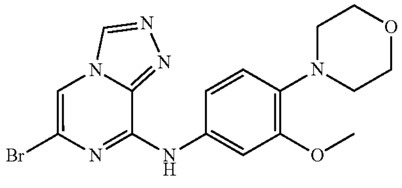

I67-2

Using the similar reaction conditions of synthesizing compound 4, compound I67-2 was obtained as a yellow solid (0.35 g). LCMS 406 $[M+H]^+$.

Using the similar reaction conditions of synthesizing compound I40, and using compound I67-2 and 5-(4,4,5,5-tetramethyl-1,3,2-dioxaborolan-2-yl)-1H-indazole, compound I67 was obtained as a yellow solid (0.015 g). LCMS 443 $[M+H]^+$. $^1$H NMR (400 MHz, DMSO-d$_6$) δ: 13. 24 (s, 1H), 10.21 (s, 1H), 9.30 (s, 1H), 8.63 (s, 1H), 8.21 (s, 1H), 8.11 (s, 1H), 8.05 (d, J=2.4 Hz, 1H), 7.86 (d, J=8.4 Hz, 1H), 7.75-7.68 (m, 1H), 7.67-7.65 (m, 2H), 6.95 (d, J=8.4 Hz, 1H), 3.85 (s, 3H), 3.75 (t, J=4.4 Hz, 4H), 2.98 (t, J=4.4 Hz, 4H).

Example 18. 6-(1H-indazol-5-yl)-N-(4-((1S,4R)-5-isopropyl-2,5-diazabicyclo[2.2.1]heptan-2-yl)phenyl)-[1,2,4]triazolo[1,5-a]pyrazin-8-amine (I69)

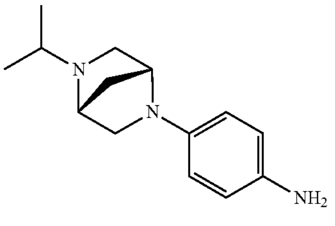

I69-1

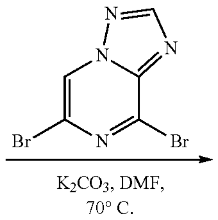

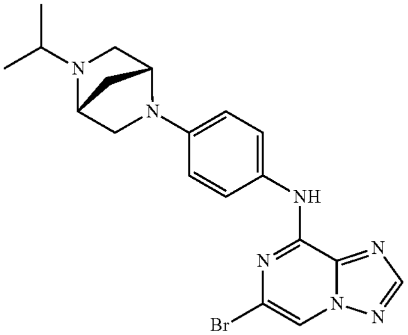

I69-2

Using the similar reaction conditions of synthesizing compound I53-2, compound I69-2 was obtained as a yellow solid (1 g). LCMS: 428 $[M+H]^+$.

Using the similar reaction conditions of synthesizing compound I22, and using compound I69-2 and 5-(4,4,5,5-tetramethyl-1,3,2-dioxaborolan-2-yl)-1H-indazole, compound I69 was obtained as a yellow solid (0.072 g). LCMS: 466 $[M+H]^+$. $^1$H NMR (400 MHz, DMSO-d$_6$) δ: 13. 21 (s, 1H), 9.88 (d, J=4.4 Hz, 1H), 8.92 (d, J=2.4 Hz, 1H), 8.60 (s, 1H), 8.48 (s, 1H), 8.18 (s, 1H), 8.11-8.08 (m, 1H), 8.13-7.97 (m, 2H), 7.64 (d, J=8.8 Hz, 1H), 6.81-6.78 (m, 2H), 4.66 (d, J=11.2 Hz, 2H), 3.70-3.61 (m, 2H), 3.56-3.45 (m, 2H), 3.41-3.36 (m, 1H), 2.33-2.24 (m, 1H), 2.17-2.07 (m, 1H), 1.36 (d, J=6.4 Hz, 2H), 1.30 (d, J=6.4 Hz, 1H), 1.25-1.21 (m, 3H).

Example 19. 6-(1H-indazol-6-yl)-N-(4-((1S,4R)-5-isopropyl-2,5-diazabicyclo[2.2.1]heptan-2-yl)phenyl)-[1,2,4]triazolo[1,5-a]pyrazin-8-amine (I71)

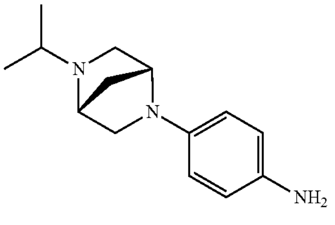

I71-1

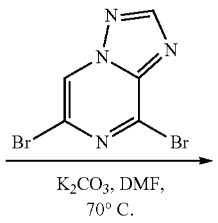

-continued

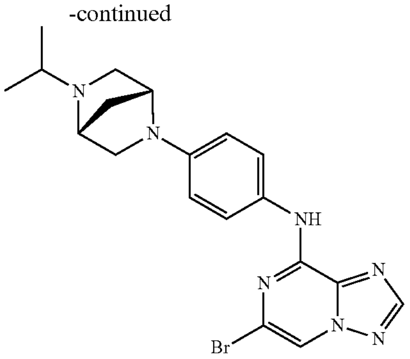

I71-2

Using the similar reaction conditions of synthesizing compound I53-2, compound I71-2 was obtained as a yellow solid (1 g). LCMS: 428 $[M+H]^+$.

Using the similar reaction conditions of synthesizing compound I22, and using compound I71-2 and compound B, compound I71 was obtained as a yellow solid (0.086 g). LCMS: 466 $[M+H]^+$. $^1H$ NMR (400 MHz, DMSO-$d_6$) δ: 13.21 (s, 1H), 9.90 (d, J=4.2 Hz, 1H), 9.00 (d, J=2.4 Hz, 1H), 8.62 (s, 1H), 8.25 (s, 1H), 8.11 (s, 1H), 8.00-7.97 (m, 1H), 7.85 (s, 2H), 7.64 (d, J=8.8 Hz, 1H), 6.78 (d, J=9.5 Hz, 2H), 4.65 (d, J=11.3 Hz, 2H), 3.70-3.40 (m, 6H), 2.26-2.25 (m, 2H), 2.12-2.04 (m, 1H), 1.34 (d, J=4.6 Hz, 2H), 1.30 (d, J=6.6 Hz, 1H), 1.24-1.21 (m, 3H).

Example 20. N-(3-ethoxy-4-morpholinophenyl)-6-(1H-indazol-6-yl)-[1,2,4]triazolo[1,5-a]pyrazin-8-amine (I73)

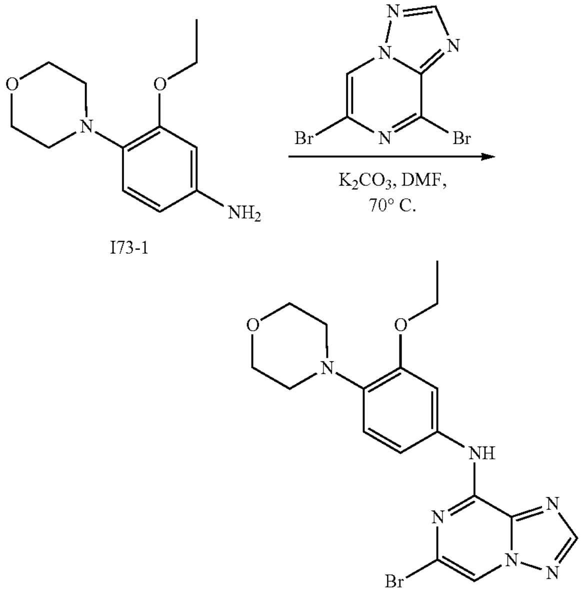

I73-1

I73-2

Using the similar reaction conditions of synthesizing compound I53-2, compound I73-2 was obtained as a yellow solid (0.3 g). LCMS: 405 $[M+H]^+$.

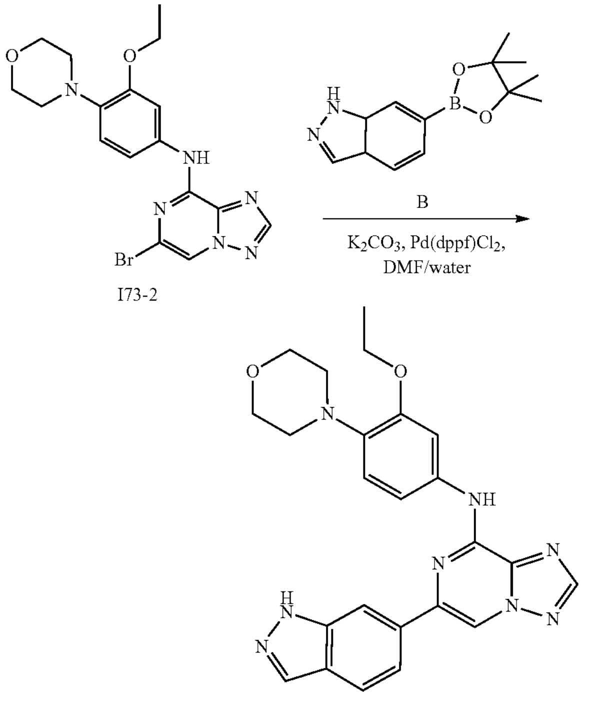

I73-2

I73

Using the similar reaction conditions of synthesizing compound I22, compound I73 was obtained as a yellow solid (0.091 g). LCMS: 457 $[M+H]^+$. $^1H$ NMR (400 MHz, DMSO-$d_6$) δ: 13. 24 (s, 1H), 10.03 (s, 1H), 9.06 (s, 1H), 8.65 (s, 1H), 8.28 (s, 1H), 8.12 (s, 1H), 8.01 (s, 1H), 7.89-7.84 (m, 2H), 7.69-7.66 (m, 1H), 6.96 (s, 1H), 4.14-4.09 (q, 2H), 3.79-3.77 (m, 4H), 3.08-3.04 (m, 4H), 1.40 (t, J=7.2 Hz, 3H).

Example 21. N-(3-cyclopropoxy-4-morpholinophenyl)-6-(1H-indazol-6-yl)-[1,2,4]triazolo[1,5-a]pyrazin-8-amine (I74)

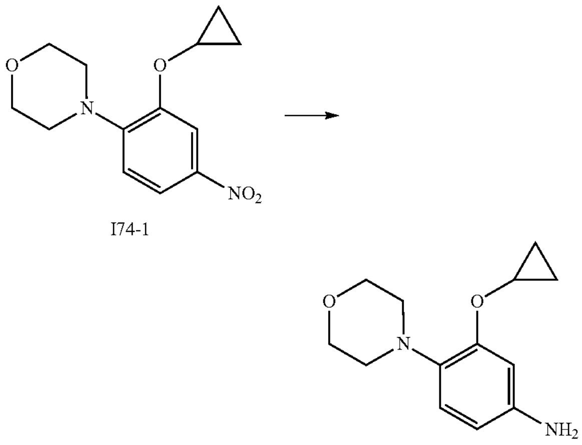

I74-1

I74-2

Using the similar reaction conditions of synthesizing compound 20, compound I74-2 was obtained as a yellow solid (0.155 g). LC-MS: 235 $[M+H]^+$.

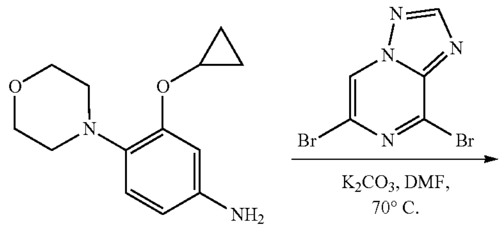

I74-2

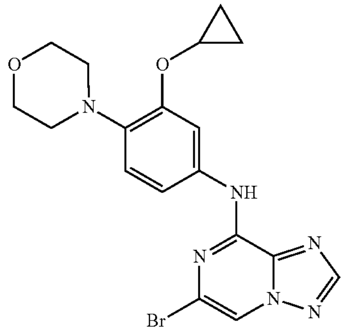

I74-3

Using the similar reaction conditions of synthesizing compound I53-2, compound I74-3 was obtained as a yellow solid (0.252 g). LCMS: 431 $[M+H]^+$.

Using the similar reaction conditions of synthesizing compound I1, and using compound I74-3 and (1H-indazol-6-yl) boronic acid, compound I74 was obtained as a yellow solid (0.032 g). LCMS: 469 $[M+H]^+$. $^1H$ NMR (400 MHz, DMSO-$d_6$) δ: 13.23 (s, 1H), 10.05 (s, 1H), 9.05 (s, 1H), 8.65 (s, 1H), 8.20 (s, 1H), 8.10 (s, 1H), 8.01 (s, 1H), 7.86-7.83 (m, 2H), 7.69-7.67 (m, 1H), 6.96 (s, 1H), 3.85 (s, 1H), 3.76 (m, 4H), 2.94 (m, 4H), 0.70-0.64 (m, 3H).

Example 22. 6-(1H-indazol-6-yl)-N-(3-isopropoxy-4-morpholinophenyl)-[1,2,4]triazolo[1,5-a]pyrazin-8-amine (I75)

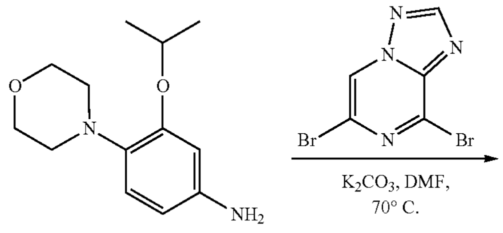

I75-1

-continued

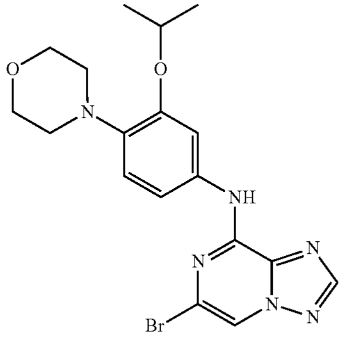

I75-2

Using the similar reaction conditions of synthesizing compound I53-2, compound I75-2 was obtained as a yellow solid (0.180 g). LCMS: 435 $[M+H]^+$.

Using the similar reaction conditions of synthesizing compound I22, and using compound I75-2 and compound B, compound I75 was obtained as a yellow solid (0.060 g). LCMS: 471 $[M+H]^+$. $^1H$ NMR (400 MHz, DMSO-$d_6$) δ: 9.98 (s, 1H), 9.08 (s, 1H), 8.60 (s, 1H), 8.25 (s, 1H), 8.10 (s, 1H), 7.90-7.84 (m, 4H), 6.98 (m, 1H), 4.58-4.50 (m, 1H), 3.89-3.78 (s, 4H), 2.99-3.07 (m, 4H), 1.41-1.30 (m, 7H). LCMS: 471 $[M+H]^+$.

Example 23. 6-(1H-indol-6-yl)-N-(3-methoxy-4-(5-(oxetan-3-yl)-2,5-diazabicyclo[2.2.1]heptan-2-yl)phenyl)-[1,2,4]triazolo[1,5-a]pyrazin-8-amine (I76)

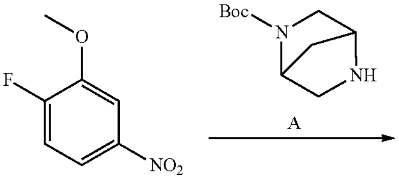

I76-1

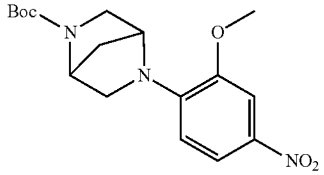

I76-2

To a solution of compound I76-1 (500 mg, 2.9 mmol) in DMSO (15 mL) was added compound A (695 mg, 3.5 mmol) and $K_2CO_3$ (0.84 g, 5.8 mmol). The resulting mixture was stirred at 100° C. for 1.5 h. The reaction was diluted with $H_2O$, filtered, washed with water, and concentrated to afford compound I76-2 (920 mg) as a yellow solid. LCMS: 350 $[M+H]^+$.

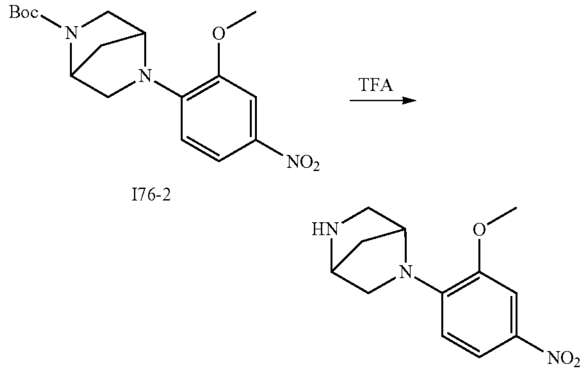

I176-2

I176-3

To a solution of compound I176-2 (500 mg, 1.43 mmol) in DCM (15 mL) was added TFA (10 mL). Then the reaction mixture was stirred at rt for 2 h. Then concentrated to afford compound I176-3 (326 mg) as a yellow solid. LCMS: 250 $[M+H]^+$.

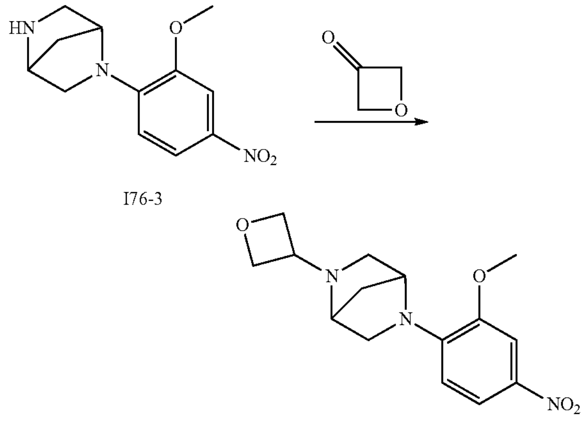

I176-3

I176-4

To a solution of compound I176-3 (300 mg, 1.2 mmol) in MeOH (15 mL) was added oxetan-3-one (175 mg, 2.4 mmol) and $Et_3N$ (10 drops). The reaction mixture was stirred at rt 2 h. $NaBH_3CN$ (151 mg, 2.4 mmol) was added and the resulting mixture was stirred at rt for 12 h. The reaction mixture was diluted with water and extracted with DCM. The combined organic layers were dried over anhydrous $Na_2SO_4$ and concentrated in vacuum. The residue was purified by flash chromatography on silica gel (DCM/MeOH=50/1) to afford compound I176-4 (317 mg) as a yellow solid. LCMS: 306 $[M+H]^+$.

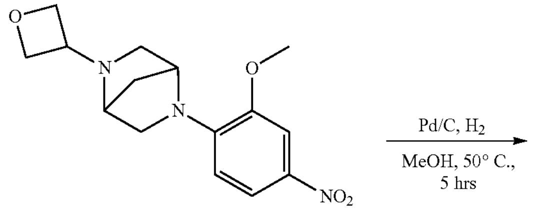

I176-4

-continued

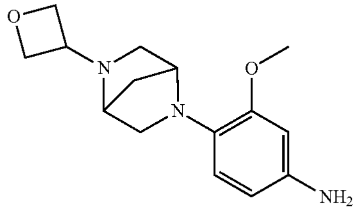

I176-5

Using the similar reaction conditions of synthesizing compound 20, compound I176-5 was obtained as a yellow solid (0.256 g). LCMS: 276 $[M+H]^+$.

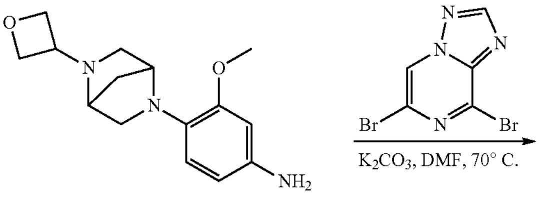

I176-5

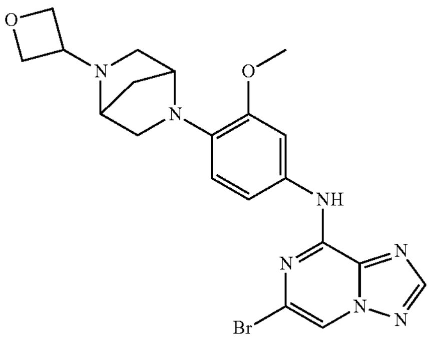

I176-6

Using the similar reaction conditions of synthesizing compound I53-2, compound I176-6 was obtained as a yellow solid (0.328 g). LCMS: 472 $[M+H]^+$.

Using the similar reaction conditions of synthesizing compound I22, and using compound I176-6 and compound C, compound I176 was obtained as a yellow solid (0.098 g). LCMS: 509 $[M+H]^+$. $^1H$ NMR (400 MHz, DMSO-$d_6$) δ: 11.29 (s, 1H), 9.90 (s, 1H), 8.87 (s, 1H), 8.11 (d, J=4.4 Hz, 2H), 7.76 (d, J=4.4 Hz, 2H), 8.10 (s, 1H), 7.89 (d, J=2.8 Hz, 1H), 7.77 (d, J=1.2 Hz, 1H), 7.62 (d, J=6.2 Hz, 1H), 7.63 (d, J=8.0 Hz, 2H), 7.43 (d, J=5.6 Hz, 1H), 6.8 (d, J=4.2 Hz, 1H), 6.50 (s, 1H), 4.71-4.50 (m, 6H), 4.28 (s, 1H), 3.88 (s, 3H), 3.76 (d, J=2.8 Hz, 2H), 3.48 (d, J=8.2 Hz, 1H), 2.20-2.08 (m, 2H).

Example 24. 6-(1H-indol-6-yl)-N-(4-(5-(oxetan-3-yl)-2,5-diazabicyclo[2.2.1]heptan-2-yl)-3-(trifluoromethoxy)phenyl)-[1,2,4]triazolo[1,5-a]pyrazin-8-amine (I77)

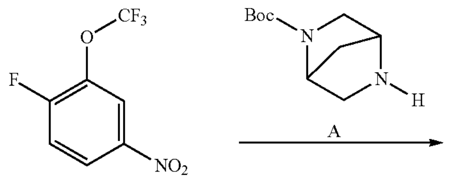

I77-1

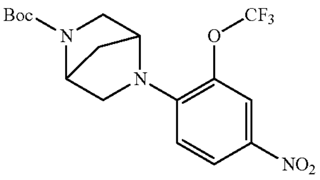

I77-2

Using the similar reaction conditions of synthesizing compound I76-2, compound I77-2 was obtained as a yellow solid (1.21 g). LCMS: 404 $[M+H]^+$.

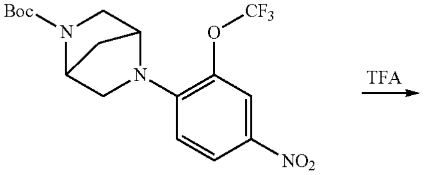

I77-2

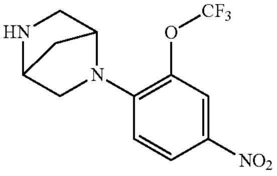

I77-3

Using the similar reaction conditions of synthesizing compound I76-3, compound I77-3 was obtained as a yellow oil (0.91 g). LCMS: 304 $[M+H]^+$.

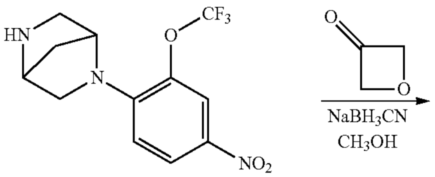

I77-3

-continued

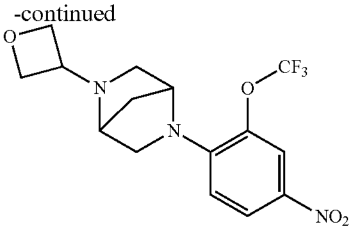

I77-4

Using the similar reaction conditions of synthesizing compound I76-4, compound I77-4 was obtained as a yellow solid (0.219 g). LCMS: 360 $[M+H]^+$.

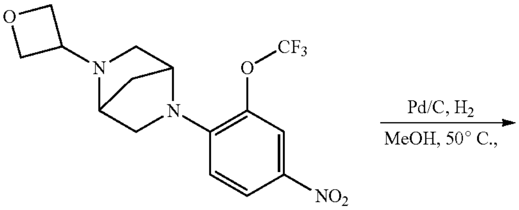

I77-4

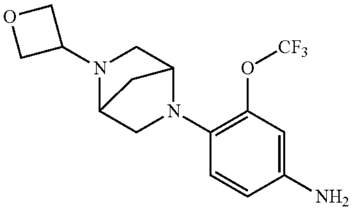

I77-5

Using the similar reaction conditions of synthesizing compound 20, compound I77-5 was obtained as a yellow solid (0.039 g). LCMS: 330 $[M+H]^+$.

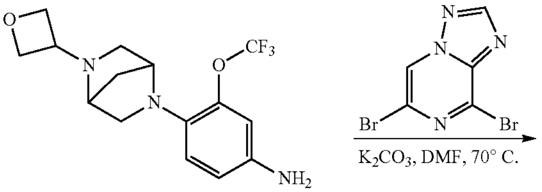

I77-5

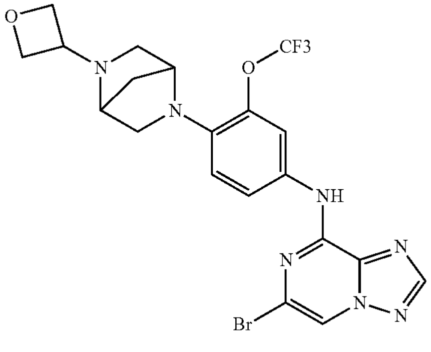

I77-6

Using the similar reaction conditions of synthesizing compound I53-2, compound I77-6 was obtained as a yellow solid (0.08 g). LCMS: 527 $[M+H]^+$.

Using the similar reaction conditions of synthesizing compound I22, and using compound I77-6 and compound C, compound I77 was obtained as a yellow solid (0.098 g). LCMS: 563 $[M+H]^+$. $^1$H NMR (400 MHz, DMSO-$d_6$) δ: 11.25 (s, 1H), 10.21 (s, 1H), 8.88 (s, 1H), 8.59 (s, 1H), 8.49 (s, 1H), 8.18-7.92 (m, 2H), 7.80-7.75 (m, 1H), 7.69-7.60 (m, 1H), 7.45-7.41 (m, 1H), 7.13-7.02 (m, H), 6.50 (m, 1H), 4.58-4.50 (m, 4H), 4.40-4.36 (m, 1H), 3.89-3.67 (m, 3H), 3.69-3.65 (m, 1H), 3.20-3.10 (s, 1H), 2.41-2.30 (m, 3H).

Example 25. N-(3-(difluoromethoxy)-4-(5-(oxetan-3-yl)-2,5-diazabicyclo[2.2.1]heptan-2-yl)phenyl)-6-(1H-indol-6-yl)-[1,2,4]triazolo[1,5-a]pyrazin-8-amine (I78)

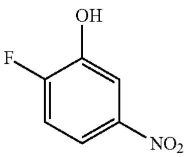

I78-1

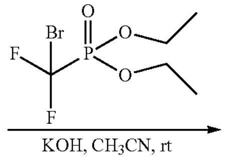

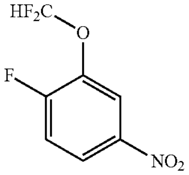

I78-2

To a solution of compound I78-1 (2 g, 13 mmol) in $CH_3CN$ (30 mL) was added compound KOH (3.6 g, 64 mmol). The resulting mixture was stirred at 0° C. for 0.5 h. Then diethyl (bromodifluoromethyl)phosphonate was added and stirred at rt for 1 h. The reaction mixture was diluted with water and extracted with EtOAc. The combined organic layers were dried over anhydrous $Na_2SO_4$ and concentrated in vacuum. The residue was purified by flash chromatography on silica gel (PE/EA=100/1) to afford compound I78-2 (1.8 g) as a yellow oil. LCMS: 208 $[M+H]^+$.

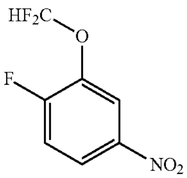

I78-2

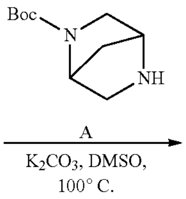

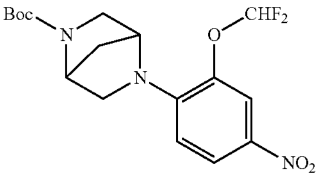

I78-3

Using the similar reaction conditions of synthesizing compound I76-2, compound I78-3 was obtained as a yellow solid (0.900 g). LCMS: 386 $[M+H]^+$.

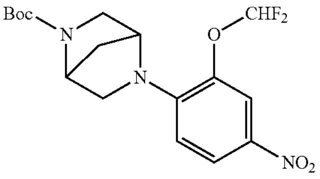

I78-3

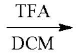

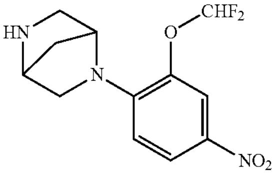

I78-4

Using the similar reaction conditions of synthesizing compound I76-3, compound I78-4 was obtained as a yellow solid (0.700 g). LCMS: 286 $[M+H]^+$.

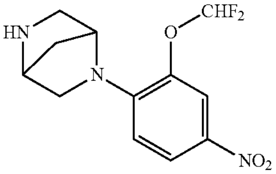

I78-4

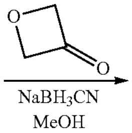

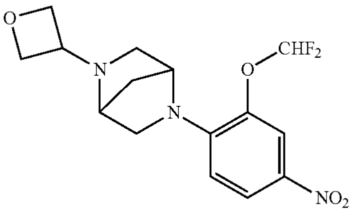

I78-5

Using the similar reaction conditions of synthesizing compound I76-4, compound I78-5 was obtained as a yellow oil (0.560 g). LCMS: 342 $[M+H]^+$.

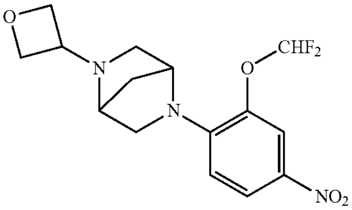

I78-5

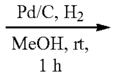

-continued

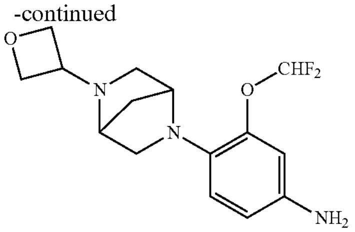

I78-6

Using the similar reaction conditions of synthesizing compound 20, compound I78-6 was obtained as crude compound (0.400 g). LCMS: 312 $[M+H]^+$.

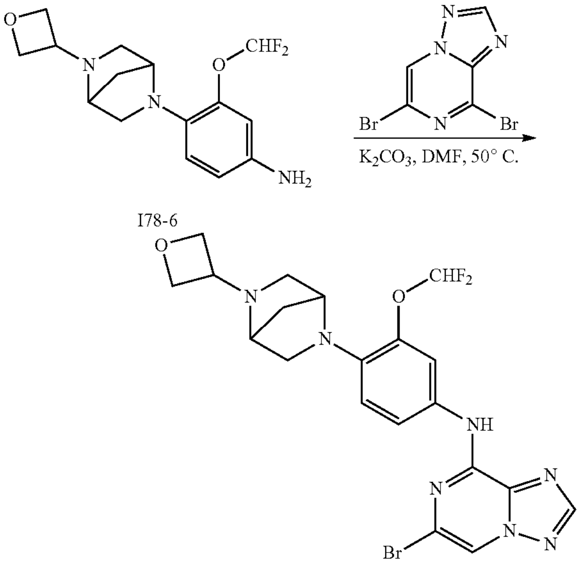

I78-6

I78-7

Using the similar reaction conditions of synthesizing compound I53-2, compound I78-7 was obtained as a yellow solid (0.5 g). LCMS: 508 $[M+H]^+$.

Using the similar reaction conditions of synthesizing compound I22, and using compound I78-7 and compound C, compound I78 was obtained as a yellow solid (0.098 g). LCMS: 545 $[M+H]^+$. $^1H$ NMR (400 MHz, DMSO-$d_6$) δ: 11.21 (s, 1H), 10.12 (s, 1H), 8.91 (s, 1H), 8.62 (s, 1H), 8.25 (s, 1H), 8.10 (s, 1H), 7.89 (d, J=2.8 Hz, 1H), 7.77 (d, J=1.2 Hz, 1H), 7.62 (d, J=8.0 Hz, 1H), 7.44 (t, J=3.2 Hz, 1H), 7.30-6.93 (m, 2H), 6.48 (s, 1H), 4.80-4.68 (m, 3H), 4.61-4.50 (m, 3H), 4.33 (s, 1H), 3.88-3.83 (m, 1H), 3.78-3.71 (m, 1H), 3.57 (d, J=10.4 Hz, 1H), 3.15-3.10 (m, 1H), 2.28-2.22 (m, 1H), 2.16-2.11 (m, 1H).

Example 26. N-(3-ethoxy-4-(5-(oxetan-3-yl)-2,5-diazabicyclo[2.2.1]heptan-2-yl)phenyl)-6-(1H-indol-6-yl)-[1,2,4]triazolo[1,5-a]pyrazin-8-amine (I79)

To a solution of compound I78-1 (1 g, 6.4 mmol) in DMF (20 mL) was added compound iodoethane (2 g, 13 mmol) and $K_2CO_3$ (1.8 g, 13 mmol). The resulting mixture was stirred at 50° C. for 1 h. The reaction was diluted with $H_2O$, filtered, washed with water, and concentrated to afford compound I79-2 (1.1 g,) as a yellow solid. LCMS: 186 $[M+H]^+$.

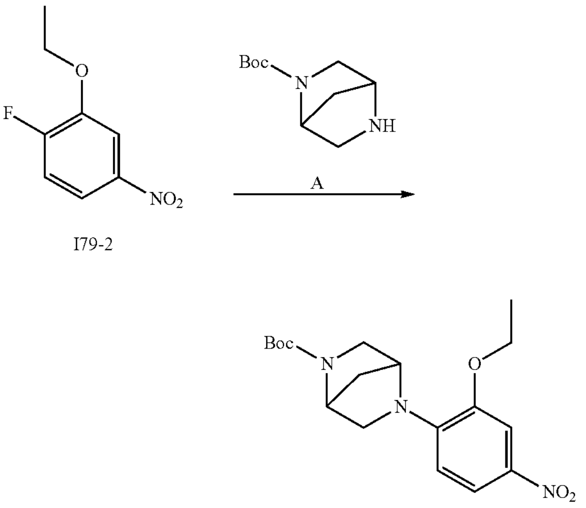

I79-2

I79-3

Using the similar reaction conditions of synthesizing compound I76-2, compound I79-3 was obtained as a yellow solid (0.560 g). LCMS: 364 $[M+H]^+$.

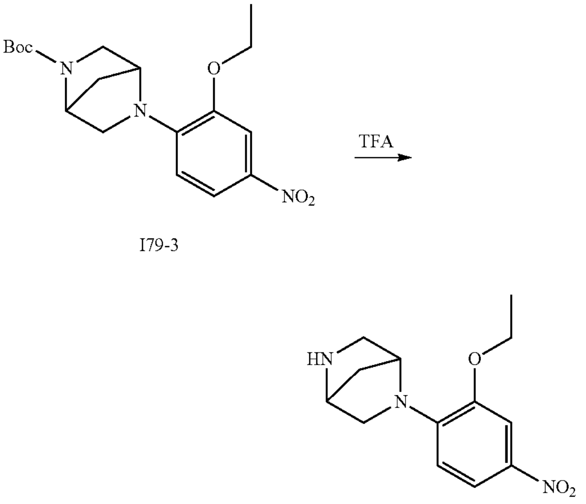

I79-3

I79-4

Using the similar reaction conditions of synthesizing compound I76-3, compound I79-4 was obtained as a yellow solid (0.400 g). LCMS: 264 $[M+H]^+$.

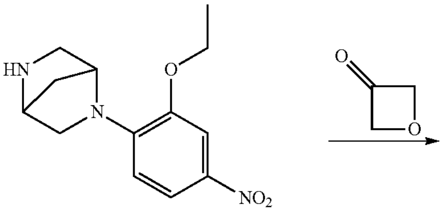

I79-4

-continued

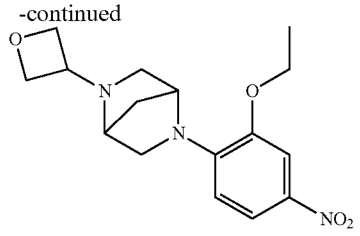

I79-5

Using the similar reaction conditions of synthesizing compound I76-4, compound I79-5 was obtained as a yellow oil (0.450 g). LCMS: 320 $[M+H]^+$.

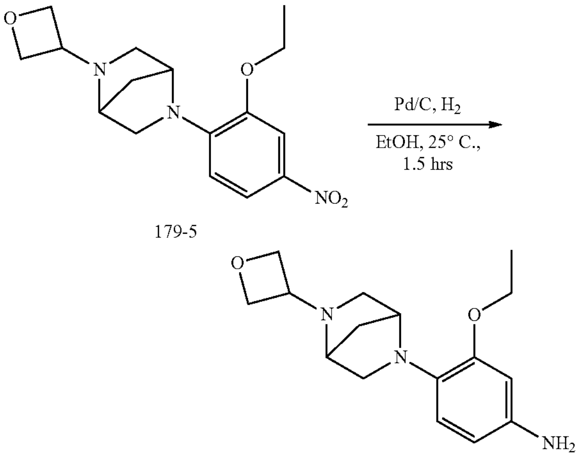

179-5

179-6

Using the similar reaction conditions of synthesizing compound 20, compound I79-6 was obtained as crude compound (0.350 g). LCMS: 290 $[M+H]^+$.

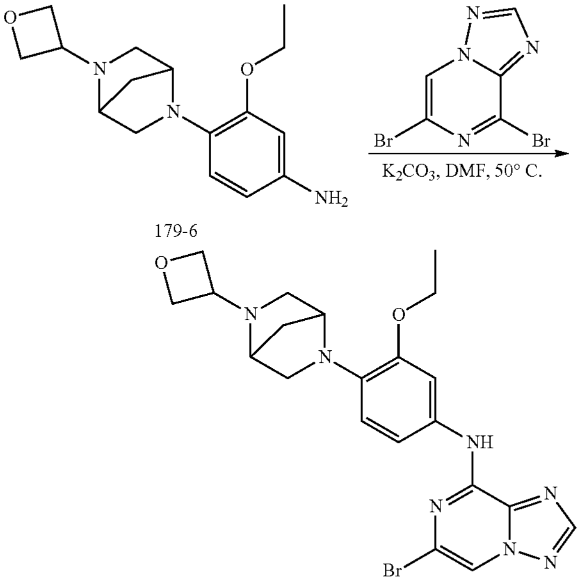

179-6

179-7

Using the similar reaction conditions of synthesizing compound I53-2, compound I79-7 was obtained as a yellow solid (0.39 g). LCMS: 488 $[M+H]^+$.

Using the similar reaction conditions of synthesizing compound I22, and using compound I79-7 and compound C, compound I79 was obtained as a yellow solid (0.098 g). LCMS: 523 $[M+H]^+$. $^1H$ NMR (400 MHz, DMSO-$d_6$) δ: 11.31 (s, 1H), 9.87 (s, 1H), 8.85 (s, 1H), 8.60 (s, 1H), 8.13 (s, 1H), 8.10 (s, 1H), 7.78 (d, J=8.4 Hz, 1H), 7.65-7.62 (m, 2H), 7.44 (t, J=2.4 Hz, 1H), 6.8 (d, J=8.4 Hz, 1H), 6.49 (s, 1H), 4.81-4.73 (m, 3H), 4.60-4.58 (m, 3H), 4.29 (s, 1H), 4.13-4.08 (m, 2H), 3.86-3.77 (m, 2H), 3.55 (d, J=11.6 Hz, 1H), 3.11 (d, J=10.8 Hz, 1H), 2.24-2.11 (m, 2H), 1.40 (t, J=7.2 Hz, 3H).

Example 27. N-(3-cyclopropoxy-4-(5-(oxetan-3-yl)-2,5-diazabicyclo[2.2.1]heptan-2-yl)phenyl)-6-(1H-indol-6-yl)-[1,2,4]triazolo[1,5-a]pyrazin-8-amine (I80)

To a solution of compound I78-1 (1 g, 6.4 mmol) in DMF (15 mL) was added BnBr (1.31 g, 7.7 mmol) and $K_2CO_3$ (1.77 g, 12.8 mmol). The resulting mixture was stirred at rt for 1.5 h. The reaction was diluted with $H_2O$, filtered, washed with water, and concentrated to afford compound I80-2 (1.26 mg,) as a yellow solid. LCMS: 248 $[M+H]^+$.

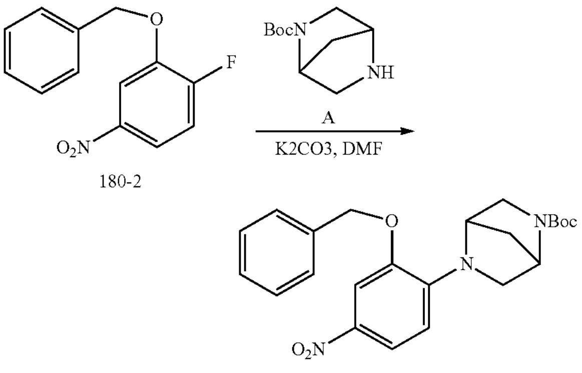

180-2

180-3

Using the similar reaction conditions of synthesizing compound I76-2, compound I80-3 was obtained as a yellow solid (0.740 g). LCMS: 426 $[M+H]^+$.

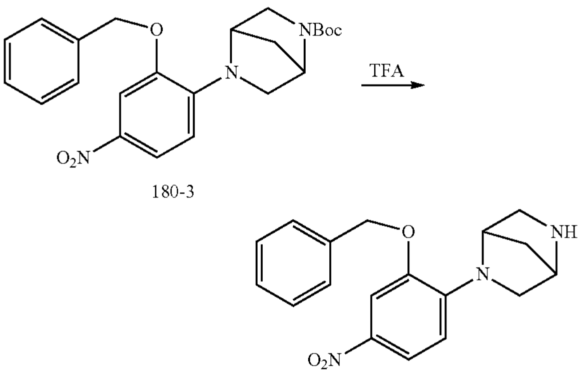

180-3

180-4

Using the similar reaction conditions of synthesizing compound I76-3, compound I80-4 was obtained as a yellow solid (0.322 g). LCMS: 326 $[M+H]^+$.

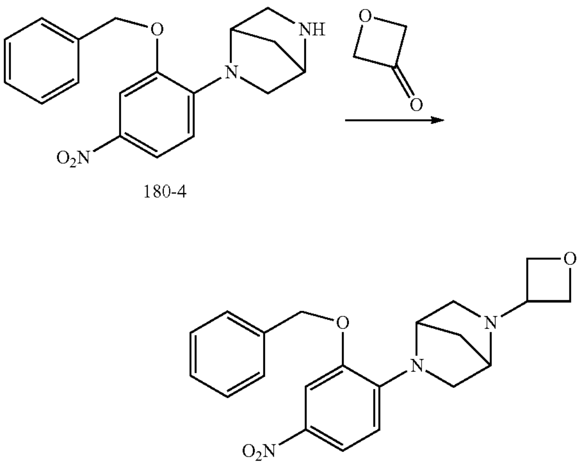

180-4

180-5

Using the similar reaction conditions of synthesizing compound I76-4, compound I80-5 was obtained as a yellow solid (0.315 g). LCMS: 382 $[M+H]^+$.

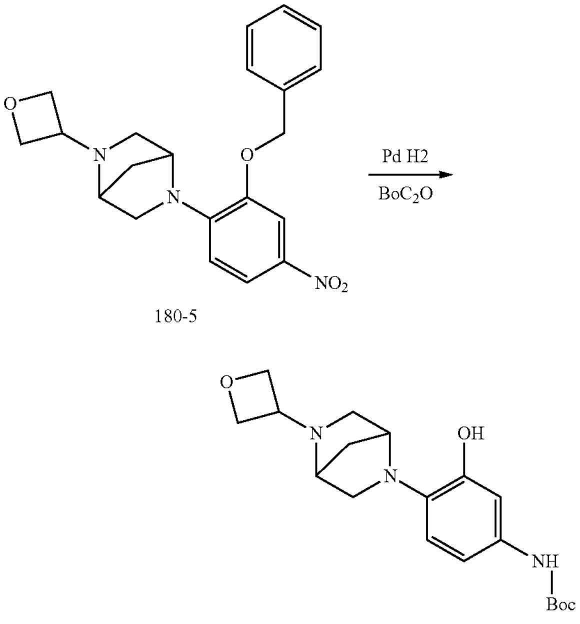

180-5

180-6

To a solution of compound I80-5 (300 mg, 0.79 mmol) in MeOH (10 mL) was added $BoC_2O$ (189 mg, 0.87 mmol) and palladium on carbon, the reaction was stirred at 65° C. under 1 bar hydrogen atmosphere for 4 h. The resulting mixture was filtered through Celite and the filtrate concentrated in vacuum to provide the crude compound I80-6 (226 mg) as a yellow solid. LCMS: 362 $[M+H]^+$.

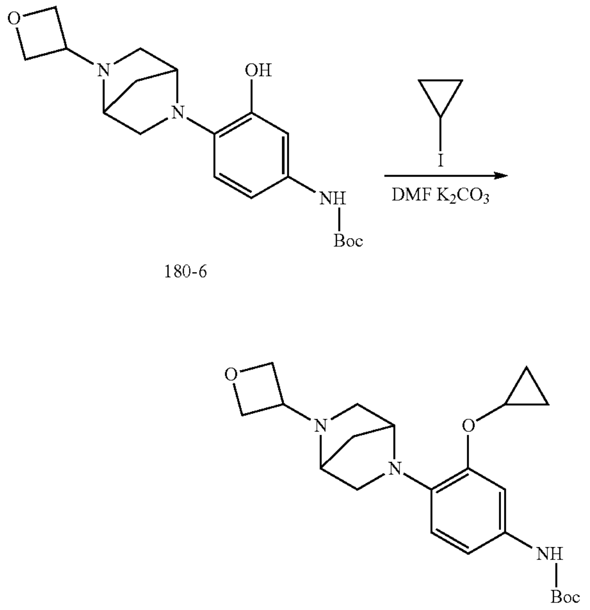

180-6

180-7

To a solution of compound I80-6 (200 mg, 0.55 mmol) in DMF (15 mL) was added iodocyclopropane (98.2 mg, 0.66 mmol) and $K_2CO_3$ (228 g, 1.65 mmol). The resulting mixture was stirred at 100° C. for 1.5 h. The reaction was diluted with $H_2O$, filtered, washed with water, and concentrated to afford compound I80-7 (198 mg) as a yellow solid. LCMS: 402 $[M+H]^+$.

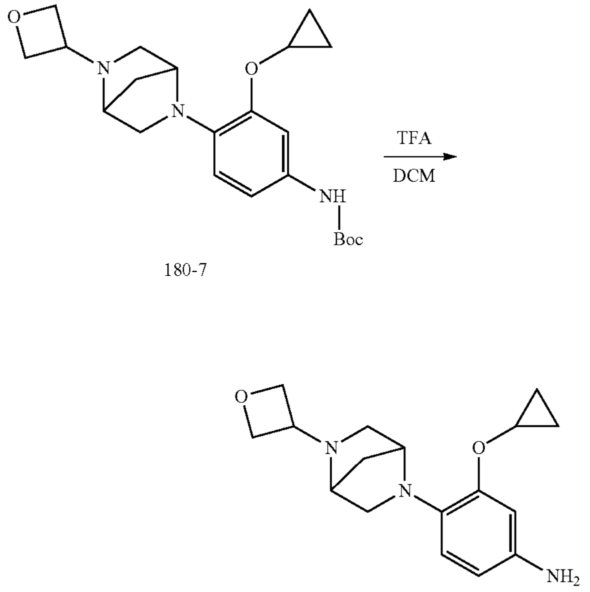

180-7

180-8

To a solution of compound I80-7 (190 mg, 0.47 mmol) in DCM (5 mL) was added TFA (2 mL). Then the reaction mixture was stirred at rt for 2 h. Then concentrated to afford compound I80-8 (106 mg) as a yellow solid. LCMS: 302 $[M+H]^+$.

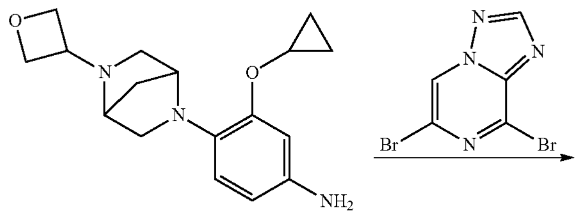

180-8

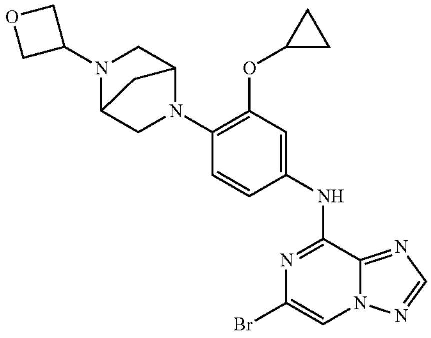

180-9

Using the similar reaction conditions of synthesizing compound I53-2, compound I80-9 was obtained as a yellow solid (0.125 g). LCMS: 498 $[M+H]^+$.

Using the similar reaction conditions of synthesizing compound I22, and using compound I80-9 and compound C, compound I80 was obtained as a yellow solid (0.019 g). LCMS: 535 $[M+H]^+$. $^1H$ NMR (400 MHz, DMSO-$d_6$) δ: 11.25 (s, 1H), 9.80 (s, 1H), 8.81 (s, 1H), 8.62 (s, 1H), 8.17 (d, J=4.2 Hz, 2H), 7.74 (d, J=2.8 Hz, 1H), 7.60 (d, J=3.6 Hz, 1H), 7.41 (d, J=6.4 Hz, 1H), 6.64 (d, J=6.0 Hz, 1H), 6.46 (s, 1H), 4.55-4.51 (m, 2H), 4.33-4.24 (m, 1H), 3.83 (d, J=4.2 Hz, 3H), 3.33-3.13 (m, 4H), 2.88-2.67 (m, 1H), 2.17 (d, J=2.2 Hz, 2H), 0.68-0.63 (m, 4H).

Example 28. 6-(1H-indol-6-yl)-N-(3-isopropoxy-4-(5-(oxetan-3-yl)-2,5-diazabicyclo[2.2.1]heptan-2-yl)phenyl)-[1,2,4]triazolo[1,5-a]pyrazin-8-amine (I81)

To a solution of compound I78-1 (1 g, 6.37 mmol) in DMF (20 mL) was added $K_2CO_3$ (1.76 g, 12.73 mmol) and iodopropane (2.16 g, 12.73 mmol). The mixture was stirred at 50° C. for 1 h. The reaction mixture was diluted with $H_2O$ and filtered to give compound I81-2 (1.13 g) as a yellow solid. LCMS: 196 $[M+H]^+$.

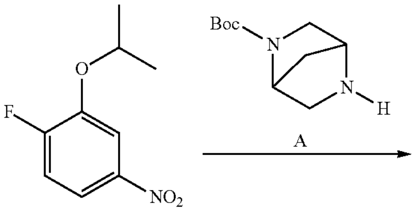

181-2

-continued

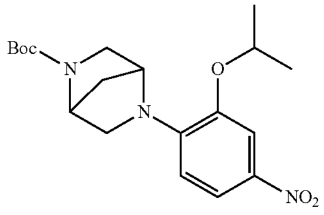

181-3

Using the similar reaction conditions of synthesizing compound I76-2, compound I81-3 was obtained as a yellow solid (0.33 g). LCMS: 378 $[M+H]^+$.

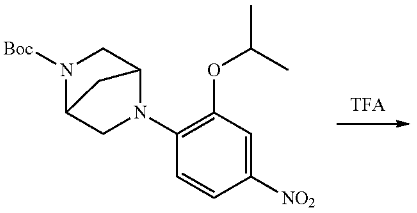

181-3

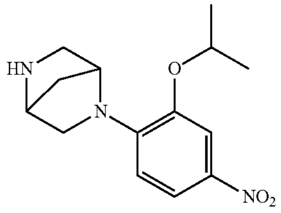

181-4

Using the similar reaction conditions of synthesizing compound I76-3, compound I81-4 was obtained as a yellow oil (0.2475 g). LCMS: 278 $[M+H]^+$.

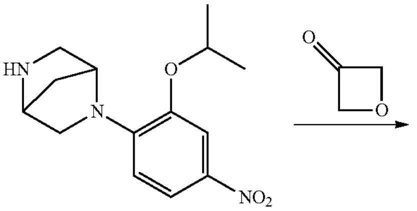

181-4

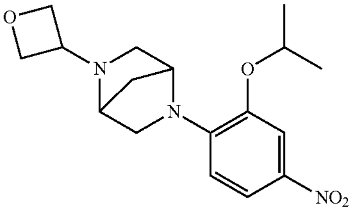

181-5

Using the similar reaction conditions of synthesizing compound I76-4, compound I81-5 was obtained as a yellow solid (0.219 g). LCMS: 334 $[M+H]^+$.

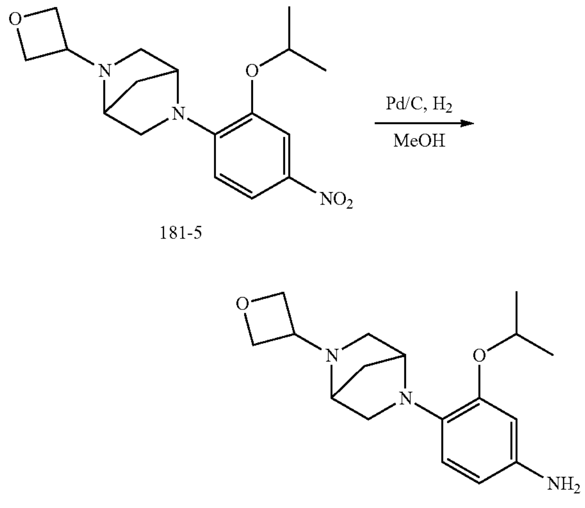

181-5

181-6

Using the similar reaction conditions of synthesizing compound 20, compound I81-6 was obtained as a yellow solid (0.114 g). LCMS: 304 $[M+H]^+$.

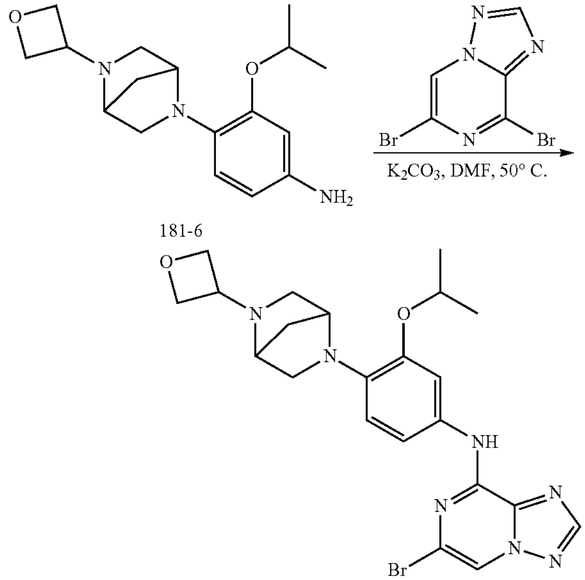

181-6

181-7

Using the similar reaction conditions of synthesizing compound I53-2, compound I81-7 was obtained as a yellow solid (0.125 g). LCMS: 501 $[M+H]^+$.

Using the similar reaction conditions of synthesizing compound I22, and using compound I81-7 and compound C, compound I81 was obtained as a yellow solid (0.120 g). LCMS: 537 $[M+H]^+$. $^1H$ NMR (400 MHz, DMSO-$d_6$) δ: 11.26 (s, 1H), 10.56 (s, 1H), 9.89 (s, 1H), 8.89 (s, 1H), 8.58 (s, 1H), 8.09 (s, 1H), 7.91 (s, 1H), 7.75-7.69 (m, 2H), 7.65-7.59 (m, 1H), 7.49-7.45 (m, 1H), 6.79-6.76 (m, 1H), 6.49 (s, 1H), 4.79-4.50 (m, 7H), 4.26 (m, 1H), 3.88-3.76 (m, 2H), 3.50 (d, 1H), 3.11 (d, 1H), 2.20-2.13 (m, 2H), 1.41-1.30 (m, 6H).

Example 29. 6-(1H-indol-6-yl)-N-(4-(5-(oxetan-3-yl)-2,5-diazabicyclo[2.2.1]heptan-2-yl)phenyl)-[1,2,4]triazolo[1,5-a]pyrazin-8-amine (I82)

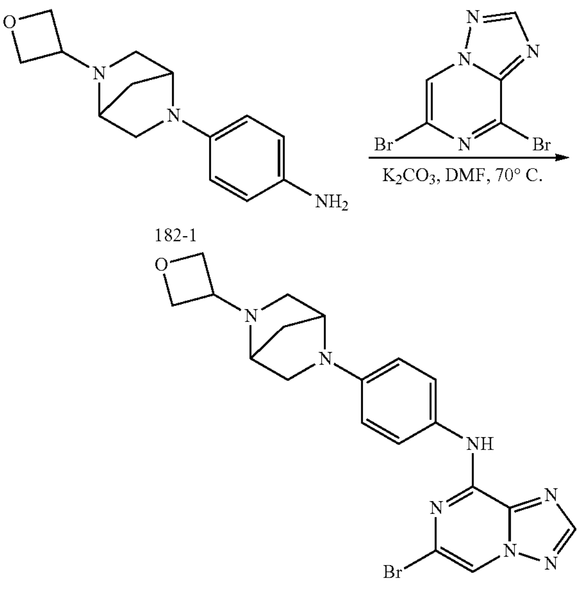

182-1

182-2

Using the similar reaction conditions of synthesizing compound I53-2, compound I82-2 was obtained as a yellow solid (0.249 g). LCMS: 442 $[M+H]^+$.

Using the similar reaction conditions of synthesizing compound I22, and using compound I82-2 and compound C, compound I82 was obtained as a yellow solid (0.106 g). LCMS: 479 $[M+H]^+$. $^1H$ NMR (400 MHz, DMSO-$d_6$) δ: 11.30 (s, 1H), 9.86 (s, 1H), 8.95 (s, 1H), 8.85 (s, 1H), 8.12 (s, 1H), 8.03 (d, J=2.8 Hz, 2H), 7.74 (d, J=3.2 Hz, 1H), 7.62 (d, J=2.2 Hz, 1H), 7.43 (d, J=3.6 Hz, 1H), 6.78 (d, J=4.6 Hz, 2H), 6.48 (s, 2H), 4.81-4.51 (m, 6H), 4.39 (s, 3H), 3.77-3.49 (m, 3H), 3.10 (d, J=2.6 Hz, 1H), 2.33-2.19 (m, 2H).

In Vitro Spleen Tyrosine Kinase (SYK) Inhibition Assay

The biological properties of the new compounds are investigated based on the following in vitro assay methods.

SYK Kinase Assay

A homogeneous time-resolved fluorescence (HTRF) assay was performed to assess the potential inhibitory effect of compounds on SYK kinase. The HTRF KinEASE-TK kit (Cisbio) was used. During the step, kinase will phosphorylate the substrate, and the resulting fluorescence signal is proportional to the phosphorylation level. The assay was performed in the following steps: First, the testing compounds were diluted 1:3 in succession in DMSO. The 1× kinase buffer contained 1 volume of 5× enzymatic buffer with 4 volumes of distilled water, 5 mM $MgCl_2$, 1 mM $MnCl_2$, and 1 mM DTT. The assays were assembled in 384 well plates (784075, Greiner) where 10 nl of compound solutions were added into each well, and the plates were centrifuged at 1000 g for 1 min. Then, 5 μl of 2×SYK in 1× kinase buffer were added to each well. The plates were centrifuged at 1000 g for 30 s and then incubated at room temperature for 10 min. The reaction was initiated by adding 5ul of premixed 2×TK-substrate-biotin and ATP mixture in 1× kinase buffer to the assay plates. The plates were centrifuged at 1000 g for 30 s and incubated at room temperature for 30 min. Phosphorylation was detected by adding 5 μl of 4×Sa-XL 665 in HTRF detection buffer into each well of the assay plates. The plates were centrifuged plates at 1000 g for 30 sec, and then incubated at room temperature for 1 h. Finally, the plates were read on an Envision 2104 plate reader (PerkinElmer) and the fluorescence signal was measured at 615 nm (Cryptate) and 665 nm (XL665).

A ratio (665/615 nm) was calculated for each well. The inhibition ratio was calculated as follow:

$$\%\ \text{Inhibition} = \left[1 - \frac{\text{Ratio}_{cmpd} - \overline{\text{Ratio}}_{positive}}{\overline{\text{Ratio}}_{vehicle} - \overline{\text{Ratio}}_{positive}}\right] * 100$$

$\overline{\text{Ratio}}_{positive}$: The average Ratio for the positive controls across the plate $\overline{Ratio}_{vehicle}$: The average Ratio for negative controls across the plate $IC_{50}$ was calculated by fitting % Inhibition values and log of compound concentrations to nonlinear regression (dose response-variable slope) with GraphPad 6.0. The results were summarized in Table 1.

Ba/F3-TEL-SYK Cell-Based Assay

The compounds were tested to assess their ability to selectively inhibit SYK-dependent Ba/F3 cell proliferation. CellTiter-Glo® Luminescent Cell Viability Assay was used to determine the number of viable cells in culture based on quantitation of the ATP present, as an indicator of metabolically active cells. The assay was performed in the following steps: First, the testing compounds were dissolved in DMSO to make a stock solution. The stocks (10 mM) were then diluted to varying concentrations: 2000, 666.67, 222.22, 74.07, 24.69, 8.23, 2.743, 0.941, 0.305 and 0.102 μM. An aliquot of 0.2 μl of diluted compounds were added to the 384 well assay plate. Second, added 40 μl of cell suspension with 800 Ba/F3-TEL-SYK cells into each well and incubated the plate at 37° C., 5% $CO_2$ for 72 hr. Then, added 20 μl Cell Titer-Glo Reagent into each well of the cell culture plate. Mixed the contents for 2 min on an orbital shaker to lyse cells, and rest the plate at room temperature for 30 min. Finally, luminescence values were obtained using an Envision 2104 plate reader (PerkinElmer) and calculated the average data and Standard Deviation (SD) of DMSO and Reference (GS-9973, 1 μM) as high control and low control. To determine the $IC_{50}$ value, fit the data using non-linear regression equation. The results were presented in Table 1.

TABLE 1

IC50 for SyK kinase assay and Ba/F3-TEL-SYK cell-based assay

| Cpd No. | Syk inhibition $IC_{50}$ (nM) | BaF3 Cell assay $IC_{50}$ (nM) | Cpd No. | Syk inhibition $IC_{50}$ (nM) | BaF3 Cell assay $IC_{50}$ (nM) |
|---|---|---|---|---|---|
| I48 | >10000 | NA | I12 | A | A |
| I9 | NA | NA | I13 | A | NA |
| I10 | A | B | I14 | A | NA |
| I3 | A | A | I15 | A | NA |
| I1 | A | A | I16 | A | A |
| I5 | B | NA | I17 | A | B |
| I6 | B | NA | I18 | A | A |
| I4 | B | NA | I8 | A | NA |
| I29 | A | B | I19 | A | NA |
| I2 | A | A | I53 | A | A |
| I7 | A | D | I54 | A | A |
| I26 | B | B | I55 | A | C |
| I28 | A | B | I56 | B | C |
| I27 | B | NA | I57 | A | A |
| I20 | B | NA | I58 | A | A |
| I21 | A | B | I59 | B | B |
| I22 | A | A | I60 | B | B |
| I23 | A | B | I61 | A | B |
| I24 | A | A | I62 | A | B |
| I25 | A | B | I63 | D | NA |
| I30 | B | NA | I64 | D | NA |
| I31 | B | NA | I65 | D | NA |
| I32 | B | NA | I66 | D | NA |
| I33 | B | NA | I67 | C | NA |
| I34 | D | NA | I68 | D | NA |
| I35 | D | NA | I69 | B | C |
| I36 | B | NA | I70 | B | C |
| I37 | B | NA | I71 | B | NA |
| I38 | D | NA | I72 | A | C |
| I39 | D | NA | I73 | A | B |
| I40 | D | NA | I74 | B | NA |
| I41 | D | NA | I75 | B | C |
| I42 | D | NA | I76 | A | B |
| I43 | D | NA | I77 | B | D |
| I44 | D | NA | I78 | A | C |
| I46 | C | NA | I79 | A | B |
| I45 | D | NA | I80 | C | NA |
| I47 | C | NA | I81 | B | C |
| I11 | A | NA | I82 | A | C |

NA: not analyzed.
A: $IC_{50} \leq 50$ nM;
B: $50 < IC_{50} \leq 500$;
C: $500 < IC_{50} \leq 5000$;
D: $IC_{50} > 5000$ On the basis of their biological properties the compounds of formula (I) according to the invention, some of the compounds exhibit good inhibitory effect upon SYK and are suitable for treating cancer, allergic disorders, autoimmune diseases and inflammatory diseases.

In Vivo Pharmacokinetic Analysis

This is a single-dose study in ICR mice (male, n=9/administration) with intravenous and oral administration. Compound concentrations in plasma were measured and calculated for pharmacokinetic (PK) analysis via WinNonLin 6.4.

| | | IV Administration (2 mg/kg) PO Administration (10 mg/kg) | | | | | |
|---|---|---|---|---|---|---|---|
| Cpd No. | | $C_{max}$ (ng/mL) | $T_{max}$ (hr) | $AUC_{last}$ (ng*h/mL) | $AUC_{inf}$ (ng*h/mL) | $t_{1/2}$ (hr) | F % |
| I1 | IV | 2520.4 | 0.08 | 980.2 | 983.2 | 0.25 | |
| | PO | 88.8 | 0.50 | 380.7 | 447.6 | 0.90 | 7.77 |
| I2 | IV | 1874.8 | 0.08 | 1005.9 | 1011.4 | 0.57 | |
| | PO | 696.0 | 0.25 | 1955.7 | 2264.6 | 2.80 | 38.88 |
| I22 | IV | 1315.3 | 0.08 | 428.1 | 428.7 | 0.21 | |
| | PO | 108.1 | 0.25 | 115.2 | 125.1 | 0.48 | 5.38 |
| I10 | IV | 8813 | 0.08 | 11209 | 11378 | 1.65 | |
| | PO | 2163 | 4.00 | 28485 | 28493 | 1.67 | 50.8 |
| I53 | IV | 3962.1 | 0.08 | 2285.1 | 2304.3 | 9.83 | |
| | PO | 7524.9 | 0.25 | 7333.6 | 7374.1 | 4.41 | 64.19 |
| I54 | IV | 1638.3 | 0.08 | 498.6 | 499.6 | 0.65 | |
| | PO | 267.5 | 0.25 | 144.9 | 151.2 | 0.78 | 5.81 |
| I57 | IV | 7355.4 | 0.08 | 4667 | 4670.7 | 0.72 | |
| | PO | 14400.3 | 0.25 | 14464.8 | 14498.3 | 3.27 | 61.99 |
| I58 | IV | 5113.7 | 0.08 | 1681.3 | 1683.5 | 0.71 | |
| | PO | 2568.5 | 0.25 | 895 | 902.1 | 1.49 | 10.65 |

Some compounds possess both pharmaceutically acceptable properties and desired PK properties, such as high bioavailability (F %).

What is claimed:

1. A compound of Formula (I):

Formula (I)

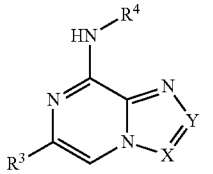

or a pharmaceutically acceptable salt, stereoisomer, or tautomer thereof, wherein:

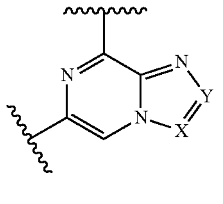

is

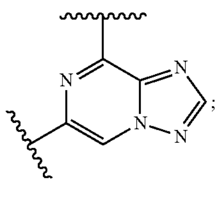

;

$R^3$ is benzodioxolyl, 2H-1,4-benzoxazin-3(4H)-onyl, 2H-pyrido[3,2-b][1,4]oxazin-3(4H)-onyl, pyrazolyl, thiazolyl, pyridinyl, pyrazinyl, indolyl, isoindolyl, indazolyl, or benzothiazolyl, wherein the benzodioxolyl, 2H-1,4-benzoxazin-3(4H)-onyl, 2H-pyrido[3,2-b][1,4]oxazin-3(4H)-onyl, pyrazolyl, thiazolyl, pyridinyl, pyrazinyl, indolyl, isoindolyl, indazolyl, or benzothiazolyl is optionally substituted with one, two, or three substituents independently selected from the group consisting of halo, $C_{1-6}$ alkyl, $C_{2-6}$ alkenyl, $C_{2-6}$ alkynyl, $C(O)NHR^5$, C(O)OH, $NH_2$, $OC_{1-6}$ alkyl, and $C_{3-8}$ cycloalkyl;

$R^4$ is benzodioxolyl, phenyl, or pyridinyl;

wherein the benzodioxolyl, phenyl, or pyridinyl is optionally substituted with one, two, or three substituents independently selected from the group consisting of halo, $C_{1-6}$ alkyl, $OC_{1-6}$ alkyl, piperazinyl, 4-hydroxy-4-methylpiperazin-1-yl, $C_{3-8}$ cycloalkoxy, morpholin-4-yl, 1,1-dioxothiomorpholin-4-yl, 2,5-diazabicyclo[2.2.1]heptan-2-yl, 2-oxa-6-azaspiro[3.3]heptan-6-yl, and 2-oxa-6-azaspiro[3.4]octan-6-yl;

wherein each $C_{1-6}$ alkyl and $OC_{1-6}$ alkyl substituent is optionally and independently substituted with one, two, or three independently selected halo substituents;

wherein each piperazinyl substituent is optionally and independently substituted with one or two substituents independently selected from the group consisting of $C_{1-6}$ alkyl, $CF_3$, $CH_2CF_3$, $CH(OH)CH_3$, $CH_2CH_2OH$, $CH(OCH_3)CH_3$, $CH_2CH_2OCH_3$, $S(O)_2CH_3$, $S(O)_2CH_2CH_3$, $C_{3-8}$ cycloalkyl, and $C_{2-6}$ cycloalkoxy; and wherein each 2,5-diazabicyclo[2.2.1]heptan-2-yl substituent is optionally and independently substituted with one or two substituents independently selected from the group consisting of $C_{1-6}$ alkyl and $C_{2-6}$ cycloalkoxy; and each $R^5$ is independently H, $C_{1-6}$ alkyl, $C_{2-6}$ alkenyl, $C_{2-6}$ alkynyl, or OC(O)phenyl.

2. The compound of claim 1, or a pharmaceutically acceptable salt, stereoisomer, or tautomer thereof, wherein $R^3$ is 2H-1,4-benzoxazin-3(4H)-onyl, 2H-pyrido[3,2-b][1,4]oxazin-3(4H)-onyl, pyrazolyl, thiazolyl, pyridinyl, pyrazinyl, indolyl, isoindolyl, or indazolyl, wherein the 2H-1,4-benzoxazin-3(4H)-onyl, 2H-pyrido[3,2-b][1,4]oxazin-3(4H)-onyl, pyrazolyl, thiazolyl, pyridinyl, pyrazinyl, indolyl, isoindolyl, or indazolyl is optionally substituted with one, two, or three substituents independently selected from the group consisting of halo, $C_{1-6}$ alkyl, $C_{2-6}$ alkenyl, $C_{2-6}$ alkynyl, $C(O)NHR^5$, C(O)OH, $NH_2$, $OC_{1-6}$ alkyl, and $C_{3-8}$ cycloalkyl.

3. The compound of claim 2, or a pharmaceutically acceptable salt, stereoisomer, or tautomer thereof, wherein $R^4$ is phenyl or pyridinyl;

wherein the phenyl or pyridinyl is optionally substituted with one, two, or three substituents independently selected from the group consisting of halo, $C_{1-6}$ alkyl, $OC_{1-6}$ alkyl, piperazinyl, 4-hydroxy-4-methylpiperazin-1-yl, $C_{3-8}$ cycloalkoxy, morpholin-4-yl, 1,1-dioxothiomorpholin-4-yl, 2,5-diazabicyclo[2.2.1]heptan-2-yl, 2-oxa-6-azaspiro[3.3]heptan-6-yl, and 2-oxa-6-azaspiro[3.4]octan-6-yl;

wherein each $C_{1-6}$ alkyl and $OC_{1-6}$ alkyl substituent is optionally and independently substituted with one, two, or three independently selected halo substituents;

wherein each piperazinyl substituent is optionally and independently substituted with one or two substituents independently selected from the group consisting of $C_{1-6}$ alkyl, $CF_3$, $CH_2CF_3$, $CH(OH)CH_3$, $CH_2CH_2OH$, $CH(OCH_3)CH_3$, $CH_2CH_2OCH_3$, $S(O)_2CH_3$, $S(O)_2CH_2CH_3$, $C_{3-8}$ cycloalkyl, and oxetanyl; and wherein each 2,5-diazabicyclo[2.2.1]heptan-2-yl substituent is optionally and independently substituted with one or two substituents independently selected from the group consisting of $C_{1-6}$ alkyl and oxetanyl.

4. The compound of claim 2, or a pharmaceutically acceptable salt, stereoisomer, or tautomer thereof, wherein $R^4$ is benzodioxolyl;

wherein the benzodioxolyl is optionally substituted with one, two, or three substituents independently selected from the group consisting of halo, $C_{1-6}$ alkyl, and $OC_{1-6}$ alkyl; and wherein each $C_{1-6}$ alkyl and $OC_{1-6}$ alkyl substituent is optionally and independently substituted with one, two, or three independently selected halo substituents.

5. The compound of claim 1, or a pharmaceutically acceptable salt, stereoisomer, or tautomer thereof, wherein $R^3$ is 2H-1,4-benzoxazin-3(4H)-onyl, 2H-pyrido[3,2-b][1,4]oxazin-3(4H)-onyl, indolyl, or indazolyl, wherein the 2H-1,4-benzoxazin-3(4H)-onyl, 2H-pyrido[3,2-b][1,4]oxazin-3(4H)-onyl, indolyl, or indazolyl is optionally substituted with one, two, or three substituents independently selected from the group consisting of halo, $C_{1-6}$ alkyl, and $OC_{1-6}$ alkyl.

6. The compound of claim 5, or a pharmaceutically acceptable salt, stereoisomer, or tautomer thereof, wherein $R^4$ is phenyl or pyridinyl;

wherein the phenyl or pyridinyl is optionally substituted with one, two, or three substituents independently selected from the group consisting of halo, $C_{1-6}$ alkyl, $OC_{1-6}$ alkyl, piperazinyl, 4-hydroxy-4-methylpiperazin-1-yl, $C_{3-8}$ cycloalkoxy, morpholin-4-yl, 1,1-dioxothiomorpholin-4-yl, 2,5-diazabicyclo[2.2.1]heptan-2-yl, 2-oxa-6-azaspiro[3.3]heptan-6-yl, and 2-oxa-6-azaspiro[3.4]octan-6-yl;

wherein each $C_{1-6}$ alkyl and $OC_{1-6}$ alkyl substituent is optionally and independently substituted with one, two, or three independently selected halo substituents;

wherein each piperazinyl substituent is optionally and independently substituted with one or two substituents independently selected from the group consisting of $C_{1-6}$ alkyl, $CF_3$, $CH_2CF_3$, $CH(OH)CH_3$, $CH_2CH_2OH$, $CH(OCH_3)CH_3$, $CH_2CH_2OCH_3$, $S(O)_2CH_3$, $S(O)_2CH_2CH_3$, $C_{3-8}$ cycloalkyl, and oxetanyl; and wherein each 2,5-diazabicyclo[2.2.1]heptan-2-yl substituent is optionally and independently substituted with one or two substituents independently selected from the group consisting of $C_{1-6}$ alkyl and oxetanyl.

7. The compound of claim 5, or a pharmaceutically acceptable salt, stereoisomer, or tautomer thereof, wherein $R^4$ is benzodioxolyl;

wherein the benzodioxolyl is optionally substituted with one, two, or three substituents independently selected from the group consisting of halo, $C_{1-6}$ alkyl, and $OC_{1-6}$ alkyl; and wherein each $C_{1-6}$ alkyl and $OC_{1-6}$ alkyl substituent is optionally and independently substituted with one, two, or three independently selected halo substituents.

8. The compound of claim 1, or a pharmaceutically acceptable salt, stereoisomer, or tautomer thereof, wherein $R^3$ is pyrazinyl, wherein the pyrazinyl is optionally substituted with one, two, or three substituents independently selected from the group consisting of halo, $C_{1-6}$ alkyl, $C(O)NHR^5$, $C(O)OH$, $NH_2$, and $OC_{1-6}$ alkyl.

9. The compound of claim 8, or a pharmaceutically acceptable salt, stereoisomer, or tautomer thereof, wherein $R^4$ is phenyl or pyridinyl;

wherein the phenyl or pyridinyl is optionally substituted with one, two, or three substituents independently selected from the group consisting of halo, $C_{1-6}$ alkyl, $OC_{1-6}$ alkyl, piperazinyl, 4-hydroxy-4-methylpiperazin-1-yl, $C_{3-8}$ cycloalkoxy, morpholin-4-yl, 1,1-dioxothiomorpholin-4-yl, 2,5-diazabicyclo[2.2.1]heptan-2-yl, 2-oxa-6-azaspiro[3.3]heptan-6-yl, and 2-oxa-6-azaspiro[3.4]octan-6-yl;

wherein each $C_{1-6}$ alkyl and $OC_{1-6}$ alkyl substituent is optionally and independently substituted with one, two, or three independently selected halo substituents;

wherein each piperazinyl substituent is optionally and independently substituted with one or two substituents independently selected from the group consisting of $C_{1-6}$ alkyl, $CF_3$, $CH_2CF_3$, $CH(OH)CH_3$, $CH_2CH_2OH$, $CH(OCH_3)CH_3$, $CH_2CH_2OCH_3$, $S(O)_2CH_3$, $S(O)_2CH_2CH_3$, $C_{3-8}$ cycloalkyl, and oxetanyl; and wherein each 2,5-diazabicyclo[2.2.1]heptan-2-yl substituent is optionally and independently substituted with one or two substituents independently selected from the group consisting of $C_{1-6}$ alkyl and oxetanyl.

10. The compound of claim 8, or a pharmaceutically acceptable salt, stereoisomer, or tautomer thereof, wherein $R^4$ is benzodioxolyl;

wherein the benzodioxolyl is optionally substituted with one, two, or three substituents independently selected from the group consisting of halo, $C_{1-6}$ alkyl, and $OC_{1-6}$ alkyl; and wherein each $C_{1-6}$ alkyl and $OC_{1-6}$ alkyl substituent is optionally and independently substituted with one, two, or three independently selected halo substituents.

11. The compound of claim 1, or a stereoisomer thereof, wherein the compound, or stereoisomer thereof, is selected from the group consisting of:

6-(1H-indazol-6-yl)-N-(4-morpholinophenyl)-[1,2,4]triazolo[1,5-a]pyrazin-8-amine;

6-(1H-indol-6-yl)-N-(4-morpholinophenyl)-[1,2,4]triazolo[1,5-a]pyrazin-8-amine;

6-(1H-indazol-6-yl)-N-(3-methoxy-4-morpholinophenyl)-[1,2,4]triazolo[1,5-a]pyrazin-8-amine;

N-(3,4-dimethoxyphenyl)-6-(1H-indazol-6-yl)-[1,2,4]triazolo[1,5-a]pyrazin-8-amine;

6-(1H-indazol-6-yl)-N-(3,4,5-trimethoxyphenyl)-[1,2,4]triazolo[1,5-a]pyrazin-8-amine;

7-(8-((4-morpholinophenyl)amino)-[1,2,4]triazolo[1,5-a]pyrazin-6-yl)-2H-benzo[b][1,4]oxazin-3(4H)-one;

6-(1H-indol-6-yl)-N-(3-methoxy-4-morpholinophenyl)-[1,2,4]triazolo[1,5-a]pyrazin-8-amine;

7-(8-((3-methoxy-4-morpholinophenyl)amino)-[1,2,4]triazolo[1,5-a]pyrazin-6-yl)-2,2-dimethyl-2H-benzo[b][1,4]oxazin-3(4H)-one;

7-(8-((3-methoxy-4-morpholinophenyl)amino)-[1,2,4]triazolo[1,5-a]pyrazin-6-yl)-2H-benzo[b][1,4]oxazin-3(4H)-one;

2,2-dimethyl-7-(8-((4-morpholinophenyl)amino)-[1,2,4]triazolo[1,5-a]pyrazin-6-yl)-2H-benzo[b][1,4]oxazin-3(4H)-one;

7-(8-((3-methoxy-4-morpholinophenyl)amino)-[1,2,4]triazolo[1,5-a]pyrazin-6-yl)-2H-pyrido[3,2-b][1,4]oxazin-3(4H)-one;

7-(8-((4-morpholinophenyl)amino) ~ [1,2,4]triazolo[1,5-a]pyrazin-6-yl)-2H-pyrido[3,2-b][1,4]oxazin-3(4H)-one;

7-(8-((3-methoxy-4-morpholinophenyl)amino)-[1,2,4]triazolo[1,5-a]pyrazin-6-yl)-2,2-dimethyl-2H-pyrido[3,2-b][1,4]oxazin-3(4H)-one;

2,2-dimethyl-7-(8-((4-morpholinophenyl)amino)-[1,2,4]triazolo[1,5-a]pyrazin-6-yl)-2H-pyrido[3,2-b][1,4]oxazin-3(4H)-one;

7-(8-((3,4,5-trimethoxyphenyl)amino)-[1,2,4]triazolo[1,5-a]pyrazin-6-yl)-2H-pyrido[3,2-b][1,4]oxazin-3(4H)-one;

2,2-dimethyl-7-(8-((3,4,5-trimethoxyphenyl)amino)-[1,2,4]triazolo[1,5-a]pyrazin-6-yl)-2H-pyrido[3,2-b][1,4]oxazin-3(4H)-one;

7-(8-((3,4-dimethoxyphenyl)amino)-[1,2,4]triazolo[1,5-a]pyrazin-6-yl)-2H-pyrido[3,2-b][1,4]oxazin-3(4H)-one;

7-(8-((3,4-dimethoxyphenyl)amino)-[1,2,4]triazolo[1,5-a]pyrazin-6-yl)-2,2-dimethyl-2H-pyrido[3,2-b][1,4]oxazin-3(4H)-one;

7-(8-((2,2-difluorobenzo[d][1,3]dioxol-5-yl)amino)-[1,2,4]triazolo[1,5-a]pyrazin-6-yl)-2H-pyrido[3,2-b][1,4]oxazin-3(4H)-one;

7-(8-((4-morpholinophenyl)amino)-[1,2,4]triazolo[1,5-a]pyrazin-6-yl)-2H-pyrido[3,2-b][1,4]oxazin-3(4H)-one;

7-(8-((3-methoxy-4-morpholinophenyl)amino)-[1,2,4]triazolo[1,5-a]pyrazin-6-yl)-2,2-dimethyl-2H-pyrido[3,2-b][1,4]oxazin-3(4H)-one;

2,2-dimethyl-7-(8-((4-morpholinophenyl)amino)-[1,2,4]triazolo[1,5-a]pyrazin-6-yl)-2H-pyrido[3,2-b][1,4]oxazin-3(4H)-one;

7-(8-((3,4,5-trimethoxyphenyl)amino)-[1,2,4]triazolo[1,5-a]pyrazin-6-yl)-2H-pyrido[3,2-b][1,4]oxazin-3(4H)-one;

2,2-dimethyl-7-(8-((3,4,5-trimethoxyphenyl)amino)-[1,2,4]triazolo[1,5-a]pyrazin-6-yl)-2H-pyrido[3,2-b][1,4]oxazin-3(4H)-one;

7-(8-((3,4-dimethoxyphenyl)amino)-[1,2,4]triazolo[1,5-a]pyrazin-6-yl)-2H-pyrido[3,2-b][1,4]oxazin-3(4H)-one;

7-(8-((3,4-dimethoxyphenyl)amino)-[1,2,4]triazolo[1,5-a]pyrazin-6-yl)-2,2-dimethyl-2H-pyrido[3,2-b][1,4]oxazin-3(4H)-one;

7-(8-((2,2-difluorobenzo[d][1,3]dioxol-5-yl)amino)-[1,2,4]triazolo[1,5-a]pyrazin-6-yl)-2H-pyrido[3,2-b][1,4]oxazin-3(4H)-one;

7-(8-((2,2-difluorobenzo[d][1,3]dioxol-5-yl)amino)-[1,2,4]triazolo[1,5-a]pyrazin-6-yl)-2,2-dimethyl-2H-pyrido[3,2-b][1,4]oxazin-3(4H)-one;

6-(1H-indazol-6-yl)-N-(4-morpholino-3-(trifluoromethoxy)phenyl)-[1,2,4]triazolo[1,5-a]pyrazin-8-amine;

N-(3-(difluoromethoxy)-4-morpholinophenyl)-6-(1H-indazol-6-yl)-[1,2,4]triazolo[1,5-a]pyrazin-8-amine;

1-(4-((6-(1H-indazol-6-yl)-[1,2,4]triazolo[1,5-a]pyrazin-8-yl)amino)-2-methoxyphenyl)-4-methylpiperidin-4-ol;

1-(4-((6-(1H-indazol-6-yl)-[1,2,4]triazolo[1,5-a]pyrazin-8-yl)amino)phenyl)-4-methylpiperidin-4-ol;

4-(4-((6-(1H-indazol-6-yl)-[1,2,4]triazolo[1,5-a]pyrazin-8-yl)amino)-2-methoxyphenyl)thiomorpholine 1,1-dioxide;

4-(4-((6-(1H-indazol-6-yl)-[1,2,4]triazolo[1,5-a]pyrazin-8-yl)amino)phenyl)thiomorpholine 1,1-dioxide;

6-(1H-indazol-6-yl)-N-(4-(4-methylpiperazin-1-yl)phenyl)-[1,2,4]triazolo[1,5-a]pyrazin-8-amine;

6-(1H-indazol-6-yl)-N-(3-methoxy-4-(4-methylpiperazin-1-yl)phenyl)-[1,2,4]triazolo[1,5-a]pyrazin-8-amine;

N-(4-(4-(ethylsulfonyl)piperazin-1-yl)-3-methoxyphenyl)-6-(1H-indazol-6-yl)-[1,2,4]triazolo[1,5-a]pyrazin-8-amine;

N-(4-(4-(ethylsulfonyl)piperazin-1-yl)phenyl)-6-(1H-indazol-6-yl)-[1,2,4]triazolo[1,5-a]pyrazin-8-amine;

2-(4-(4-((6-(1H-indazol-6-yl)-[1,2,4]triazolo[1,5-a]pyrazin-8-yl)amino)-2-methoxyphenyl)piperazin-1-yl)ethan-1-ol;

N-(4-(4-ethylpiperazin-1-yl)-3-methoxyphenyl)-6-(1H-indazol-6-yl)-[1,2,4]triazolo[1,5-a]pyrazin-8-amine;

6-(1H-indazol-6-yl)-N-(4-(4-isopropylpiperazin-1-yl)-3-methoxyphenyl)-[1,2,4]triazolo[1,5-a]pyrazin-8-amine;

6-(1H-indazol-6-yl)-N-(3-methoxy-4-(4-(2-methoxyethyl)piperazin-1-yl)phenyl)-[1,2,4]triazolo[1,5-a]pyrazin-8-amine;

6-(1H-indazol-6-yl)-N-(3-methoxy-4-(4-(2,2,2-trifluoroethyl)piperazin-1-yl)phenyl)-[1,2,4]triazolo[1,5-a]pyrazin-8-amine;

N-(4-(4-cyclopropylpiperazin-1-yl)-3-methoxyphenyl)-6-(1H-indazol-6-yl)-[1,2,4]triazolo[1,5-a]pyrazin-8-amine;

6-(1H-indazol-6-yl)-N-(4-(4-(oxetan-3-yl)piperazin-1-yl)phenyl)-[1,2,4]triazolo[1,5-a]pyrazin-8-amine;

6-(1H-indazol-6-yl)-N-(3-methoxy-4-(4-(oxetan-3-yl)piperazin-1-yl)phenyl)-[1,2,4]triazolo[1,5-a]pyrazin-8-amine;

6-(6-aminopyrazin-2-yl)-N-(4-(4-(oxetan-3-yl)piperazin-1-yl)phenyl)-[1,2,4]triazolo[1,5-a]pyrazin-8-amine;

6-(6-aminopyrazin-2-yl)-N-(3-methoxy-4-(4-(oxetan-3-yl)piperazin-1-yl)phenyl)-[1,2,4]triazolo[1,5-a]pyrazin-8-amine;

6-(1H-indazol-6-yl)-N-(4-(4-(oxetan-3-yl)piperazin-1-yl)phenyl)-[1,2,4]triazolo[1,5-a]pyrazin-8-amine;

6-(1H-indazol-6-yl)-N-(3-methoxy-4-(4-(oxetan-3-yl)piperazin-1-yl)phenyl)-[1,2,4]triazolo[1,5-a]pyrazin-8-amine;

6-(6-aminopyrazin-2-yl)-N-(4-(4-(oxetan-3-yl)piperazin-1-yl)phenyl)-[1,2,4]triazolo[1,5-a]pyrazin-8-amine;

6-(6-aminopyrazin-2-yl)-N-(3-methoxy-4-(4-(oxetan-3-yl)piperazin-1-yl)phenyl)-[1,2,4]triazolo[1,5-a]pyrazin-8-amine;

6-(1H-indol-6-yl)-N-(4-(4-(oxetan-3-yl)piperazin-1-yl)phenyl)-[1,2,4]triazolo[1,5-a]pyrazin-8-amine;

6-(1H-indol-6-yl)-N-(3-methoxy-4-(4-(oxetan-3-yl)piperazin-1-yl)phenyl)-[1,2,4]triazolo[1,5-a]pyrazin-8-amine;

N-(4-(2-oxa-6-azaspiro[3.3]heptan-6-yl)phenyl)-6-(1H-indazol-6-yl)-[1,2,4]triazolo[1,5-a]pyrazin-8-amine;

6-(1H-indazol-6-yl)-N-(3-methoxy-4-(2-oxa-6-azaspiro[3.3]heptan-6-yl)phenyl)-[1,2,4]triazolo[1,5-a]pyrazin-8-amine;

N-(4-(2-oxa-6-azaspiro[3.3]heptan-6-yl)phenyl)-6-(1H-indol-6-yl)-[1,2,4]triazolo[1,5-a]pyrazin-8-amine;

6-(3H-indol-6-yl)-N-(3-methoxy-4-(2-oxa-6-azaspiro[3.3]heptan-6-yl)phenyl)-[1,2,4]triazolo[1,5-a]pyrazin-8-amine;

N-(4-(2-oxa-6-azaspiro[3.4]octan-6-yl)phenyl)-6-(1H-indazol-6-yl)-[1,2,4]triazolo[1,5-a]pyrazin-8-amine;

N-(4-(2-oxa-6-azaspiro[3.4]octan-6-yl)phenyl)-6-(1H-indol-6-yl)-[1,2,4]triazolo[1,5-a]pyrazin-8-amine;

6-(1H-indazol-5-yl)-N-(4-((1S,4R)-5-isopropyl-2,5-diazabicyclo[2.2.1]heptan-2-yl)phenyl)-[1,2,4]triazolo[1,5-a]pyrazin-8-amine;

6-(1H-indol-5-yl)-N-(4-((1S,4R)-5-isopropyl-2,5-diazabicyclo[2.2.1]heptan-2-yl)phenyl)-[1,2,4]triazolo[1,5-a]pyrazin-8-amine;

6-(1H-indazol-6-yl)-N-(4-((1S,4R)-5-isopropyl-2,5-diazabicyclo[2.2.1]heptan-2-yl)phenyl)-[1,2,4]triazolo[1,5-a]pyrazin-8-amine;

6-(1H-indol-6-yl)-N-(4-((1S,4R)-5-isopropyl-2,5-diazabicyclo[2.2.1]heptan-2-yl)phenyl)-[1,2,4]triazolo[1,5-a]pyrazin-8-amine;

N-(3-ethoxy-4-morpholinophenyl)-6-(1H-indazol-6-yl)-[1,2,4]triazolo[1,5-a]pyrazin-8-amine;

N-(3-cyclopropoxy-4-morpholinophenyl)-6-(1H-indazol-6-yl)-[1,2,4]triazolo[1,5-a]pyrazin-8-amine;

6-(1H-indazol-6-yl)-N-(3-isopropoxy-4-morpholinophenyl)-[1,2,4]triazolo[1,5-a]pyrazin-8-amine;

6-(1H-indol-6-yl)-N-(3-methoxy-4-(5-(oxetan-3-yl)-2,5-diazabicyclo[2.2.1]heptan-2-yl)phenyl)-[1,2,4]triazolo[1,5-a]pyrazin-8-amine;

6-(1H-indol-6-yl)-N-(4-(5-(oxetan-3-yl)-2,5-diazabicyclo[2.2.1]heptan-2-yl)-3-(trifluoromethoxy)phenyl)-[1,2,4]triazolo[1,5-a]pyrazin-8-amine;

N-(3-(difluoromethoxy)-4-(5-(oxetan-3-yl)-2,5-diazabicyclo[2.2.1]heptan-2-yl)phenyl)-6-(1H-indol-6-yl)-[1,2,4]triazolo[1,5-a]pyrazin-8-amine;

N-(3-ethoxy-4-(5-(oxetan-3-yl)-2,5-diazabicyclo[2.2.1]heptan-2-yl)phenyl)-6-(1H-indol-6-yl)-[1,2,4]triazolo[1,5-a]pyrazin-8-amine;

N-(3-cyclopropoxy-4-(5-(oxetan-3-yl)-2,5-diazabicyclo[2.2.1]heptan-2-yl)phenyl)-6-(1H-indol-6-yl)-[1,2,4]triazolo[1,5-a]pyrazin-8-amine;

6-(1H-indol-6-yl)-N-(3-isopropoxy-4-(5-(oxetan-3-yl)-2,5-diazabicyclo[2.2.1]heptan-2-yl)phenyl)-[1,2,4]triazolo[1,5-a]pyrazin-8-amine; and 6-(1H-indol-6-yl)-N-(4-(5-(oxetan-3-yl)-2,5-diazabicyclo[2.2.1]heptan-2-yl)phenyl)-[1,2,4]triazolo[1,5-a]pyrazin-8-amine, or a pharmaceutically acceptable salt or tautomer thereof.

12. A pharmaceutical composition comprising at least one pharmaceutically acceptable carrier or excipient and a compound of claim 1, or a pharmaceutically acceptable salt, stereoisomer, or tautomer thereof.

13. A method for inhibiting spleen tyrosine kinase (Syk) activity in a patient, wherein the method comprises administering to the patient in need thereof a therapeutically effective amount of a compound of claim 1, or a pharmaceutically acceptable salt, stereoisomer, or tautomer thereof.

14. The method of claim 13, wherein the patient has a condition, disease, or disorder selected from the group consisting of an allergic disorder, an autoimmune disease, a cancer, and an inflammatory disorder.

15. The method of claim 14, wherein the allergic disorder, autoimmune disease, cancer, or inflammatory disorder is selected from the group consisting acute disseminated encephalomyelitis (ADEM), acute lymphocytic leukemia (ALL), acute myeloid leukemia (AML), of asthma, autoimmune hemolytic anemia, B-cell lymphoma, bladder cancer, bone cancer, breast cancer, central nervous system (CNS) cancer, cervical cancer, chronic lymphocytic leukemia (CLL), chronic myeloid leukemia (CML), colon cancer, colorectal cancer, Crohn's disease, dermatomyositis, esophageal cancer, follicular lymphoma, gastric cancer, head and neck cancer, hepatocellular cancer, idiopathic thrombocytopenia purpura, irritable bowel syndrome, lung cancer, lupus, melanoma, mantle cell lymphoma (MCL), multiple myeloma (MM), multiple sclerosis (MS), myasthenia gravis, myeloproliferative disorder (MPD), neuroendocrine cancer, non-Hodgkin's lymphoma (NHL), ovarian cancer, pancreatic cancer, prostate cancer, psoriasis, renal cancer, rheumatoid arthritis (RA), small lymphocytic lymphoma (SLL), soft tissue sarcoma, Sjögren's syndrome, T-cell lymphoma, ulcerative colitis, and Waldenström macroglobulinemia (WM).

16. The method of claim 15, wherein the lupus is systemic lupus erythematosus (SLE).

17. The method of claim 14, wherein the allergic disorder, autoimmune disease, cancer, or inflammatory disorder is selected from the group consisting of brain cancer, diffuse large B-cell lymphoma (DLBCL), myelodysplastic syndrome (MDS), non-small cell lung cancer (NSCLC), and small cell lung cancer (SCLC).

18. The method of claim 14, wherein the allergic disorder, autoimmune disease, cancer, or inflammatory disorder is selected from the group consisting of leukemia, lymphoma, and multiple myeloma.

19. The method of claim 14, wherein the allergic disorder, autoimmune disease, cancer, or inflammatory disorder is arterial thrombosis or thromboinflammation.

20. The method of claim 14, wherein the allergic disorder, autoimmune disease, cancer, or inflammatory disorder is a hematological malignancy.

21. The method of claim 13, wherein the patient is a human.

* * * * *